(12) United States Patent
Shierly et al.

(10) Patent No.: US 11,885,779 B2
(45) Date of Patent: Jan. 30, 2024

(54) ULTRAVIOLET MONITORING OF CHROMATOGRAPHY PERFORMANCE BY ORTHOGONAL PARTIAL LEAST SQUARES

(71) Applicant: Regeneron Pharmaceuticals, Inc., Tarrytown, NY (US)

(72) Inventors: Eric Shierly, Nassau, NY (US); Kevin Brennan, Menands, NY (US); Nathan Mao, Cohoes, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 296 days.

(21) Appl. No.: 17/229,186

(22) Filed: Apr. 13, 2021

(65) Prior Publication Data
US 2021/0318275 A1    Oct. 14, 2021

Related U.S. Application Data

(60) Provisional application No. 63/009,835, filed on Apr. 14, 2020.

(51) Int. Cl.
*G06F 17/18* (2006.01)
*G01N 21/33* (2006.01)
(Continued)

(52) U.S. Cl.
CPC ........... *G01N 30/74* (2013.01); *G01N 1/34* (2013.01); *G01N 21/33* (2013.01); *G01N 30/04* (2013.01);
(Continued)

(58) Field of Classification Search
CPC ........ G01N 30/04; G01N 30/74; G01N 30/88; G01N 1/34; G01N 21/33; G01N 33/48; G01N 30/8693; G01N 30/8658; G01N 30/8624; G01N 30/8675; G01N 30/8631; G01N 30/72; G01N 2030/027; G01N 2030/8886; G01N 2030/889; G06F 17/18;
(Continued)

(56) References Cited

U.S. PATENT DOCUMENTS

| 8,410,928 B2 * | 4/2013 | Ganguly ............ G01N 30/8693 340/540 |
| 2018/0113101 A1 | 4/2018 | Mao et al. |

FOREIGN PATENT DOCUMENTS

| CN | 109115933 A | | 1/2019 | |
| CN | 109923411 A | * | 6/2019 | ......... G01N 30/8617 |

OTHER PUBLICATIONS

WIPO Application No. PCT/2021/027043, PCT Invitation to Pay Additional Fees and, Where Applicable, Protest Fee dated Jul. 8, 2021.
(Continued)

*Primary Examiner* — Jeffrey P Aiello
(74) *Attorney, Agent, or Firm* — Schwabe, Williamson & Wyatt PC

(57) ABSTRACT

Disclosed are methods for monitoring column chromatography performance. The methods can include acquiring one or more chromatogram ultraviolet (UV) traces generated by a chromatography system during sample purification and/or separation; and analyzing the one or more acquired chromatogram UV traces with an orthogonal partial least squares (OPLS) model, thereby allowing detection of column deterioration prior to column failure and quantitative analysis of UV signal in the one or more chromatogram UV traces.

18 Claims, 67 Drawing Sheets

(51) Int. Cl.
*G01N 30/88* (2006.01)
*G01N 30/74* (2006.01)
*G01N 1/34* (2006.01)
*G01N 30/04* (2006.01)
*G01N 33/48* (2006.01)
*G01N 30/02* (2006.01)

(52) U.S. Cl.
CPC ............. *G01N 30/88* (2013.01); *G01N 33/48* (2013.01); *G06F 17/18* (2013.01); *G01N 2030/027* (2013.01); *G01N 2030/8886* (2013.01)

(58) Field of Classification Search
CPC ............. G06F 2218/00; G06F 2218/08; G06F 2218/14; G05B 23/0254; G05B 23/024
USPC ........... 73/23.36, 61.52, 23.23, 23.35, 61.57, 73/23.2, 23.22, 53.01, 1.01; 700/28, 266, 700/30, 47, 49, 48; 702/32, 22, 19, 23, 702/28, 27, 189, 30, 182, 85
See application file for complete search history.

(56) References Cited

OTHER PUBLICATIONS

WIPO Application No. PCT/2021/027043, PCT International Search Report and Written Opinion of the International Searching Authority dated Sep. 2, 2021.

\* cited by examiner

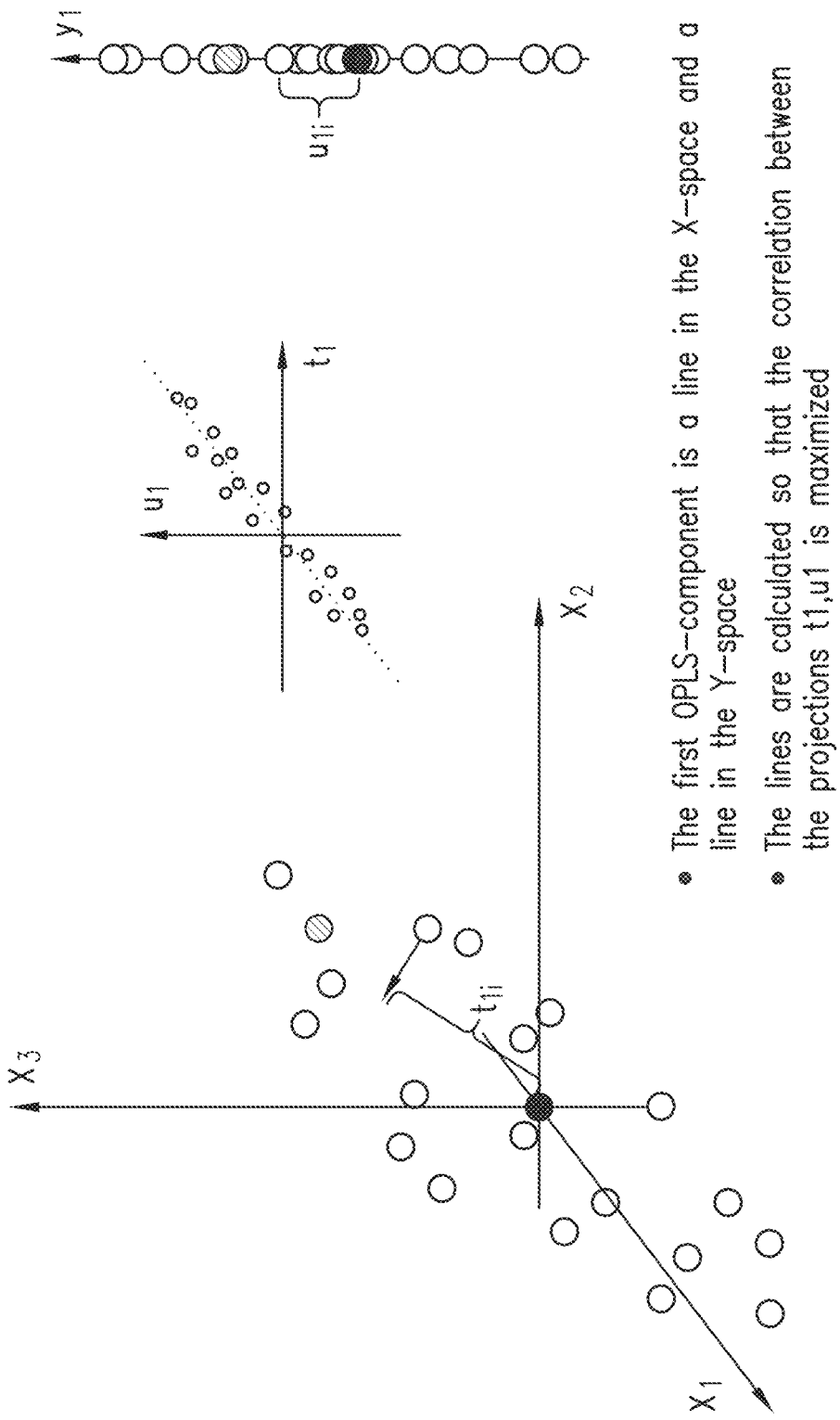

FIG. 4

| | A | B | C | D | E | F | G | H | I | J | K | L | M | N | O | P |
|---|---|---|---|---|---|---|---|---|---|---|---|---|---|---|---|---|
| 1 | Chrom.1 | | Chrom.1 | | | | | | | | | | | | | |
| 2 | UV 1_131 | | Run Log | | | | | | | | | | | | | |
| 3 | | AU | | | | | | | | | | | | | | |
| 4 | 0 | 0 | 0 | Logbook | | | | | | | | | | | | |
| 5 | 0.365351 | 0.0001 | 0 | Method Run 2/14/2020 1:45:41 PM −05:00 Method: PA7 REGN668 ProA Load Elution Revision 1 Result:/ECN54013 | | | | | | | | | | | | |
| 6 | 0.730702 | 8.73E−05 | 0 | Batch ID: c3a5cb72−07dc−4545−9a59−f627e5a6502f | | | | | | | | | | | | |
| 7 | 1.096053 | 1.00E−04 | 0 | Base CV, Vc=157.000 {l}, Any | | | | | | | | | | | | |
| 8 | 1.461404 | 8.38E−05 | 0 | Phase Method Settings | | | | | | | | | | | | |
| 9 | 1.826755 | 1.11E−05 | 0 | Base SameAsMain | | | | | | | | | | | | |
| 10 | 2.192106 | 1.00E−04 | 0 | End Phase | | | | | | | | | | | | |
| 11 | 2.557457 | 7.18E−04 | 0 | Phase User Defined | | | | | | | | | | | | |
| 12 | 2.922808 | 0.001177 | 0 | Base SameAsMain | | | | | | | | | | | | |
| 13 | 3.288159 | 7.86E−05 | 0 | Press_PIA111_Alarm 4.00 {bar} 0.00 {bar} 4.00 {bar} 0.00 {bar} Enabled | | | | | | | | | | | | |
| 14 | 3.65351 | 5.63E−05 | 0 | Press_PIA112_Alarm 3.00 {bar} 0.00 {bar} 3.00 {bar} 0.00 {bar} Enabled | | | | | | | | | | | | |
| 15 | 4.018861 | 0 | 0 | AirTrapLevelControl Disabled 10.0 {sec} | | | | | | | | | | | | |
| 16 | 4.384212 | 0.0001 | 0 | Block Set_Up | | | | | | | | | | | | |
| 17 | 4.749563 | 1.28E−07 | 0 | Base SameAsMain | | | | | | | | | | | | |
| 18 | 5.114914 | 6.67E−05 | 0 | Message Ensure the column equilibration has been performed" | | | | | | | | | | | | |
| 19 | 5.480265 | 0.00E+00 | 0 | Message Ensure that the column is in bypass and the MPTV and MPBV are closed" | | | | | | | | | | | | |
| 20 | 5.845616 | 7.41E−05 | 0 | Message Ensure appropriate filter has been installed" | | | | | | | | | | | | |
| 21 | 6.210967 | 0.0001 | 0 | Message Ensure harvest material is connected to INLET A1/air sensor and primed" | | | | | | | | | | | | |
| 22 | 6.576318 | 0.00E+00 | 0 | Message Ensure Buffer 1 (item master number 10416) is connected to inlet A2." | | | | | | | | | | | | |
| 23 | 6.941669 | 0.0001 | 0 | Message Ensure Buffer 2 (item master number 10487) is connected to inlet B1." | | | | | | | | | | | | |
| 24 | 7.30702 | 1.14E−05 | 0 | Message Ensure Buffer 3 (item master number 10488) is connected to inlet B2." | | | | | | | | | | | | |
| 25 | 7.672371 | 1.93E−05 | 0 | Message Ensure Buffer 4 (item master number 10415) is connected to inlet B3." | | | | | | | | | | | | |
| 26 | 8.037722 | 0.0001 | 0 | Message Ensure the pool vessel is set up and connected to outlet 1." | | | | | | | | | | | | |
| 27 | 8.403073 | 5.17E−05 | 0 | Message Ensure Outlet 2 is connected to drain" | | | | | | | | | | | | |
| 28 | 8.768424 | 1.00E−04 | 0 | Message Click "Continue" when complete." | | | | | | | | | | | | |
| 29 | 9.133775 | 8.08E−06 | 0 | Pause Infinite min 2/14/2020 1:45:41 PM −05:00 | | | | | | | | | | | | |
| | | | | Message Ensure the column equilibration has been performed" confirmed by REGENERON/aissa.reyes (Manual)" | | | | | | | | | | | | |

Each column corresponds to the UV values for a certain CV point in the analysis
Ex: 0.1 CVs into the elution block

| | G | H | I | J | K | L | M | N | O |
|---|---|---|---|---|---|---|---|---|---|
| Lot_cycle | 0 | 0.02 | 0.04 | 0.06 | 0.08 | 0.1 | 0.12 | 0.14 | 0.16 |
| 1_1 | -1.02032 | -0.99778 | -0.99705 | -0.99707 | -0.99778 | -0.99781 | -0.99778 | -0.99842 | -0.99852 |
| 1_2 | -1.01667 | -0.99781 | -0.99703 | -0.99771 | -0.99771 | -0.99771 | -0.99771 | -0.99782 | -0.99852 |
| 1_3 | -1.01593 | -0.99778 | -0.99698 | -0.99778 | -0.99778 | -0.99778 | -0.99778 | -0.99852 | -0.99852 |
| 1_4 | -1.01742 | -0.99705 | -0.99704 | -0.99703 | -0.99778 | -0.99778 | -0.99771 | -0.99778 | -0.99845 |
| 1_5 | -1.01593 | -0.99776 | -0.99779 | -0.99779 | -0.99779 | -0.99779 | -0.99846 | -0.99846 | -0.99852 |
| 1_6 | -1.01525 | -0.99785 | -0.99711 | -0.99711 | -0.99778 | -0.9978 | -0.99785 | -0.99785 | -0.99859 |
| 2_1 | -1.02035 | -0.99784 | -0.99707 | -0.99784 | -0.99778 | -0.99778 | -0.99854 | -0.99852 | -0.99853 |
| 2_2 | -1.01742 | -0.99778 | -0.99704 | -0.99778 | -0.99773 | -0.99773 | -0.99778 | -0.99845 | -0.99845 |
| 2_3 | -1.01742 | -0.99704 | -0.99704 | -0.99704 | -0.99704 | -0.99771 | -0.99775 | -0.99771 | -0.99775 |
| 2_4 | -1.01667 | -0.99697 | -0.99701 | -0.99704 | -0.99701 | -0.99698 | -0.99771 | -0.99771 | -0.99771 |
| 2_5 | -1.01593 | -0.99706 | -0.99627 | -0.99698 | -0.99698 | -0.99698 | -0.99698 | -0.99779 | -0.99778 |
| 2_6 | -1.01667 | -0.99704 | -0.99704 | -0.99704 | -0.99779 | -0.9978 | -0.99771 | -0.99775 | -0.99852 |

All UV Values Normalized to -1 to 1

Each row corresponds to the UV values for a certain run/cycle
Ex: _6

| P | Q | R | S | T | U | V | W | X | Y | Z |
|---|---|---|---|---|---|---|---|---|---|---|
| 0.18 | 0.2 | 0.22 | 0.24 | 0.26 | 0.28 | 0.3 | 0.32 | 0.34 | 0.36 | 0.38 |
| -0.99852 | -0.99856 | -0.99852 | -0.99926 | -0.99925 | -0.99926 | -0.99926 | -0.99926 | -0.99994 | -0.99994 | -0.99994 |
| -0.99857 | -0.99852 | -0.99852 | -0.99926 | -0.99921 | -0.99926 | -0.99921 | -0.99924 | -0.99926 | -0.9992 | -1 |
| -0.99852 | -0.99852 | -0.99926 | -0.99926 | -0.99926 | -0.99926 | -0.99924 | -0.99926 | -0.99993 | -0.99993 | -0.99993 |
| -0.99845 | -0.99845 | -0.99845 | -0.99857 | -0.99926 | -0.99913 | -0.99926 | -0.99926 | -0.99918 | -0.99993 | -0.99999 |
| -0.99853 | -0.99847 | -0.99923 | -0.99927 | -0.99924 | -0.99927 | -0.99927 | -0.99922 | -0.99999 | -0.99997 | -0.99999 |
| -0.99859 | -0.99859 | -0.99859 | -0.99856 | -0.99928 | -0.99926 | -0.99931 | -0.99926 | -0.99926 | -0.99932 | -0.99994 |
| -0.99852 | -0.99852 | -0.99926 | -0.99919 | -0.99923 | -0.99926 | -0.99926 | -0.99925 | -0.99994 | -0.99993 | -0.99926 |
| -0.99854 | -0.99853 | -0.99845 | -0.99926 | -0.99914 | -0.99926 | -0.99926 | -0.99927 | -1 | -1 | -0.99999 |
| -0.99845 | -0.99845 | -0.99845 | -0.99845 | -0.99926 | -0.99926 | -0.99926 | -0.99926 | -0.99926 | -0.99993 | -0.99997 |
| -0.99845 | -0.99845 | -0.99845 | -0.99856 | -0.99926 | -0.99923 | -0.99926 | -0.99926 | -0.99924 | -0.99993 | -0.99996 |
| -0.99771 | -0.99852 | -0.99852 | -0.99848 | -0.99852 | -0.99848 | -0.99853 | -0.99926 | -0.99924 | -0.99919 | -0.99922 |
| -0.99778 | -0.9977 | -0.99846 | -0.99848 | -0.99845 | -0.99851 | -0.99845 | -0.99926 | -0.99924 | -0.99926 | -0.99923 |
| -0.99858 | -0.99852 | -0.99852 | -0.99926 | -0.99926 | -0.99926 | -0.99926 | -0.99926 | -0.99919 | -0.99998 | -1 |

Cont. From FIG.5-1

FIG.5-2

Curve to be fitted by
the mathematical model

| | A | E | F | G | H | I |
|---|---|---|---|---|---|---|
| 1 | | | | | | |
| 2 | Normalized | | | | | |
| 3 | 0 | -1.016671148 | -1.020315753 | -1.016671148 | -1.015926146 | -1.017417034 |
| 4 | 0.02 | -0.997042216 | -0.997781731 | -0.997811502 | -0.997782811 | -0.997045385 |
| 5 | 0.04 | -0.997042216 | -0.997705085 | -0.997026311 | -0.99697644 | -0.997041122 |
| 6 | 0.06 | -0.997042216 | -0.997074679 | -0.997714439 | -0.997782811 | -0.997033556 |
| 7 | 0.08 | -0.997778236 | -0.997781731 | -0.997714439 | -0.997782811 | -0.99778084 |
| 8 | 0.1 | -0.997799287 | -0.997807756 | -0.997714439 | -0.997782811 | -0.99778084 |
| 9 | 0.12 | -0.997714439 | -0.997781731 | -0.997781731 | -0.997781731 | -0.997713594 |
| 10 | 0.14 | -0.997775084 | -0.998422565 | -0.997819696 | -0.997780641 | -0.99778084 |
| 11 | 0.16 | -0.998521108 | -0.998522798 | -0.998521108 | -0.998521983 | -0.998453314 |
| 12 | 0.18 | -0.998578818 | -0.998522798 | -0.998569313 | -0.998521983 | -0.998453314 |
| 13 | 0.2 | -0.998521108 | -0.998555441 | -0.998521108 | -0.998521983 | -0.998453314 |
| 14 | 0.22 | -0.998521108 | -0.998522798 | -0.998521108 | -0.999261156 | -0.998570747 |
| 15 | 0.24 | -0.999260554 | -0.999226865 | -0.999221367 | -0.999261156 | -0.99926028 |
| 16 | 0.26 | -0.999260554 | -0.999252007 | -0.999207926 | -0.999210678 | -0.999128745 |
| 17 | 0.28 | -0.999260554 | -0.999226865 | -0.999260554 | -0.999241326 | -0.999260028 |
| 18 | 0.3 | -0.999260554 | -0.999226865 | -0.999212187 | -0.999260554 | -0.999260028 |
| 19 | 0.32 | -0.999260554 | -0.999937562 | -0.993244777 | -0.999260554 | -0.999179718 |
| 20 | 0.34 | -0.999919822 | -0.999937562 | -0.999260554 | -0.999933132 | -0.999932753 |
| 21 | 0.36 | -0.999998768 | -0.999937562 | -0.999204806 | -0.999933132 | -0.999985401 |
| 22 | 0.38 | -1 | -0.999937562 | -1 | -0.999933132 | -0.999979335 |
| 23 | 0.4 | -0.999948192 | -0.999937562 | -0.999986226 | -0.999933132 | -1 |
| 24 | 0.42 | -1 | -0.999937562 | -1 | -0.999953132 | -0.999963329 |
| 25 | 0.44 | -0.999932778 | -0.999938215 | -0.999993439 | -0.999993132 | -0.99999885 |
| 26 | 0.46 | -1 | -0.99999357 | -0.9999958685 | -0.999958685 | -0.99999885 |
| 27 | 0.48 | -0.998521108 | -0.999218423 | -0.999260554 | -0.998521983 | -0.998112969 |
| 28 | 0.5 | -0.992101539 | -0.994143766 | -0.994860769 | -0.99200382 | -0.989787297 |
| 29 | 0.52 | -0.980638646 | -0.983354754 | -0.984807744 | -0.980533693 | -0.975665555 |
| 30 | 0.54 | -0.967811166 | -0.970614809 | -0.971311004 | -0.966940928 | -0.959192408 |
| 31 | 0.56 | -0.952185218 | -0.957808857 | -0.956500222 | -0.952173711 | -0.941361756 |
| 32 | 0.58 | -0.9347343 | -0.945767724 | -0.940809895 | -0.938682307 | -0.924289768 |
| 33 | 0.6 | -0.916170409 | -0.931018336 | -0.924513848 | -0.922575796 | -0.906650284 |
| 34 | 0.62 | -0.89458712 | -0.914367169 | -0.906074415 | -0.904114482 | -0.888780606 |
| 35 | 0.64 | -0.86955398 | -0.894299806 | -0.884811172 | -0.88284962 | -0.866013113 |
| 36 | 0.66 | -0.84147143 | -0.871514097 | -0.859812987 | -0.858330582 | -0.840916042 |
| 37 | 0.68 | -0.80981608 | -0.845002023 | -0.831952272 | -0.831057655 | -0.811299667 |

Generation | Manipulation | Import

RMSE Value

| Description | | Σ((p − o)^2) | 0.25146 | RMSE: | 0.040 |
|---|---|---|---|---|---|
| height of peak liftoff | Start: | | | | Raw |
| liftoff location | hm1 | 0.85 | | | 7.68 |
| liftoff steepness | tm1 | 0.81 | | | 1.69 |
| | s1 | 0.04 | | | 2.90 |
| | | | | | 3.87 |
| Height of peak dropdown | End: | | | | 4.03 |
| Dropdown location | hm2 | 0.84 | | | 3.26 |
| Dropdown steepness | tm2 | 1.69 | | | 2.06 |
| | s2 | 0.21 | | | 1.0 |
| | Boundaries: | | | | 3.88 |
| Point where eqn1->eqn pmstart | | 0.81 | | | 1.1 |
| Point where eqn2->eqn pmend | | 1.69 | | | 2.6 |
| | | | | | 4.85 |
| Ht of 1/3 eqns | uniform h | 0.85 | | | 6.83 |
| | | | | | 7.49 |
| | Max: | | | | 6.40 |
| Height of peak max | hm3 | 0 | | | 4.26 |
| Location of peak max | tm3 | 0.92 | | | 2.20 |
| Width of peak max | s3 | 0.01 | | | 8.90 |
| | | | | | 2.79 |
| | Tailing factor: | | | | 6.84 |
| Increases tailing | tail | 0.01 | | | 1.30 |
| | | | | | 1.93 |
| Key | | | | | 2.23 |
| Parameter should remain constant | | | | | 2.01 |
| Parameter should be changed | | | | | 1.4 |
| | | | | | 7.70 |
| | | | | | 3.27 |
| | | | | | 1.08 |
| | | | | | 2.79 |
| | | | | | 5.62 |
| | | | | | 8.79 |
| | | | | | 1.07 |
| | | | | | 0.000 |
| | | | | | 0.000 |
| | | | | | 0.004 |

Cont. From FIG.6-2

FIG. 7

| | | | | | AVG | STD DEV |
|---|---|---|---|---|---|---|
| -0.97647 | -0.97647 | -0.97647 | -0.97647 | | | |
| -0.97647 | -0.97647 | -0.97647 | -0.97647 | | | |
| -0.97647 | -0.97647 | -0.97647 | -0.97647 | | | |
| tm1 | 0.82 | 0.81 | 0.81 | 0.81 | 0.8125 | 0.00433 |
| s1 | 0.04 | 0.04 | 0.04 | 0.04 | 0.04 | 0 |
| tm2 | 1.66 | 1.66 | 1.68 | 1.69 | 1.6725 | 0.01299 |
| s2 | 0.21 | 0.21 | 0.21 | 0.21 | 0.21 | 0 |
| hm3 | 0 | 0 | 0 | 0 | 0 | 0 |
| tm3 | 1.26 | 1 | 0.92 | 0.92 | 1.025 | 0.139553 |
| s3 | 1.21 | 0.01 | 0.01 | 0.01 | 0.31 | 0.519615 |
| tail | 0.01 | 0.01 | 0.01 | 0.01 | 0.01 | 0 |
| MinDiff | 0.23614 | 0.339912 | 0.191561 | 0.251465 | 0.25477 | 0.053857 |

Curve Generation tool will store the parameters for the mathematical equation for each generated curve Curve Generation tool will store the mean and Standard Deviation for the parameters of each generated curve

FIG. 8

Copy Mean and SD values from generation tab into table

| W | X | Y | Z |
|---|---|---|---|
| | AVG | SD | |
| tm1 | 0.8125 | 0.00433 | |
| s1 | 0.04 | 0 | |
| tm2 | 1.6725 | 0.01299 | |
| s2 | 0.21 | 0 | |
| hm3 | 0 | 0 | |
| tm3 | 1.025 | 0.139555 | |
| s3 | 0.31 | 0.51962 | |
| tail | 0.01 | 0 | |
| | 0.2548 | 0.05386 | |

Adjust SD values to generate Chromatograms representative of column deterioration. Parameter values will be equal to the mean plus the number of standard deviations specified

| AA | AB | AC | AD |
|---|---|---|---|
| Description | Start: | | SD |
| height of peak liftoff | hm1 | 0.85 | 0 |
| liftoff location | tm1 | 0.8125 | 0 |
| liftoff steepness | s1 | 0.04 | 0 |
| | End: | | |
| Height of peak dropdown | hm2 | 0.84 | 0 |
| Dropdown location | tm2 | 1.6725 | 0 |
| Dropdown steepness | s2 | 0.21 | 0 |
| | Boundaries: | | |
| Point where eqn1->eqn2 | pmstart | 0.8125 | 0 |
| Point where eqn2->eqn3 | pmend | 1.6725 | 0 |
| ht of 1/3 eqns | unifo | 0.85 | 0 |
| | Max. | | |
| Height of peak max | hm3 | 0 | 0 |
| Location of peak max | tm3 | 1.025 | 0 |
| Width of peak max | s3 | 0.31 | 0 |
| | Tailing factor: | | |
| increases tailing | tail | 0.01 | 0 |
| Key | | | |
| Parameter should remain constant | | | |

FIG.9-2

Cont. From FIG.9-1

S1 Value was manually changed to 0.1
(SD was 0 so had to manually adjust)

Normalized UV values for artificial curve are stored. Copy values into columns to the right to save values. Name the curve based on what parameter was changed (Ex: s1:0.1)

| W | X | Y | Z | AA | AB | AC | AD | AE | AF | AG |
|---|---|---|---|---|---|---|---|---|---|---|
|  | AVG | SD |  | Description | Start: |  | SD | 0.276329 | 0.2763918 | Ynorm |
| fm1 | 0.8125 | 0.00433 |  | height of peak liftoff | fm1 | 0.85 | 0 |  | 3.9292E-15 | -1 |
| s1 | 0.04 | 0 |  | Liftoff location | fm1 | 0.8125 |  |  | 1.9559E-14 | -1 |
| fm2 | 1.6725 | 0.01299 |  | Liftoff steepness | s1 | 0.1 |  |  | 9.3545E-14 | -1 |
| s2 | 0.21 | 0 |  |  |  |  |  |  | 4.2985E-13 | -1 |
| hm3 | 0 | 0.13955 |  | Height of peak dropdown | hm2 | 0.84 |  |  | 1.8978E-12 | -1 |
| fm3 | 1.025 | 0.51962 |  | Dropdown location | fm2 | 1.6725 |  |  | 8.0501E-12 | -1 |
| s3 | 0.31 | 0 |  | Dropdown steepness | s2 | 0.21 |  |  | 3.2809E-11 | -1 |
| tail | 0.01 | 0 |  |  |  |  |  |  | 1.2847E-10 | -1 |
|  | 0.2548 | 0.05386 |  | Point where eqn1->eqn pmstart | 0.8125 |  |  |  | 4.8333E-10 | -1 |
|  |  |  |  | Point where eqn2->eqn pmend | 1.6725 |  |  |  | 1.7471E-09 | -1 |
|  |  |  |  |  | Boundaries: |  |  |  | 6.0674E-09 | -1 |
|  |  |  |  | ht of 1/3 eqns | unifo | 0.85 |  |  | 2.0246E-08 | -1 |
|  |  |  |  |  |  |  |  |  | 6.4906E-08 | -0.99999 |
|  |  |  |  |  | Max: |  |  |  | 1.992E-07 | -0.99997 |
|  |  |  |  | Height of peak max | hm3 | 0 |  |  | 5.9166E-07 | -0.99993 |
|  |  |  |  | Location of peak max | fm3 | 1.025 |  |  | 1.6823E-06 | -0.99983 |
|  |  |  |  | Width of peak max | s3 | 0.31 |  |  | 4.596E-06 | -0.9996 |
|  |  |  |  |  |  |  |  |  | 1.2063E-05 | -0.9991 |
|  |  |  |  |  | Tailing factor: |  |  |  | 3.0422E-05 | -0.99806 |
|  |  |  |  | Increases tailing | tail | 0.01 |  |  | 7.3713E-05 | -0.99599 |
|  |  |  |  |  |  |  |  |  | 0.0001716 | -0.99205 |
|  |  |  |  | Key |  |  |  |  | 0.00038382 | -0.98485 |
|  |  |  |  | Parameter should remain constant |  |  |  |  | 0.0008248 | -0.97225 |
|  |  |  |  | Parameter should be changed |  |  |  |  | 0.00170306 |  |
|  |  |  |  |  |  |  |  |  | 0.00337847 |  |
|  |  |  |  |  |  |  |  |  | 0.00643953 |  |
|  |  |  |  |  |  |  |  |  | 0.01179203 |  |

Cont. From FIG.10-1

FIG. 10-2

| | A | B | C | D | G | H | I | J | K | L |
|---|---|---|---|---|---|---|---|---|---|---|
| 1 | Lot_cycle | Process Area | Column Pack | Good/Bad | 0 | 0.02 | 0.04 | 0.06 | 0.08 | 0.1 |
| 2 | 1 | PA7 | 32 | Good | 1.02032 | -0.99778 | -0.99705 | -0.99707 | -0.99778 | -0.99781 |
| 3 | 2 | PA7 | 32 | Good | 1.01667 | -0.99781 | -0.99703 | -0.99771 | -0.99771 | -0.99771 |
| 4 | 3 | PA7 | 32 | Good | 1.01593 | -0.99778 | -0.99698 | -0.99778 | -0.99778 | -0.99778 |
| 5 | 4 | PA7 | 32 | Good | 1.01742 | -0.99705 | -0.99704 | -0.99703 | -0.99778 | -0.99778 |
| 6 | 5 | PA7 | 32 | Good | 1.01593 | -0.99776 | -0.99779 | -0.99779 | -0.99779 | -0.99779 |
| 7 | 6 | PA7 | 32 | Good | 1.01525 | -0.99785 | -0.99711 | -0.99711 | -0.99778 | -0.9978 |
| 8 | 1 | PA7 | 32 | Good | 1.02035 | -0.99784 | -0.99707 | -0.99784 | -0.9978 | -0.9978 |
| 9 | 2 | PA7 | 32 | Good | 1.01742 | -0.99778 | -0.99704 | -0.99778 | -0.99778 | -0.99773 |
| 10 | 3 | PA7 | 32 | Good | 1.01742 | -0.99704 | -0.99704 | -0.99704 | -0.99704 | -0.99771 |
| 11 | 4 | PA7 | 32 | Good | 1.01667 | -0.99697 | -0.99701 | -0.99704 | -0.99701 | -0.99698 |
| 12 | 5 | PA7 | 32 | Good | 1.01593 | -0.99706 | -0.99627 | -0.99698 | -0.99698 | -0.99698 |
| 13 | 6 | PA7 | 32 | Good | 1.01667 | -0.99704 | -0.99704 | -0.99704 | -0.99779 | -0.9978 |
| 14 | 329.1 | PGC | | Good | 1 | 1 | 1 | 1 | 1 | 1 |
| 15 | 329.6 | PGC | | Good | 1 | 1 | 1 | 1 | 1 | 1 |
| 16 | 331.1 | PGC | | Good | 1 | 1 | 1 | 1 | 1 | 1 |
| 17 | 331.6 | PGC | | Good | 1 | 1 | 1 | 1 | 1 | 1 |
| 18 | s1:0.1 | PGC | | Bad | -3.35294 | -3.35294 | -3.35294 | -3.35294 | -3.35294 | -3.35294 |
| 19 | s1:0.12 | PGC | | Bad | 1 | 1 | 1 | 1 | 1 | 1 |
| 20 | s2:0.5 | PGC | | Bad | 1 | 1 | 1 | 1 | 1 | 1 |
| 21 | s2:0.4 | PGC | | Bad | 1 | 1 | 1 | 1 | 1 | 1 |
| 22 | s2:0.35 | PGC | | Bad | 1 | 1 | 1 | 1 | 1 | 1 |
| 23 | tm1:0.65 | PGC | | Bad | 1 | 1 | 1 | 1 | 1 | 1 |
| 24 | tm1:0.68 | PGC | | Bad | 1 | 1 | 1 | 1 | 1 | 1 |
| 25 | tm2:2 | PGC | | Bad | 1 | 1 | 1 | 1 | 1 | 1 |
| 26 | tm2:1.75, s2:0.35 | PGC | | Bad | 1 | 1 | 1 | 1 | 1 | 1 |
| 27 | tm1:0.78, s1:0.1 | PGC | | Bad | 1 | 1 | 1 | 1 | 1 | 1 |

Normalized raw data imported

Artificially generated "good" curves

Artificially generated "bad" curves

Classification groups: "Good" or "Bad" Classification for each lot

Normalized UV values for each run

| M | N | O | P | Q | R | S | T | U | V | W | X |
|---|---|---|---|---|---|---|---|---|---|---|---|
| 0.12 | 0.14 | 0.16 | 0.18 | 0.2 | 0.22 | 0.24 | 0.26 | 0.28 | 0.3 | 0.32 | 0.3 |
| −0.99778 | −0.99842 | −0.99852 | −0.99852 | −0.99856 | −0.99852 | −0.99926 | −0.99925 | −0.99926 | −0.99926 | −0.99926 | −0.9999 |
| −0.99771 | −0.99782 | −0.99852 | −0.99857 | −0.99852 | −0.99852 | −0.99921 | −0.99921 | −0.99926 | −0.99921 | −0.99924 | −0.9992 |
| −0.99778 | −0.99852 | −0.99852 | −0.99852 | −0.99852 | −0.99926 | −0.99926 | −0.99926 | −0.99921 | −0.99924 | −0.99926 | −0.9999 |
| −0.99771 | −0.99778 | −0.99845 | −0.99845 | −0.99845 | −0.99845 | −0.99857 | −0.99926 | −0.99913 | −0.99926 | −0.99926 | −0.9999 |
| −0.99846 | −0.99852 | −0.99852 | −0.99853 | −0.99847 | −0.99923 | −0.99927 | −0.99924 | −0.99927 | −0.99927 | −0.99922 | −0.9999 |
| −0.99785 | −0.99846 | −0.99859 | −0.99859 | −0.99859 | −0.99859 | −0.99856 | −0.99928 | −0.99926 | −0.99931 | −0.99926 | −0.9999 |
| −0.99854 | −0.99785 | −0.99853 | −0.99854 | −0.99852 | −0.99926 | −0.99919 | −0.99923 | −0.99926 | −0.99926 | −0.99925 | −0.9992 |
| −0.99778 | −0.99852 | −0.99845 | −0.99845 | −0.99853 | −0.99845 | −0.99926 | −0.99914 | −0.99926 | −0.99926 | −0.99927 | −0.9999 |
| −0.99775 | −0.99845 | −0.99775 | −0.99845 | −0.99845 | −0.99845 | −0.99845 | −0.99926 | −0.99923 | −0.99926 | −0.99926 | −0.9992 |
| −0.99771 | −0.99771 | −0.99771 | −0.99771 | −0.99852 | −0.99852 | −0.99856 | −0.99852 | −0.99848 | −0.99853 | −0.99926 | −0.9992 |
| −0.99698 | −0.99779 | −0.99778 | −0.99778 | −0.99977 | −0.99846 | −0.99848 | −0.99845 | −0.99851 | −0.99845 | −0.99926 | −0.9992 |
| −0.99771 | −0.99775 | −0.99852 | −0.99858 | −0.99852 | −0.99852 | −0.99926 | −0.99926 | −0.99926 | −0.99926 | −0.99926 | −0.9991 |
| −1 | −1 | −1 | −1 | −1 | −1 | −1 | −1 | −1 | −1 | −1 | −1 |
| −1 | −1 | −1 | −1 | −1 | −1 | −1 | −1 | −1 | −1 | −1 | −1 |
| −3.35294 | −3.35294 | −3.35294 | −3.35294 | −3.35294 | −3.35294 | −3.35294 | −3.35294 | −3.35294 | −3.35294 | −3.35294 | −3.35294 |
| −1 | −1 | −1 | −1 | −1 | −0.99999 | −0.99998 | −0.99995 | −0.99989 | −0.99978 | −0.99956 | −0.9991 |
| −1 | −1 | −1 | −1 | −1 | −1 | −1 | −1 | −1 | −1 | −1 | −1 |
| −1 | −1 | −1 | −1 | −1 | −1 | −1 | −1 | −1 | −1 | −1 | −1 |
| −1 | −1 | −1 | −1 | −1 | −1 | −1 | −1 | −1 | −1 | −1 | −1 |
| −1 | −1 | −1 | −1 | −1 | −1 | −1 | −1 | −1 | −1 | −1 | −1 |
| −0.99977 | −1 | −1 | −1 | −1 | −1 | −1 | −1 | −0.99999 | −0.99998 | −0.99995 | −0.9998 |

Cont. From FIG. 11-1

FIG. 11-2

1. Save Excel file as regular excel file (not macro enabled)
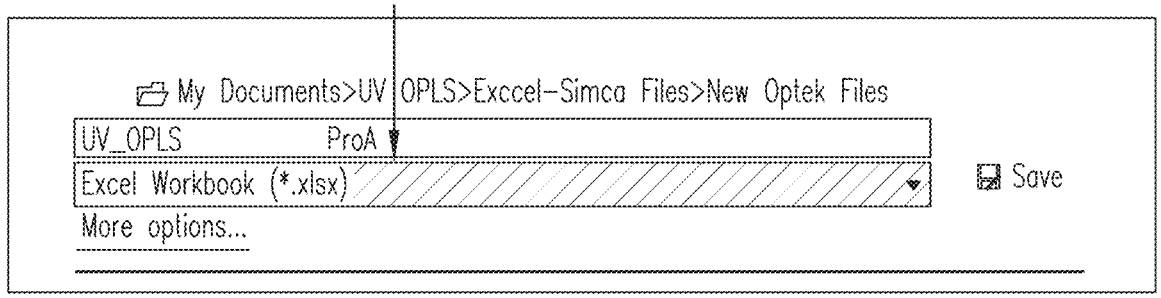
2. Open Simca and Select "File"
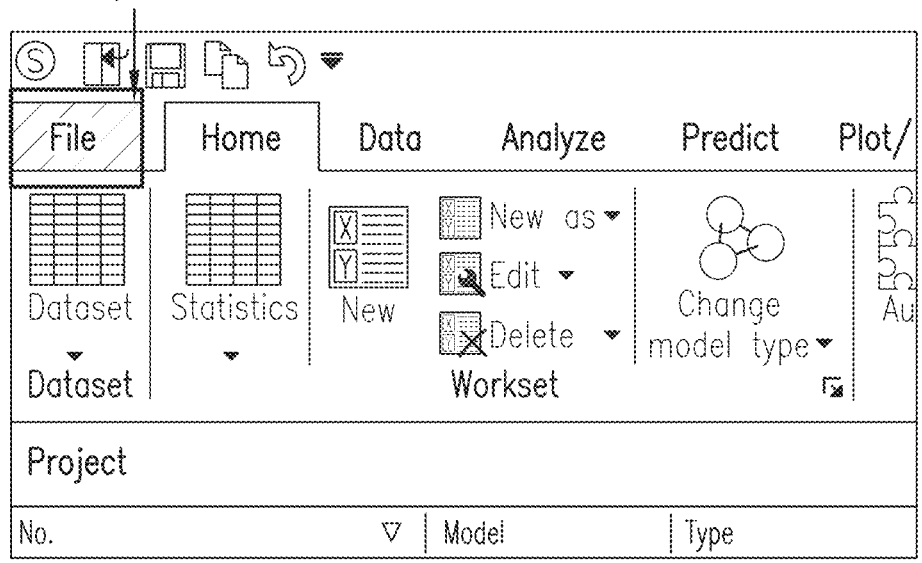
FIG.12A 3. Select "New" then Regular project
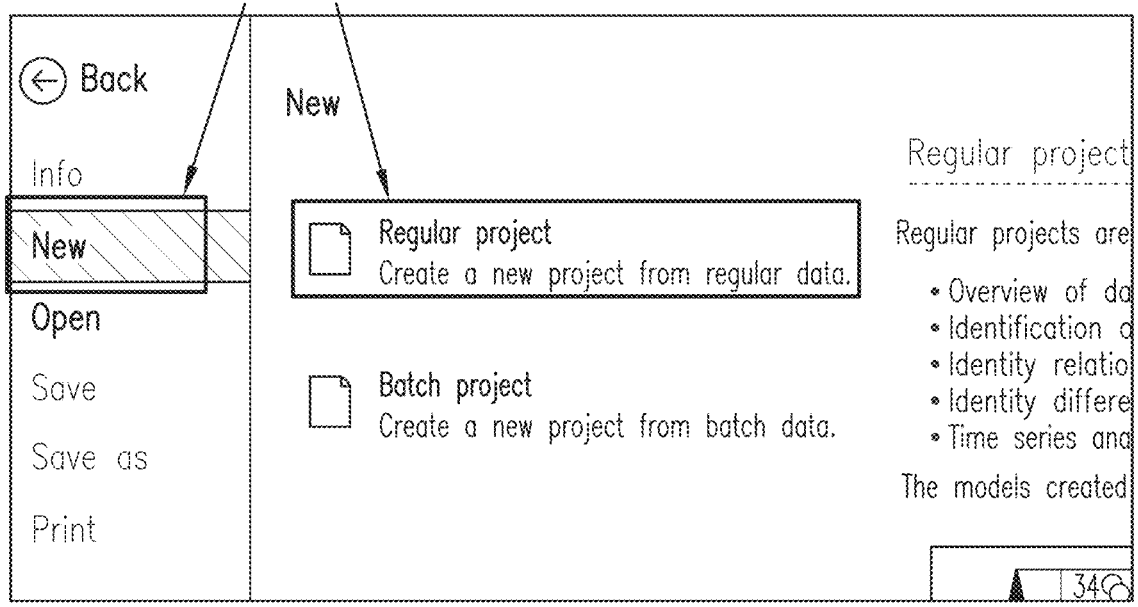
4. Select Excel file and Select "Open"
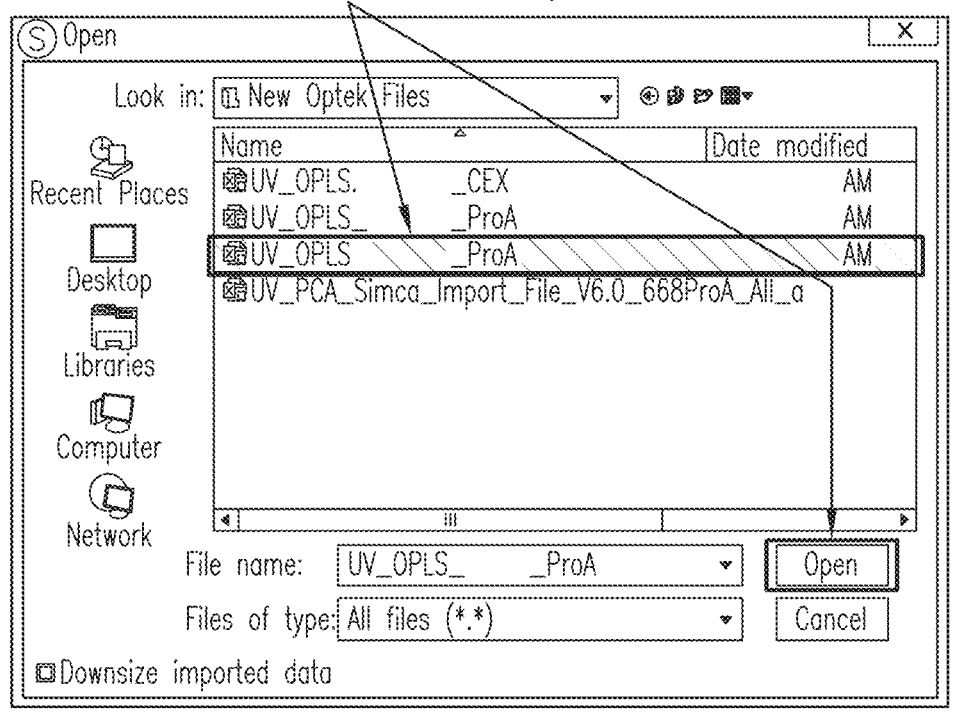
FIG.12B

| | Primary ID | Qualitative | 3 | Qualitative | 5 | 6 | 7 |
|---|---|---|---|---|---|---|---|
| 1 | Lot_cycle | Process Area | Column Pack | Good/Bad | Bifurcation? | Severe Tailing? | 0 |
| 2 | | 1 PA7 | 32 | Good | | | -1.02032 |
| 3 | | 2 PA7 | 32 | Good | | | -1.01667 |
| 4 | | 3 PA7 | 32 | Good | | | -1.01593 |
| 5 | | 4 PA7 | 32 | Good | | | -1.01742 |
| 6 | | 5 PA7 | 32 | Good | | | -1.01593 |
| 7 | | 6 PA7 | 32 | Good | | | -1.01525 |
| 8 | | 1 PA7 | 32 | Good | | | -1.02035 |
| 9 | | 2 PA7 | 32 | Good | | | -1.01742 |
| 10 | | 3 PA7 | 32 | Good | | | -1.01742 |
| 11 | | 4 PA7 | 32 | Good | | | -1.01667 |
| 12 | | 5 PA7 | 32 | Good | | | -1.01593 |
| 13 | | 6 PA7 | 32 | Good | | | -1.01667 |
| 14 | 329_1 | PGC | PGC | Good | | | -1 |
| 15 | 329_6 | PGC | PGC | Good | | | -1 |
| 16 | 331_1 | PGC | PGC | Good | | | -1 |
| 17 | 331_6 | PGC | PGC | Good | | | -1 |
| 18 | s1:0.1 | PGC | PGC | Bad | | | -1 |
| 19 | s1:0.12 | PGC | PGC | Bad | | | -1 |
| 20 | s2:0.5 | PGC | PGC | Bad | | | -1 |
| 21 | s2:0.4 | PGC | PGC | Bad | | | -1 |
| 22 | s2:0.35 | PGC | PGC | Bad | | | -1 |
| 23 | lm1:0.65 | PGC | PGC | Bad | | | -1 |
| 24 | lm1:0.68 | PGC | PGC | Bad | | | -1 |
| 25 | lm2:2 | PGC | PGC | Bad | | | -1 |
| 26 | lm2:1.75, s2:0.35 | PGC | PGC | Bad | | | -1 |
| 27 | lm1:0.78, s1:0.1 | PGC | PGC | Bad | | | -1 |

Sheet: X Matrix (155 variables, 27 observations, 69 (1.65%) missing)

ⓘ No primary var. ID

6. Ensure First Colum is Primary ID

| | Primary ID | Secondary ID | Secondary ID | Secondary ID | Secondary ID | Secondary ID |
|---|---|---|---|---|---|---|
| Primary ID | Lot_cycle | Process Area | Column Pack | Good/Bad | Bifurcation? | Severe Tailing? |
| 2 | | 1 | PA7 | 32 | Good | |
| 3 | | 2 | PA7 | 32 | Good | |
| 4 | | 3 | PA7 | 32 | Good | |
| 5 | | 4 | PA7 | 32 | Good | |
| 6 | | 5 | PA7 | 32 | Good | |
| 7 | | 6 | PA7 | 32 | Good | |
| 8 | | 1 | PA7 | 32 | Good | |
| 9 | | 2 | PA7 | 32 | Good | |
| 10 | | 3 | PA7 | 32 | Good | |
| 11 | | 4 | PA7 | 32 | Good | |
| 12 | | 5 | PA7 | 32 | Good | |
| 13 | | 6 | PA7 | 32 | Good | |
| 14 | 329_1 | PGC | PGC | Good | | |
| 15 | 329_6 | PGC | PGC | Good | | |
| 16 | 331_1 | PGC | PGC | Good | | |
| 17 | 331_6 | PGC | PGC | Good | | |
| 18 | s1:0.1 | PGC | PGC | Bad | | |
| 19 | s1:0.12 | PGC | PGC | Bad | | |
| 20 | s2:0.5 | PGC | PGC | Bad | | |
| 21 | s2:0.4 | PGC | PGC | Bad | | |
| 22 | s2:0.35 | PGC | PGC | Bad | | |
| 23 | tm1:0.65 | PGC | PGC | Bad | | |
| 24 | tm1:0.68 | PGC | PGC | Bad | | |
| 25 | tm2:2 | PGC | PGC | Bad | | |
| 26 | tm2:1.75, s2:0.35 | PGC | PGC | Bad | | |
| 27 | tm1:0.78, s1:0.1 | PGC | PGC | Bad | | |

Sheet: X Matrix (151 variables, 26 observations)

No issues

10. Check bottom of import window for "Issues section", check that it displays "No issues" Then click finish import

FIG.15B-1

10. Check bottom of import window for "Issues section". check that it displays "No issues" Then click finish import Cont. From FIG.15B-1

| | 7 | 8 | 9 | 10 | 11 | 12 | 13 | 14 | 15 |
|---|---|---|---|---|---|---|---|---|---|
| | 0 | 0.02 | 0.04 | 0.06 | 0.08 | 0.1 | 0.12 | 0.14 | 0.16 |
| | −1.02032 | −0.997782 | −0.997051 | −0.997075 | −0.997782 | −0.997808 | −0.997782 | −0.998423 | −0.998523 |
| | −1.01667 | −0.997811 | −0.997026 | −0.997114 | −0.997714 | −0.997714 | −0.997714 | −0.99782 | −0.998521 |
| | −1.01593 | −0.997783 | −0.996976 | −0.997783 | −0.997783 | −0.997783 | −0.997783 | −0.998522 | −0.998522 |
| | −1.01742 | −0.997045 | −0.997041 | −0.997034 | −0.997761 | −0.997781 | −0.997714 | −0.997781 | −0.998453 |
| | −1.01593 | −0.997758 | −0.997791 | −0.997791 | −0.997791 | −0.997791 | −0.998463 | −0.998463 | −0.998522 |
| | −1.01525 | −0.99785 | −0.997111 | −0.997111 | −0.997783 | −0.9978 | −0.99785 | −0.99785 | −0.998589 |
| | −1.02035 | −0.997844 | −0.997072 | −0.997844 | −0.997777 | −0.997777 | −0.99854 | −0.998518 | −0.998535 |
| | −1.01742 | −0.997781 | −0.997041 | −0.997781 | −0.997731 | −0.997728 | −0.997781 | −0.998453 | −0.998453 |
| | −1.01742 | −0.997041 | −0.997041 | −0.997041 | −0.997041 | −0.997714 | −0.997754 | −0.997714 | −0.997749 |
| | −1.01667 | −0.996975 | −0.997006 | −0.997042 | −0.997012 | −0.996977 | −0.997114 | −0.997114 | −0.997714 |
| | −1.01593 | −0.997065 | −0.996266 | −0.996976 | −0.996976 | −0.996976 | −0.996976 | −0.997786 | −0.997782 |
| | −1.01667 | −0.997042 | −0.997042 | −0.997042 | −0.997788 | −0.997799 | −0.997714 | −0.997751 | −0.998521 |
| | −1 | −1 | −1 | −1 | −1 | −1 | −1 | −1 | −1 |
| | −1 | −1 | −1 | −1 | −1 | −1 | −1 | −1 | −1 |
| | −1 | −1 | −1 | −1 | −1 | −1 | −1 | −1 | −1 |
| | −1 | −1 | −1 | −1 | −1 | −1 | −1 | −1 | −1 |
| | −1 | −1 | −1 | −1 | −1 | −1 | −1 | −1 | −0.999999 |
| | −1 | −1 | −1 | −1 | −1 | −1 | −1 | −1 | −1 |
| | −1 | −1 | −1 | −1 | −1 | −1 | −1 | −1 | −1 |
| | −1 | −1 | −1 | −1 | −1 | −1 | −1 | −1 | −1 |
| | −1 | −1 | −1 | −1 | −1 | −1 | −1 | −1 | −1 |
| | −1 | −1 | −1 | −1 | −1 | −1 | −1 | −1 | −1 |
| | −1 | −1 | −1 | −1 | −1 | −1 | −1 | −1 | −1 |

FIG.15B-2

11. Save and Name new Simca file. Name the file, select the location where the file will be saved, then click save 1. Select New
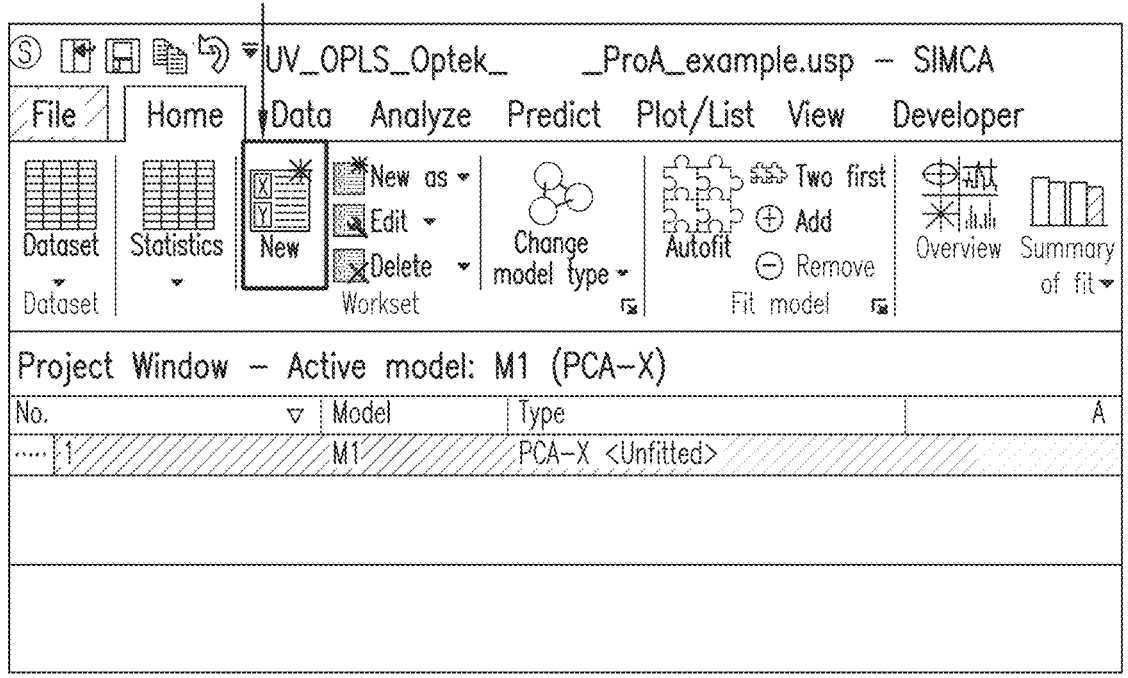
2. Select Observations, Then select the down arrow next to Class from obs ID and select Good/Bad
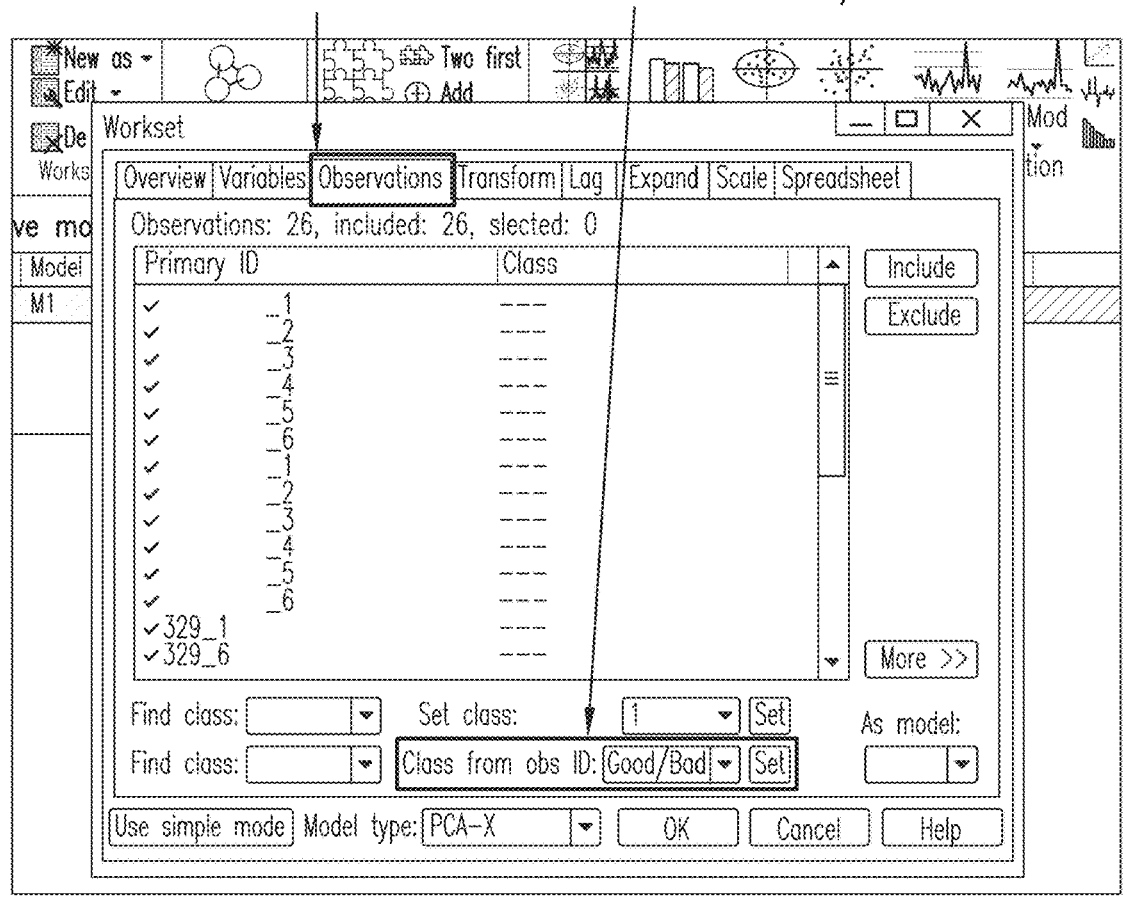
FIG.17

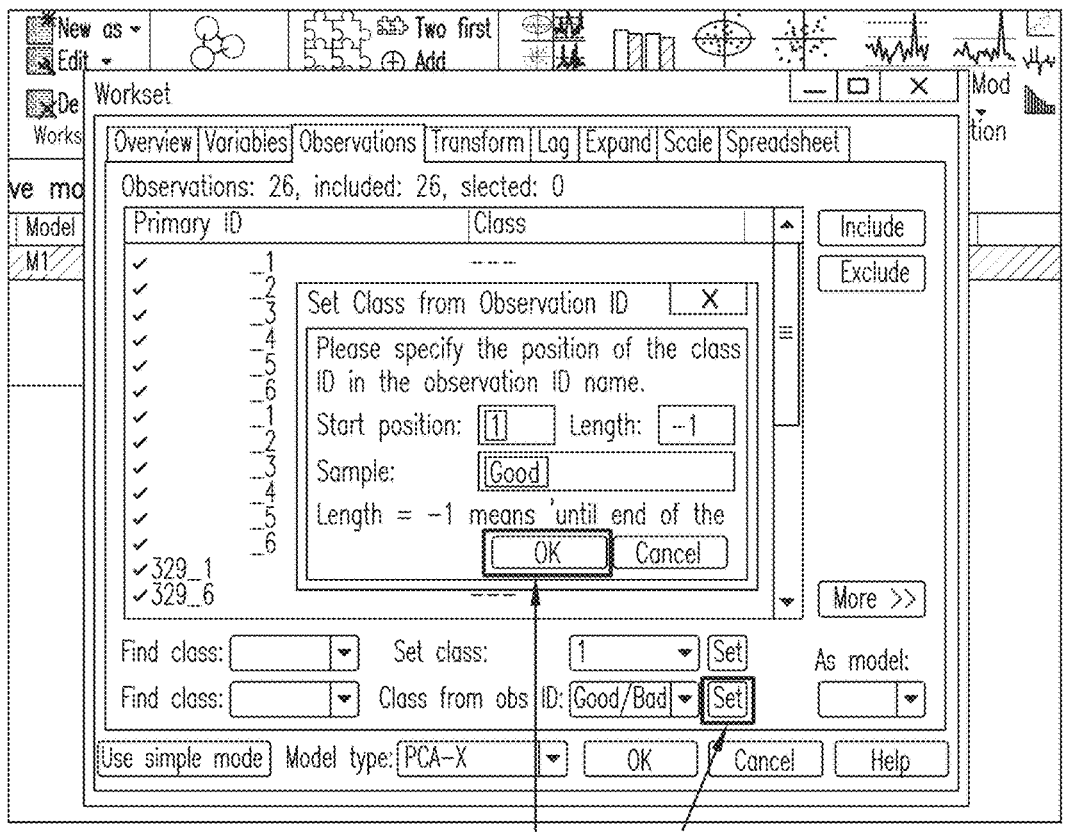
3. Select "set", then select "Ok" in the pop up window
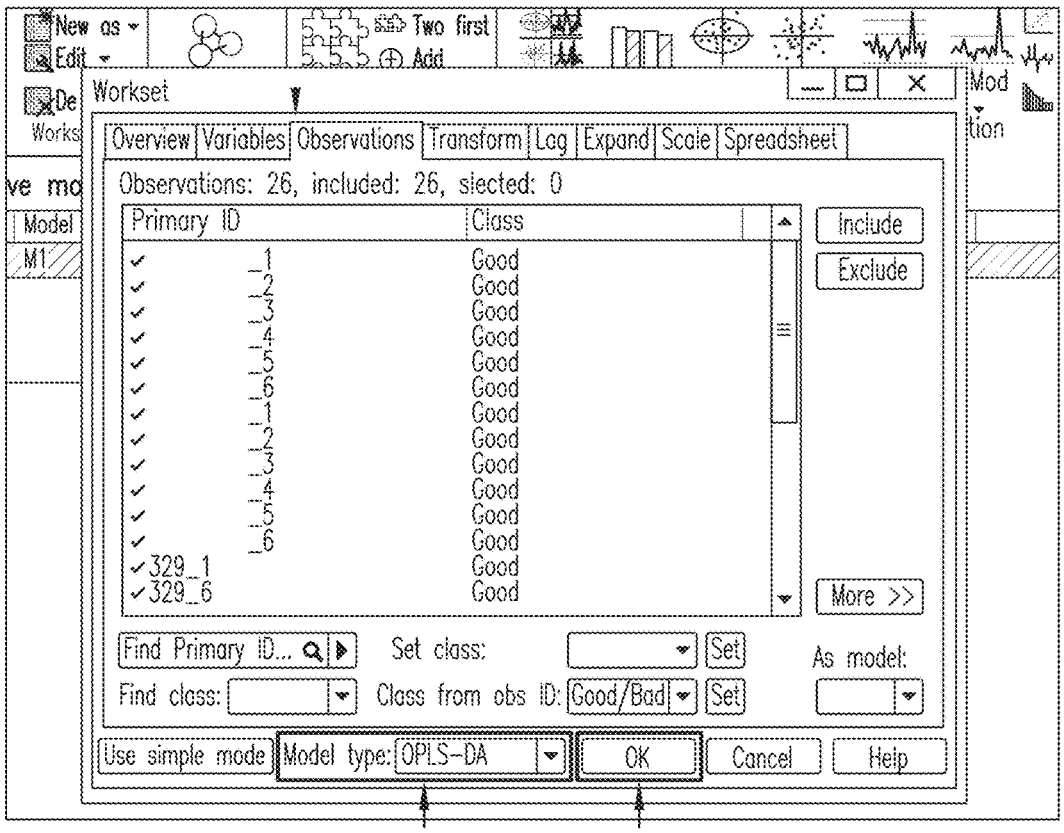
4. The model type displays as OPLS-DA. Select "Ok"
FIG.18

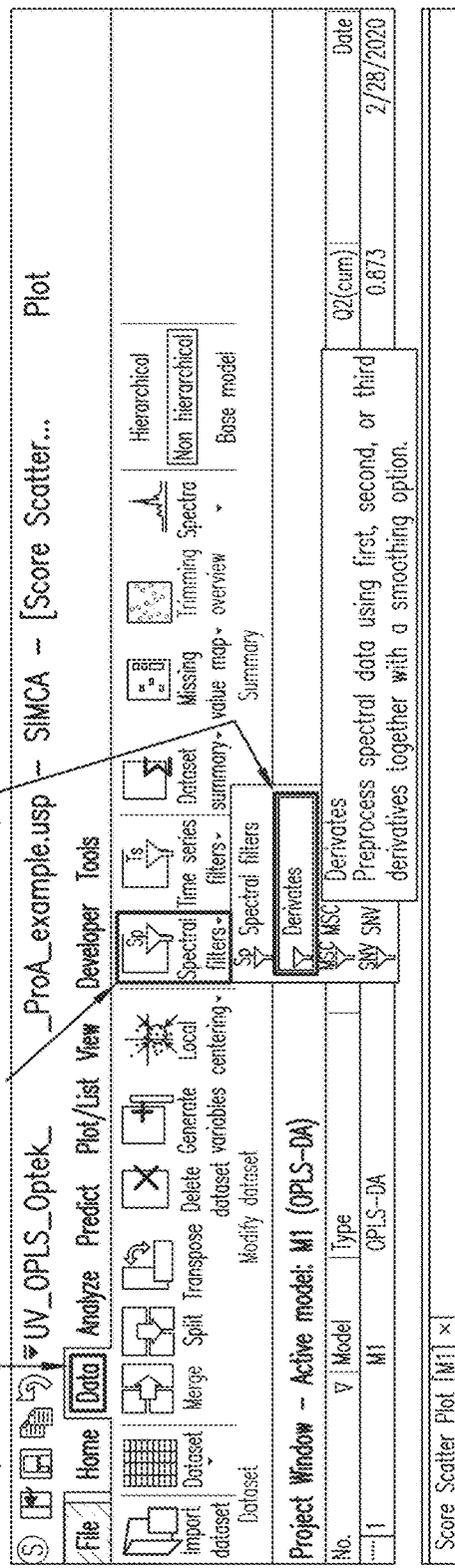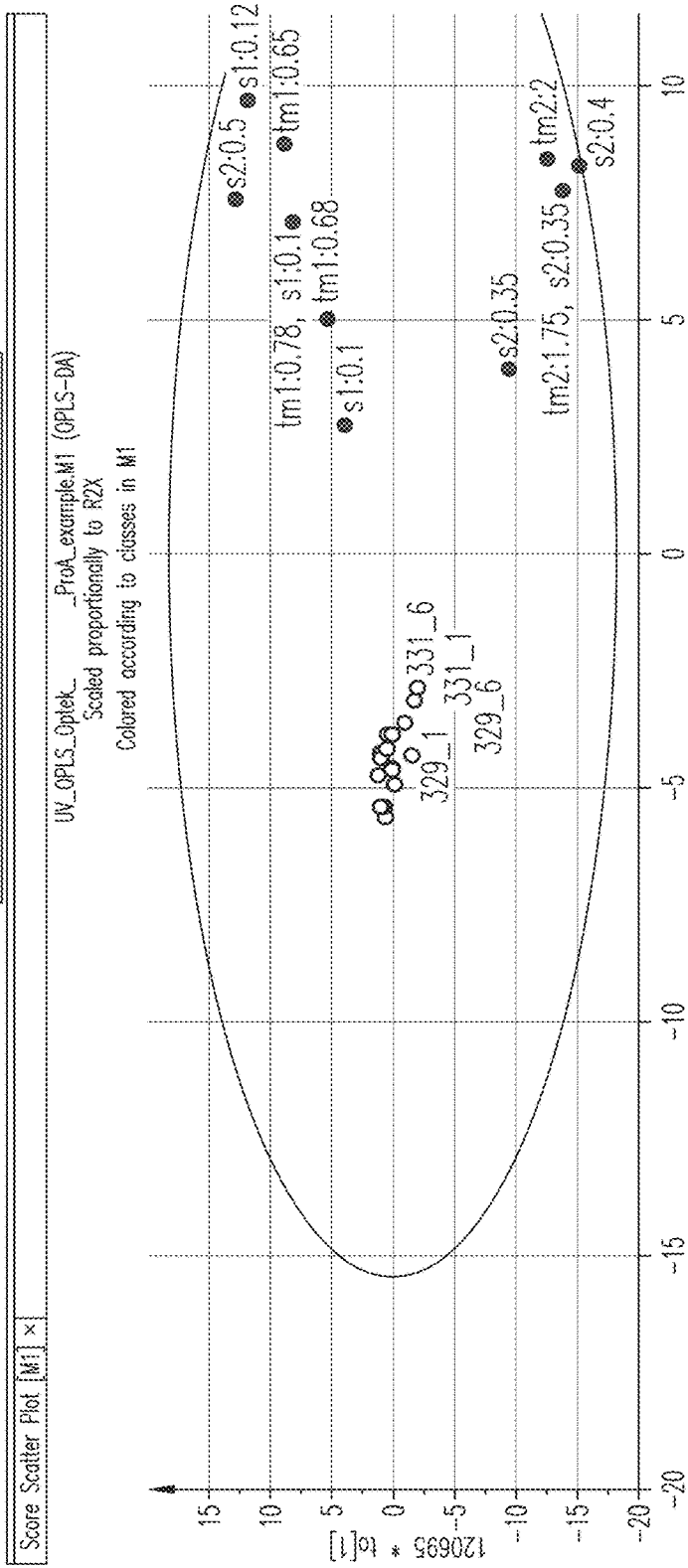
FIG. 21

3. The following window will show the data for each run and what the derivative looks like. Change the value for Points in each to 5 to reduce the level of smoothing. Then Click Next 4. Name the new dataset, then click Finish

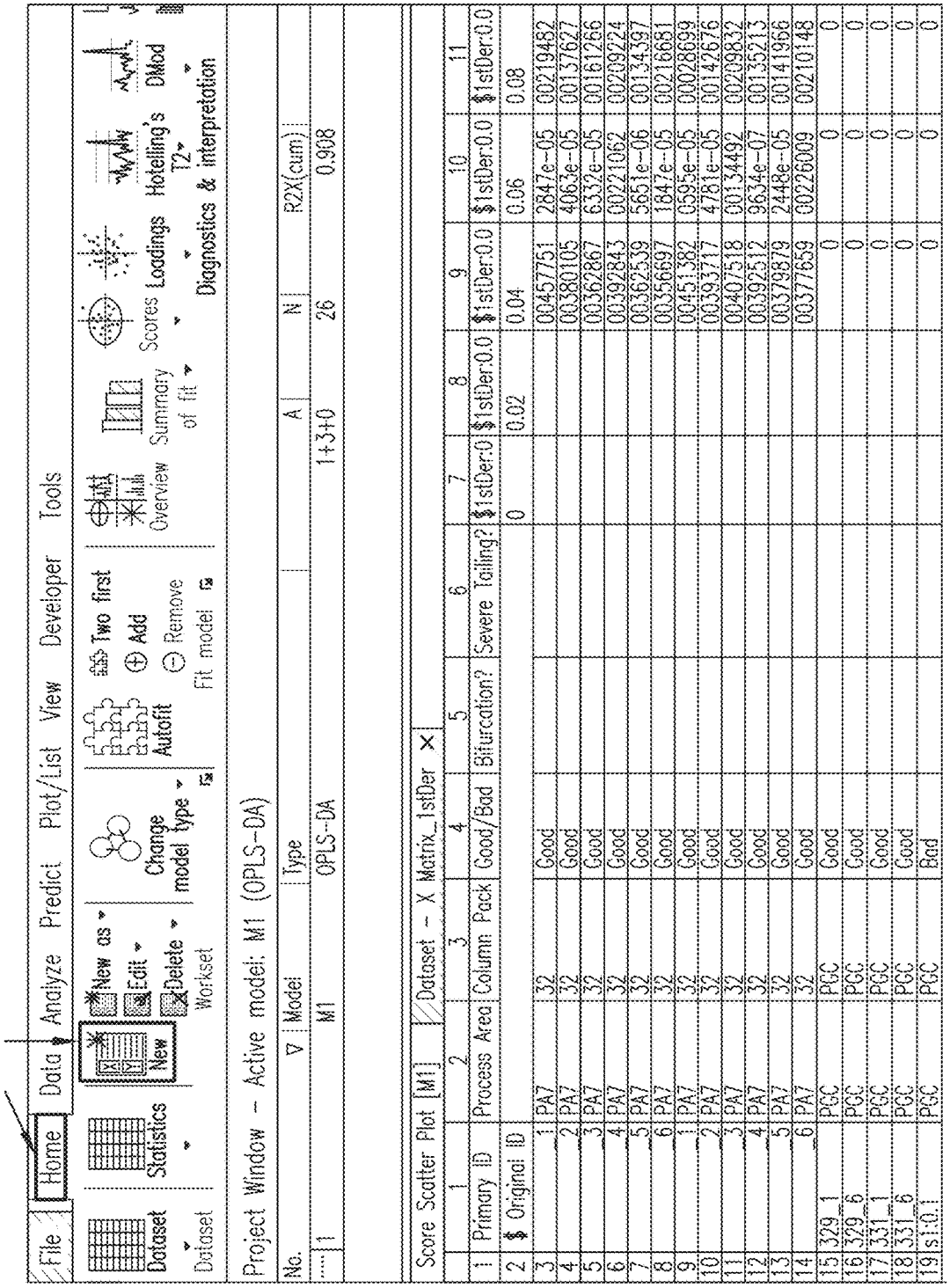

FIG.27B

8. The predicted scores plot will now show the points from the regular scores plot. The data is colored based on good/bad categorization. Since the new predicted runs were not classified as good or bad, they are colored in gray

ULTRAVIOLET MONITORING OF CHROMATOGRAPHY PERFORMANCE BY ORTHOGONAL PARTIAL LEAST SQUARES

CROSS-REFERENCE TO RELATED APPLICATION

This application claims the benefit under 35 USC § 119(e) of U.S. Provisional Application No. 63/009,835, filed Apr. 14, 2020, which is incorporated herein by reference in its entirety for all purposes.

FIELD OF THE INVENTION

The present invention pertains to chromatography, and in particular, to a method for ultraviolet (UV) monitoring of chromatography performance, such as by use of an orthogonal partial least squares (OPLS) model.

BACKGROUND

Chromatography is a separations technique used to purify proteins, including antibodies, in the biopharmaceutical industry. Chromatography uses a column packed with small particles (resin) which interacts with the product (desired protein) to separate it from impurities. Chromatograms are time based graphical records of a chromatographic separation to see how parameters such as UV absorbance, conductivity, and pH change over time during the chromatography run. The packed bed of resin in a chromatography column can deteriorate over time which can impact the efficiency of the chromatography separation and affect product quality.

It is beneficial to know when a chromatography column has begun to deteriorate so it can be repacked before the column deteriorates to the point where product quality can be impacted. Signs of column deterioration often appear in the UV absorbance trace in the chromatogram; however, features of deterioration can be difficult to visually identify. Chromatography-based protein analysis could benefit tremendously from improved methods of detecting and monitoring column deterioration, which can subsequently lead to improved protein purification, including improved antibody purification.

BRIEF SUMMARY OF THE INVENTION

In one aspect, the present invention provides a method of monitoring column chromatography performance, comprising: acquiring one or more chromatogram ultraviolet (UV) traces generated by a chromatography system during sample purification and/or separation; and analyzing the one or more acquired chromatogram UV traces with an orthogonal partial least squares (OPLS) model, thereby allowing detection of column deterioration prior to column failure and quantitative analysis of UV signal in the one or more chromatogram UV traces.

In some embodiments, the method further comprises creating an OPLS model.

In some embodiments creating the OPLS model comprises: selecting a process or unit operation of the OPLS model; collecting raw data for a UV trace of one or more column cycles/lots/runs for the selected process or unit operation; normalizing and aligning the collected raw data; optionally generating artificially created curves from normalized raw data; classifying and formatting data for importation into a multivariate tool; importing classified and formatted data into the multivariate tool to generate a training set; and generating the OPLS model.

In some embodiments, the method further comprises optimizing the generated OPLS model, validating and testing the optimized OPLS model.

In some embodiments, the process or unit operation is a chromatography unit operation for a single molecule.

In some embodiments, the process or unit operation is a protein affinity chromatography step for the single molecule.

In some embodiments, collecting raw data for a UV trace of one or more column cycles/lots/runs for the selected process or unit operation comprises collecting UV absorbance values at corresponding column volumes for the one or more cycles/lots/runs.

In some embodiments, normalizing and aligning the collected raw data comprises normalizing and aligning UV absorbance values and aligning column volumes.

In some embodiments, normalizing UV absorbance values comprises removing variation in magnitude differences in UV raw signal.

In some embodiments, optionally generating artificially created curves from normalized raw data comprises generating artificially created curves from normalized raw data when one or more unacceptable UV chromatogram traces are not available.

In some embodiments, the method further comprises providing a sample to the chromatography system prior to acquiring the one or more chromatogram ultraviolet (UV) traces generated by a chromatography system during sample purification and/or separation.

In some embodiments, the chromatography system is a liquid chromatography system.

In some embodiments, the sample comprises a protein.

In some embodiments, the protein is an antibody, a fusion protein, recombinant protein, or a combination thereof.

In some embodiments, the antibody is a monoclonal antibody.

In some embodiments, the monoclonal antibody is of isotype IgG1, IgG2, IgG3, IgG4, or mixed isotype.

Also disclosed is a method of creating an orthogonal partial least square (OPLS) model for UV monitoring of a chromatography column performance, comprising: selecting a process or unit operation of the OPLS model; collecting raw data for a ultraviolet (UV) chromatogram trace of one or more column cycles/lots/runs for the selected process or unit operation; normalizing and aligning the collected raw data; optionally generating artificially created curves from normalized raw data; classifying and formatting data for importation into a multivariate tool; importing classified and formatted data into the multivariate tool to generate a training set; and generating the OPLS model.

In some embodiments, the method further comprises optimizing the generated OPLS model, validating and testing the optimized OPLS model.

In some embodiments, the process or unit operation is a chromatography unit operation for a single molecule.

In some embodiments, the process or unit operation is a protein affinity chromatography step for the single molecule.

In some embodiments, collecting raw data for a UV trace of one or more column cycles/lots/runs for the selected process or unit operation comprises collecting UV absorbance values at corresponding column volumes for the one or more cycles/lots/runs.

In some embodiments, normalizing and aligning the collected raw data comprises normalizing and aligning UV absorbance values and aligning column volumes.

In some embodiments, normalizing UV absorbance values comprises removing variation in magnitude differences in UV raw signal.

In some embodiments, optionally generating artificially created curves from normalized raw data comprises generating artificially created curves from normalized raw data when one or more unacceptable UV chromatogram traces are not available.

In some embodiments, the method further comprises providing a sample to the chromatography system prior to acquiring the one or more chromatogram ultraviolet (UV) traces generated by a chromatography system during sample purification and/or separation.

In some embodiments, the chromatography system is a liquid chromatography system.

In some embodiments, the sample comprises a protein.

In some embodiments, the protein is an antibody, a fusion protein, recombinant protein, or a combination thereof.

In some embodiments, the antibody is a monoclonal antibody.

In some embodiments, the monoclonal antibody is of isotype IgG1, IgG2, IgG3, IgG4, or mixed isotype.

In embodiments, a non-transitory computer-readable storage medium with an executable program stored thereon for monitoring column chromatography performance, wherein the program instructs a microprocessor to perform the steps of: acquiring one or more chromatogram ultraviolet (UV) traces generated by a chromatography system during sample purification and/or separation; and analyzing the one or more acquired chromatogram UV traces with an orthogonal partial least squares (OPLS) model, thereby allowing detection of column deterioration prior to column failure and quantitative analysis of UV signal in the one or more chromatogram UV traces.

In some embodiments, the non-transitory computer-readable storage medium further comprises instructions for creating the OPLS model.

In some embodiments creating the OPLS model comprises: selecting a process or unit operation of the OPLS model; collecting raw data for a UV trace of one or more column cycles/lots/runs for the selected process or unit operation; normalizing and aligning the collected raw data; optionally generating artificially created curves from normalized raw data; classifying and formatting data for importation into a multivariate tool; importing classified and formatted data into the multivariate tool to generate a training set; and generating the OPLS model.

In some embodiments, the method further comprises optimizing the generated OPLS model, validating and testing the optimized OPLS model.

In some embodiments, the process or unit operation is a chromatography unit operation for a single molecule.

In some embodiments, the process or unit operation is a protein affinity chromatography step for the single molecule.

In some embodiments, collecting raw data for a UV trace of one or more column cycles/lots/runs for the selected process or unit operation comprises collecting UV absorbance values at corresponding column volumes for the one or more cycles/lots/runs.

In some embodiments, normalizing and aligning the collected raw data comprises normalizing and aligning UV absorbance values and aligning column volumes.

In some embodiments, normalizing UV absorbance values comprises removing variation in magnitude differences in UV raw signal.

In some embodiments, optionally generating artificially created curves from normalized raw data comprises generating artificially created curves from normalized raw data when one or more unacceptable UV chromatogram traces are not available.

In some embodiments, the method further comprises providing a sample to the chromatography system prior to acquiring the one or more chromatogram ultraviolet (UV) traces generated by a chromatography system during sample purification and/or separation.

In some embodiments, the chromatography system is a liquid chromatography system.

In some embodiments, the sample comprises a protein.

In some embodiments, the protein is an antibody, a fusion protein, recombinant protein, or a combination thereof.

In some embodiments, the antibody is a monoclonal antibody.

In some embodiments, the monoclonal antibody is of isotype IgG1, IgG2, IgG3, IgG4, or mixed isotype.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges and all values falling within such ranges are encompassed within the scope of the present disclosure. Each of the values discussed above or herein may be expressed with a variation of 1%, 5%, 10% or 20%. Other embodiments will become apparent from a review of the ensuing detailed description.

DESCRIPTION OF THE FIGURES

FIG. 1B shows a geometric interpretation of OPLS.

FIG. 4 shows exemplary exported raw data generated in accordance with embodiments disclosed herein.

FIG. 5-1 and FIG. 5-2 show exemplary normalization of data in accordance with embodiments disclosed herein.

Figure 7:
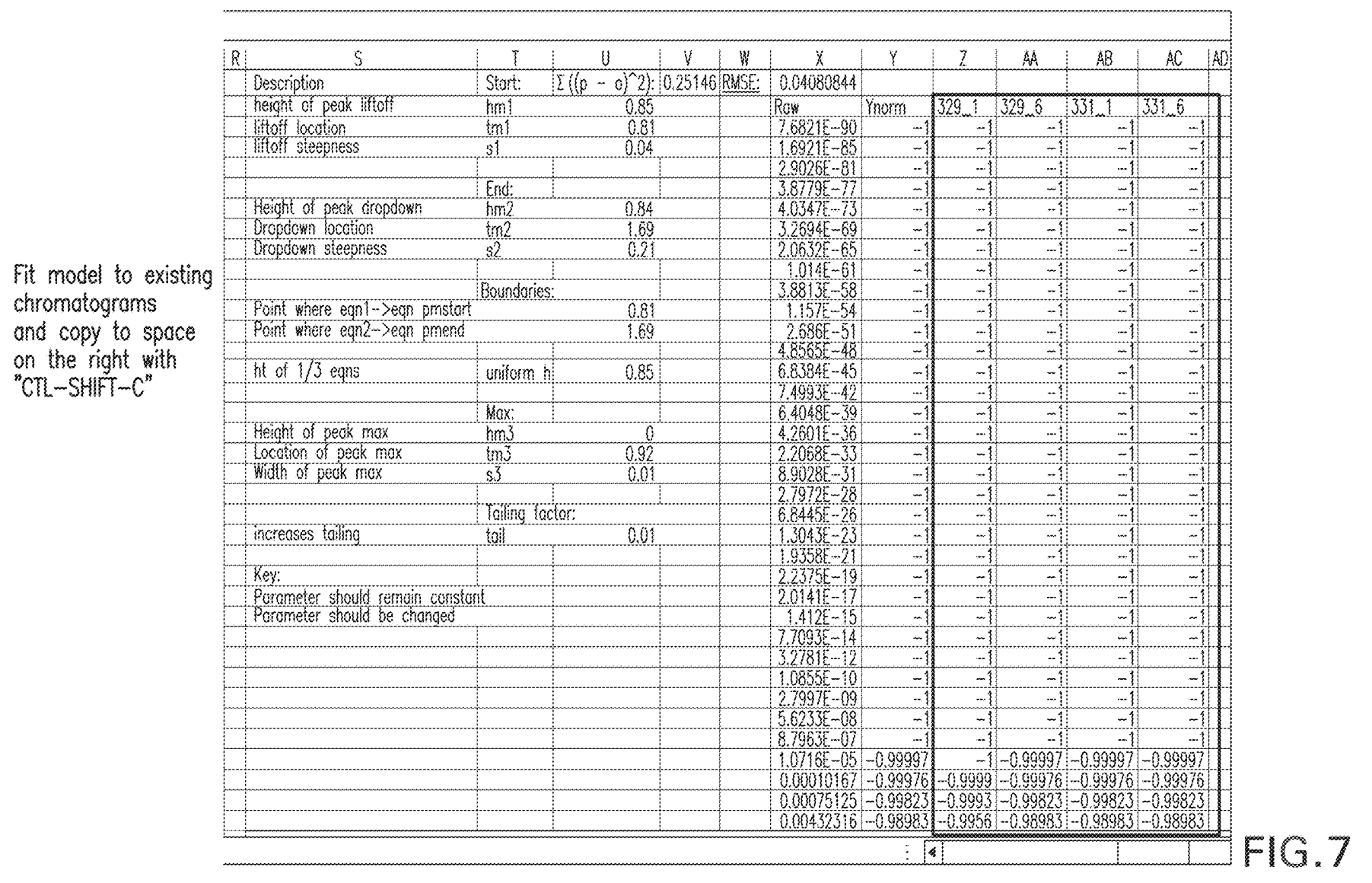

FIGS. 6-1, 6-2, 6-3, 7, 8, 9-1, 9-2, 10-1, and 10-2 show creating artificially generated curves from normalized data in accordance with embodiments disclosed herein.

FIG. 11-1 and FIG. 11-2 show exemplary classifying and formatting data for Simca import in accordance with embodiments disclosed herein.

Figure 14A:
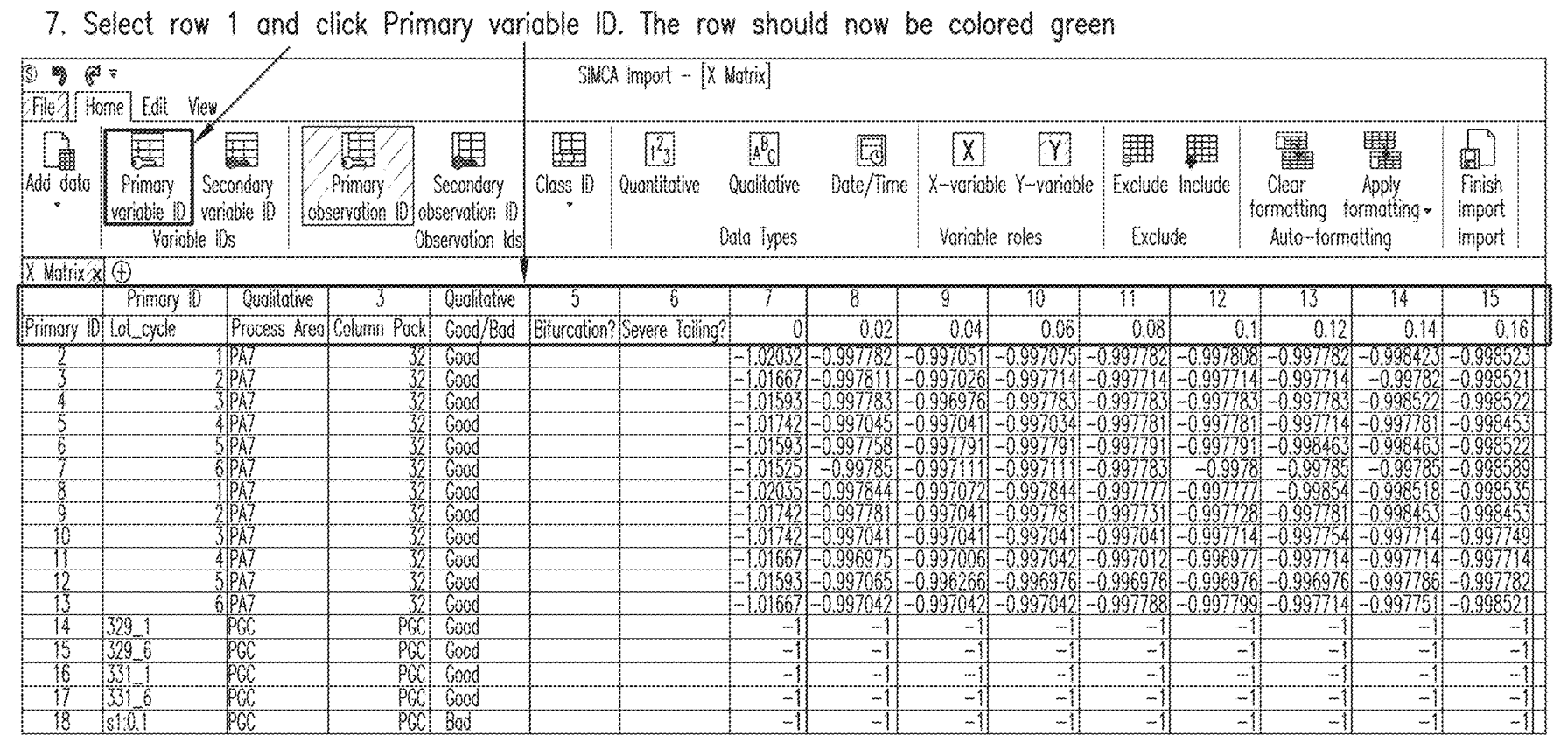
Figure 14B:
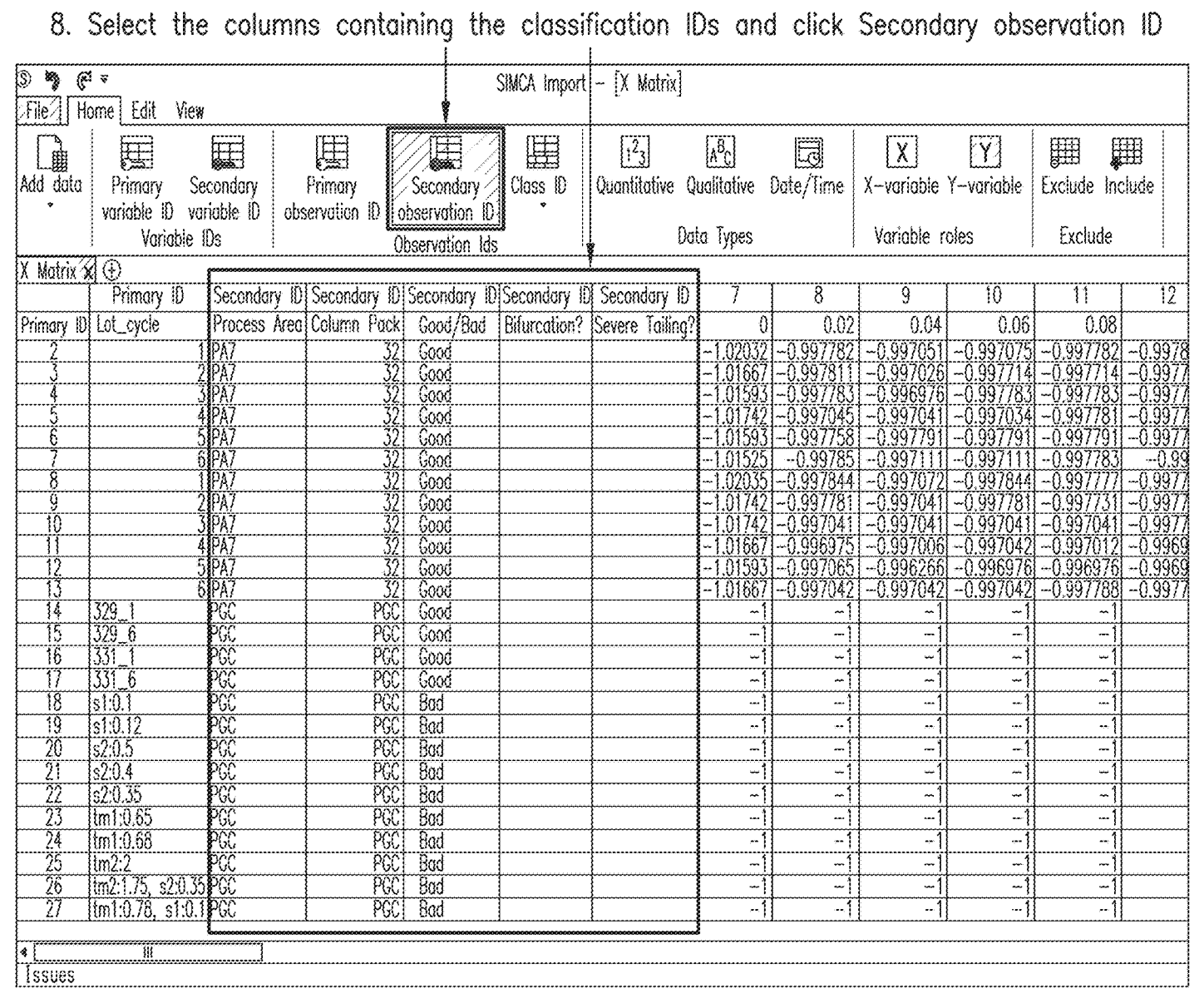

FIGS. 12A, 12B, 13A, 13B-1, 13B-2, 14A, 14B, 15A, 15B-1, 15B-2, and 16 show exemplary importing data into a multivariate tool in accordance with embodiments disclosed herein.

FIGS. 17, 18, 19, and 20 show exemplary generating an OPLS model in accordance with embodiments disclosed herein.

FIGS. 21, 22A, 22B, 23A, 23B, 24A, 24B, 25-1, and 25-2 show exemplary optimization of an OPLS model in accordance with embodiments disclosed herein.

Figure 27B:
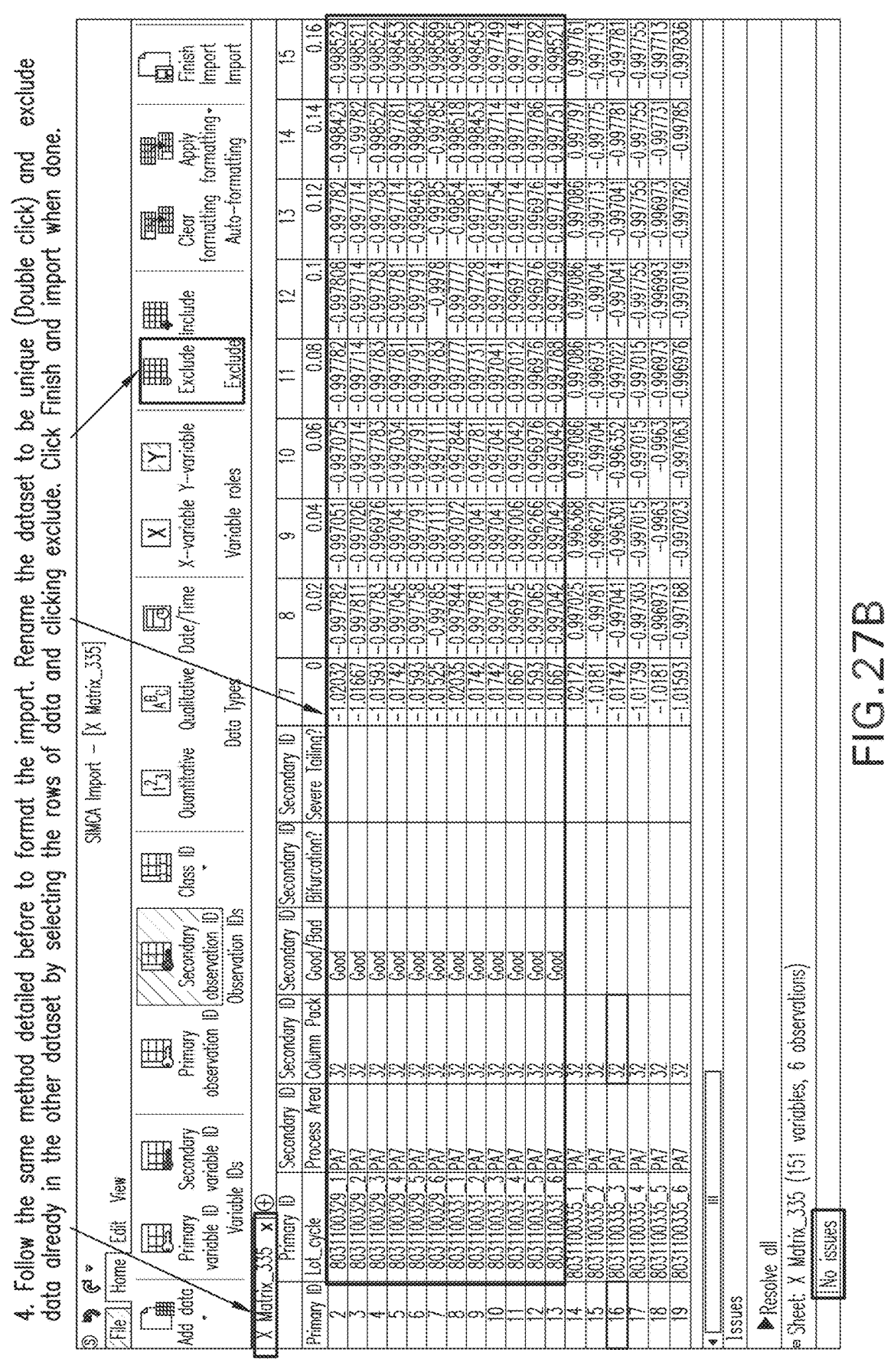

FIGS. 26A, 26B, 27A, 27B, 28, 29-1, 29-2, 30, 31-1, and 31-2 show exemplary application of the created OPLS model to classify new chromatograms as acceptable or unacceptable in accordance with embodiments disclosed herein.

FIGS. 32-1, 32-2, 33, 34, 35, 36, 37, 38A, 38B, 39A, 39B, and 40 show results generated by use of OPLS models in accordance with embodiments disclosed herein.

DETAILED DESCRIPTION OF THE INVENTION

Figure 1A:
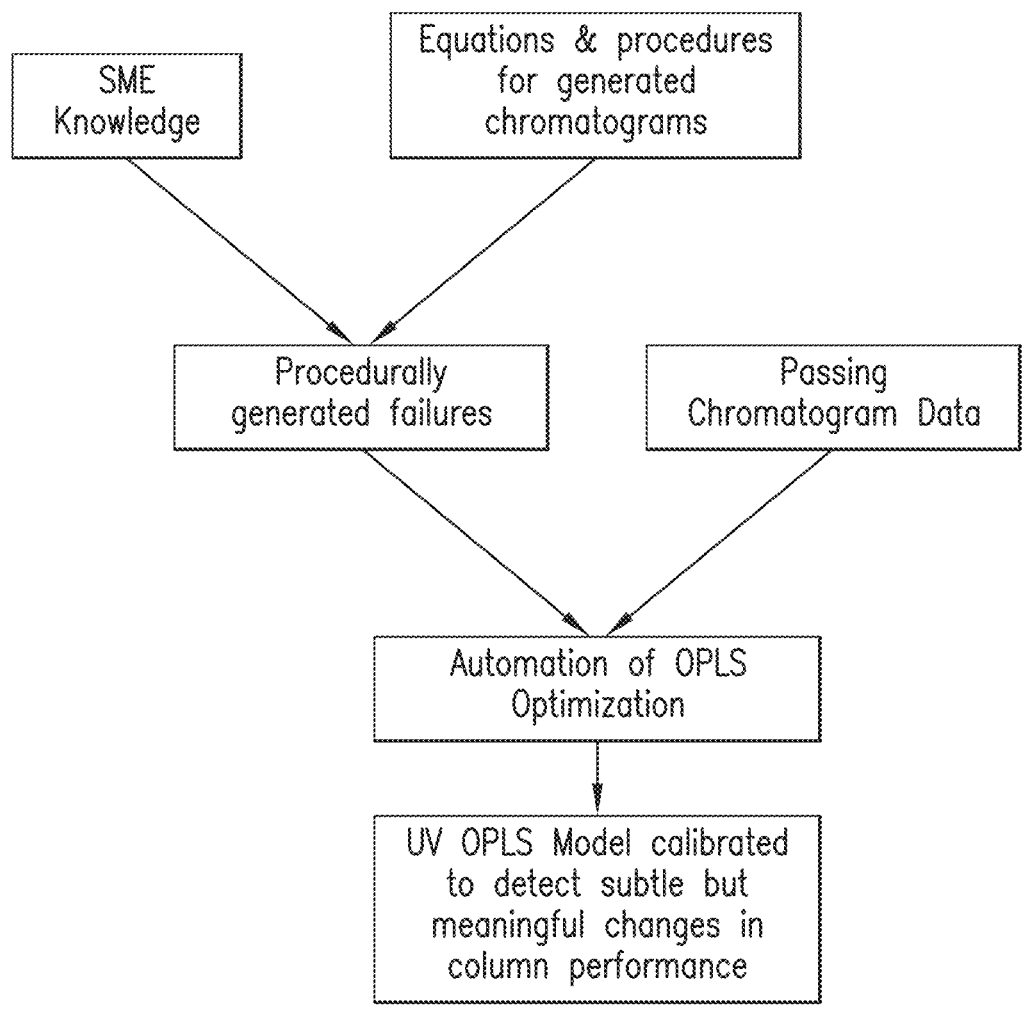
FIG. 1A shows an exemplary process workflow in accordance with embodiments disclosed herein.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Various operations may be described as multiple discrete operations in turn, in a manner that may be helpful in understanding embodiments; however, the order of description should not be construed to imply that these operations are order dependent.

The terms "coupled" and "connected," along with their derivatives, may be used. These terms are not intended as synonyms for each other. Rather, aspects, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but still cooperate or interact with each other.

As used herein, the terms "include," "includes," and "including," are meant to be non-limiting and are understood to mean "comprise," "comprises," and "comprising," respectively.

Although any methods and materials similar or equivalent to those described herein can be used in the practice or testing of the present invention, the preferred methods and materials are now described. All patents, applications and non-patent publications mentioned in this specification are incorporated herein by reference in their entireties.

ABBREVIATIONS USED HEREIN

CHO: Chinese Hamster Ovary
CV: Column Volumes
DDA: Data-Dependent Acquisition
EIC: Extracted Ion Chromatograph
HC: Heavy Chain
HIC: Hydrophobic Interaction Chromatography
HILIC: Hydrophilic Interaction Liquid Chromatography
HMW: High Molecular Weight
IgG: Immunoglobulin G
IPA: Isopropanol
LC: Light Chain
LMW: Low Molecular Weight
mAb: Monoclonal Antibody
MW: Molecular Weight
OPLS: Orthogonal Partial Least Square
PK: Pharmacokinetics
RMSE: Root Mean Square Error
RP-LC: Reversed Phase Liquid Chromatography
SME: Subject Matter Expert
SIM: Selected Ion Monitoring
UV: Ultraviolet

Definitions

As used herein, the term "protein" includes any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides' refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Biotechnol. Genet. Eng. Rev. (2012) 147-75). In some embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

Variant protein" or "protein variant", or "variant" as used herein can include a protein that differs from a target protein by virtue of at least one amino acid modification. Protein variant may refer to the protein itself, a composition comprising the protein, or the amino acid sequence that encodes it. Preferably, the protein variant has at least one amino acid modification compared to the parent protein, e.g. from about one to about ten amino acid modifications, and preferably from about one to about five amino acid modifications compared to the parent. The protein variant sequence herein will preferably possess at least about 80% homology with a parent protein sequence, and most preferably at least about 90% homology, more preferably at least about 95% homology. In some exemplary embodiments, the protein can be an antibody, a bispecific antibody, a multispecific antibody, antibody fragment, monoclonal antibody, or combinations thereof.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains,* 27(1) Dev. Comp. Immunol. 55-77 (2003); and M. Potter, *Structural correlates of immunoglobulin diversity,* 2(1) Surv. Immunol. Res. 27-42 (1983).

The term antibody also encompasses "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) 90 PNAS U.S.A. 6444-6448; and Poljak et al. (1994) 2 Structure 1121-1123).

Moreover, antibodies and antigen-binding fragments thereof can be obtained using standard recombinant DNA techniques commonly known in the art (see Sambrook et al., 1989). Methods for generating human antibodies in transgenic mice are also known in the art. For example, using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to a desired antigen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

As used herein, the term "impurity" can include any undesirable protein present in the biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S-S linked, oxidized, or altered conjugated forms (e.g., glycosylation, phosphorylation). Modified forms can also include any post-translational modification form. Aggregates include dimers and higher multiples of the desired product (Q6B Specifications: Test Procedures and Acceptance Criteria for Biotechnological/Biological Products, ICH August 1999, U.S. Dept. of Health and Humans Services).

The term "low molecular weight (LMW) protein drug impurity" includes but is not limited to precursors, degradation products, truncated species, proteolytic fragments including Fab fragments, Fc or heavy chain fragments, ligand or receptor fragments, H2L (2 heavy chains and 1 light chain), H2 (2 heavy chains), HL (1 heavy chain and 1 light chain), HC (1 heavy chain), and LC (1 light chain) species. A LMW protein drug impurity can be any variant which is an incomplete version of the protein product, such as one or more components of a multimeric protein. Protein drug impurity, drug impurity or product impurity are terms that may be used interchangeably throughout the specification. LMW drug or product impurities are generally considered molecular variants with properties such as activity, efficacy, and safety that may be different from those of the desired drug product.

Degradation of protein product is problematic during production of the protein drug product in cell culture systems. For example, proteolysis of a protein product may occur due to release of proteases in cell culture medium. Medium additives, such as soluble iron sources added to inhibit metalloproteases, or serine and cysteine proteases inhibitors, have been implemented in cell culture to prevent degradation (Clincke, M.-F., et al, BMC Proc. 2011, 5, P115). C-terminal fragments may be cleaved during production due to carboxyl peptidases in the cell culture (Dick, L W et al, Biotechnol Bioeng 2008; 100:1132-43).

The term "high molecular weight (HMW) protein drug impurity" includes but is not limited to mAb trimers and mAb dimers. HMW species can be divided into two groups: 1) monomer with extra light chains (H2L3 and H2L4 species) and 2) monomer plus Fab fragments complexes. In addition, after treatment with IdeS enzymatic digestion, different dimerized fragments (Fab2-Fab2, Fc-Fc and Fab2-Fc) are formed.

The term as used herein, "glycopeptide/glycoprotein" is a modified peptide/protein, during or after their synthesis, with covalently bonded carbohydrates or glycan. In certain embodiments, a glycopeptide is obtained from a monoclonal antibody, for example, from a protease digest of a monoclonal antibody.

The term as used herein, "glycan" is a compound comprising one or more of sugar units which commonly include glucose (Glc), galactose (Gal), mannose (Man), fucose (Fuc), N-acetylgalactosamine (GalNAc), N-acetylglucosamine (GlcNAc) and N-acetylneuraminic acid (NeuNAc) (Frank Kjeldsen, et al. Anal. Chem. 2003, 75, 2355-2361). The glycan moiety in glycoprotein, such as a monoclonal antibody, is an important character to identify its function or cellular location. For example, a specific monoclonal antibody is modified with specific glycan moiety.

The term "sample," as used herein, includes at least an analyte molecule, e.g., glycopeptide, such as obtained from a monoclonal antibody, that is subjected to manipulation in accordance with the methods of the invention, including, for example, separating, analyzing, extracting, concentrating or profiling.

The terms "analysis" or "analyzing," as used herein, are used interchangeably and refer to any of the various methods of separating, detecting, isolating, purifying, solubilizing, detecting and/or characterizing molecules of interest. Examples include, but are not limited to, chromatography, solid phase extraction, solid phase micro extraction, electrophoresis, mass spectrometry, e.g., liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The term "profiling," as used herein, refers to any of various methods of analysis which are used in combination to provide the content, composition, or characteristic ratio of compounds, such as proteins.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion. As used herein, the term "hydrolyzing agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of Streptococcus pyogenes (IdeS), chymotrypsin, pepsin, thermolysin, papain, pronase, and protease from Aspergillus Saitoi. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (J. Proteome Research 2013, 12, 1067-1077). One or a combination of hydrolyzing agents can cleave peptide bonds in a protein or polypeptide, in a sequence-specific manner, generating a predictable collection of shorter peptides.

Several approaches are available that can be used to digest a protein. One of the widely accepted methods for digestion of proteins in a sample involves the use of proteases. Many proteases are available and each of them has their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes—aspartic, glutamic, and metalloproteases, cysteine, serine, and threonine proteases, as classified on the mechanism of catalysis. The terms "protease" and "peptidase" are used interchangeably to refer to enzymes which hydrolyze peptide bonds. Proteases can also be classified into specific and non-specific proteases. As used herein, the term "specific protease" refers to a protease with an ability to cleave the peptide substrate at a specific amino acid side chain of a peptide. As used herein, the term "non-specific protease" refers to a protease with a reduced ability to cleave the peptide substrate at a specific amino acid side chain of a peptide. A cleavage preference may be determined based on the ratio of the number of a particular amino acid as the site of cleavage to the total number of cleaved amino acids in the protein sequences.

The protein can optionally be prepared before characterizing. In some exemplary embodiments, the protein preparation includes a step of protein digestion. In some specific exemplary embodiments, the protein preparation includes a step of protein digestion, wherein the protein digestion can be carried out using trypsin.

In some exemplary embodiments, the protein preparation can include a step for denaturing the protein, reducing the protein, buffering the protein, and/or desalting the sample, before the step of protein digestion. These steps can be accomplished in any suitable manner as desired.

As used herein, the term "chromatography" refers to a process technique for separating the components, or solutes, of a mixture on the basis of the relative amounts of each solute distributed between a moving fluid stream, called the mobile phase, and a contiguous stationary phase. The mobile phase may be either a liquid or a gas, while the stationary phase is either a solid or a liquid.

As used herein, the term "liquid chromatography" refers to a process in which a chemical mixture carried by a liquid can be separated into components as a result of differential distribution of the chemical entities as they flow around or over a stationary liquid or solid phase. Non-limiting examples of liquid chromatography include reverse phase liquid chromatography, ion-exchange chromatography, size exclusion chromatography, affinity chromatography, and hydrophobic chromatography.

As used herein, the term "multivariate tool" refers to a statistical tool that uses multiple variables to forecast outcomes. A multivariate tool can allow data to be explored, analyzed and/or interpreted. The tool can facilitate data diving by revealing trends and clusters, analyze process variations, identify parameters and/or predict final product quality. In some examples, a multivariate tool is one that is commercially available, such as SIMCA (umetrics, Umea, Sweden).

As used herein, the term "protein sequence coverage" refers to the percentage of the protein sequence covered by identified peptides. The percent coverage can be calculated by dividing the number of amino acids in all found peptides by the total number of amino acids in the entire protein sequence.

As used herein, the term "database" refers to bioinformatic tools which provide the possibility of searching the uninterpreted MS-MS spectra against all possible sequences in the database(s). Non-limiting examples of such tools are Mascot (www.matrixscience.com), Spectrum Mill (www.chem.agilent.com), PLGS (www.waters.com), PEAKS (www.bioinformaticssolutions.com), Proteinpilot (download.appliedbiosystems.com//proteinpilot), Phenyx (http://www.phenyx-ms.com), Sorcerer (www.sagenresearch.com), OMSSA (www.pubchem.ncbi.nlm.nih.gov/omssa/), X!Tandem (www.thegpm.org/TANDEM/), Protein Prospector (www.http://prospector.ucsf.edu/prospector/mshome.htm), Byonic (www.proteinmetrics.com/products/byonic) or Sequest (fields.scripps.edu/sequest).

General Description

From the foregoing, it will be appreciated that a need exists for improved methods and systems to improve protein purification, including antibody purification. The disclosed invention meets that need. Disclosed herein are methods utilizing OPLS modelling including examples of acceptable (no deterioration) and unacceptable (deterioration) chromatogram UV traces, such as UV, infrared (IR) or Ramen traces, to provide early detection of column failures and quantitative analysis of the UV signal in the chromatogram. In some embodiments, the methods utilize UV OPLS modeling. The disclosed methods combine process knowledge gained by subject matter experts (SMEs) with equations and procedures to create chromatograms to create comprehensive data sets ranging from robust to acceptable to incremental failures to catastrophic (see FIG. 1A). The disclosed methods utilize OPLS to address many challenges such as automation and comprehensive data assessment which was not previously possible. The disclosed methods achieve process monitoring through use of a multivariate tool (e.g., SIMCA) for predicting column failures. The disclosed OPLS models can be built without historical column failures and can be automated (such as by utilizing Python scripting) eliminating the manual process to perform overlays and analysis. Procedurally generated operation failures by use of mathematical equations and protocols overcome the weakness of limited historical data sets not containing failures. The disclosed methods are able to provide quantitative measurement of the chromatogram and column performance and allow for dynamic identification of variation. Thus, the disclosed methods ensure process consistency and robustness as well as consistent performance of equipment while eliminating disadvantages associated with current methods.

Figure 1C:
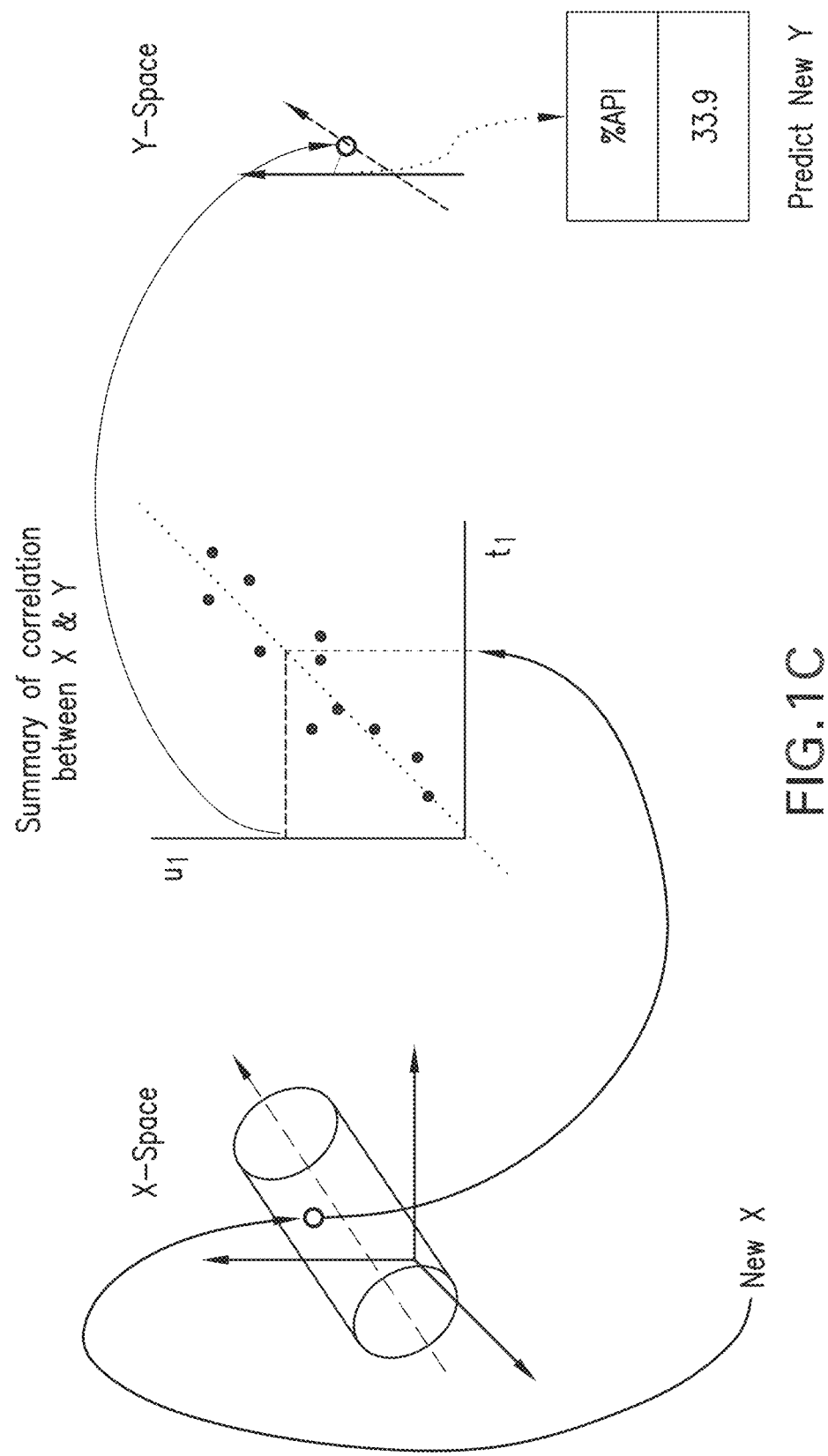
FIG. 1C shows a schematic illustrating OPLS predictions.

In embodiments, the disclosed methods utilize OPLS. OPLS regression analyzes relationships between two blocks of data by regression extensions of Principle Component Analysis (PCA). For example, a dataspace for X and Y matrix is constructed. A first component fits a line in the X and Y space so that the correlation between the X and Y projection is maximized. A second component is orthogonal to the first component in the X space. The first component is predictive and maximizes covariance between X and Y while the second component and onwards are orthogonal and represent structured variation in X that is not related to Y (FIG. 1B). OPLS-DA is a model where qualitative categorical variables (e.g., good/satisfactory or bad/unsatisfactory) are assigned quantitative values so that an OPLS model can be constructed. FIG. 1C shows a schematic illustrating OPLS predictions.

In embodiments, a method of monitoring column chromatography performance, comprises acquiring one or more chromatogram ultraviolet (UV) traces generated by a chromatography system during sample purification and/or separation; and analyzing the one or more chromatogram UV traces with an OPLS model, thereby allowing detection of column deterioration prior to column failure and quantitative analysis of UV signal in the one or more chromatogram UV traces.

Figure 1D:
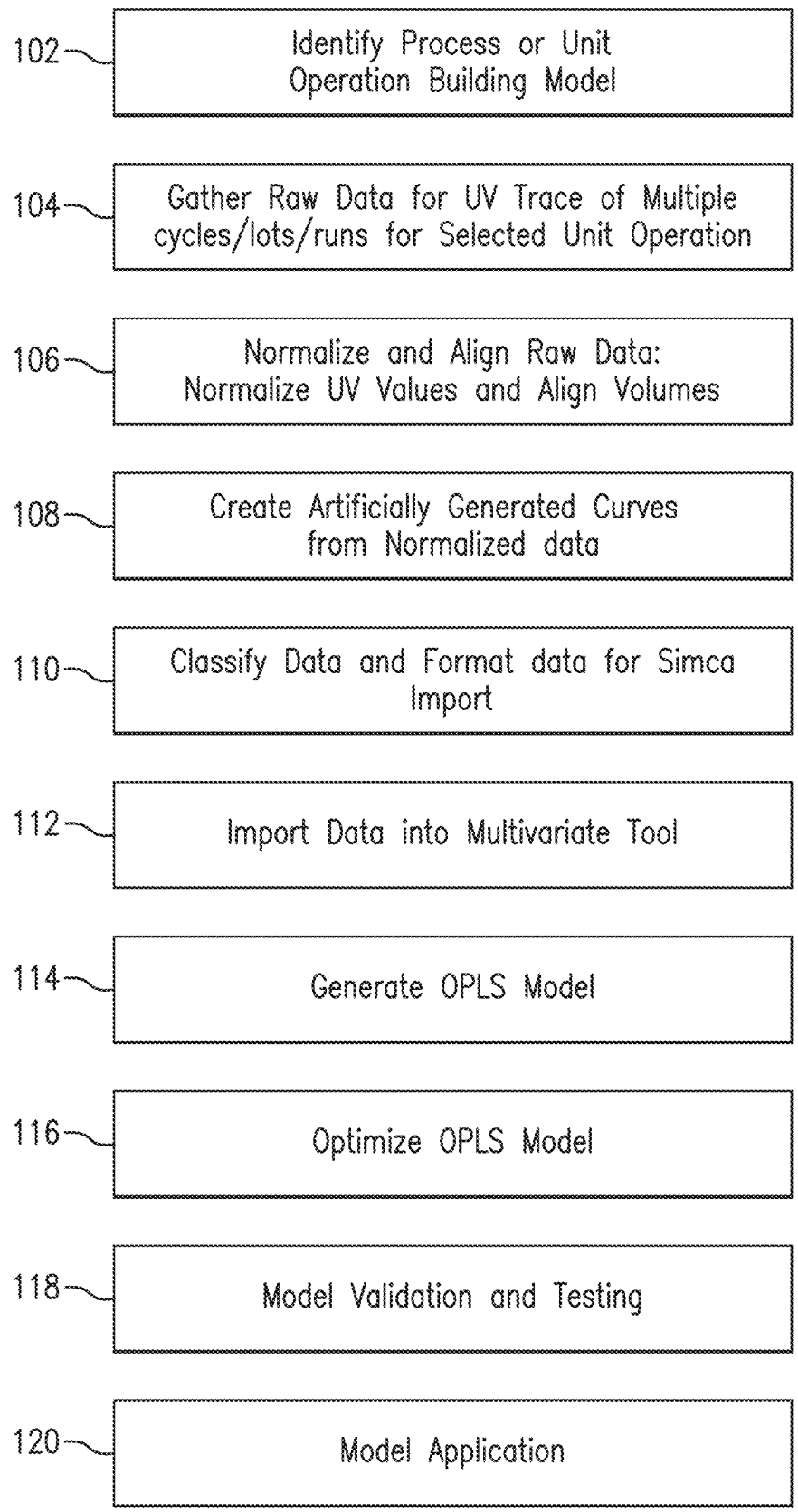
FIG. 1D shows a flow-chart illustrating an exemplary method of creating a UV OPLS model.
Figure 2:
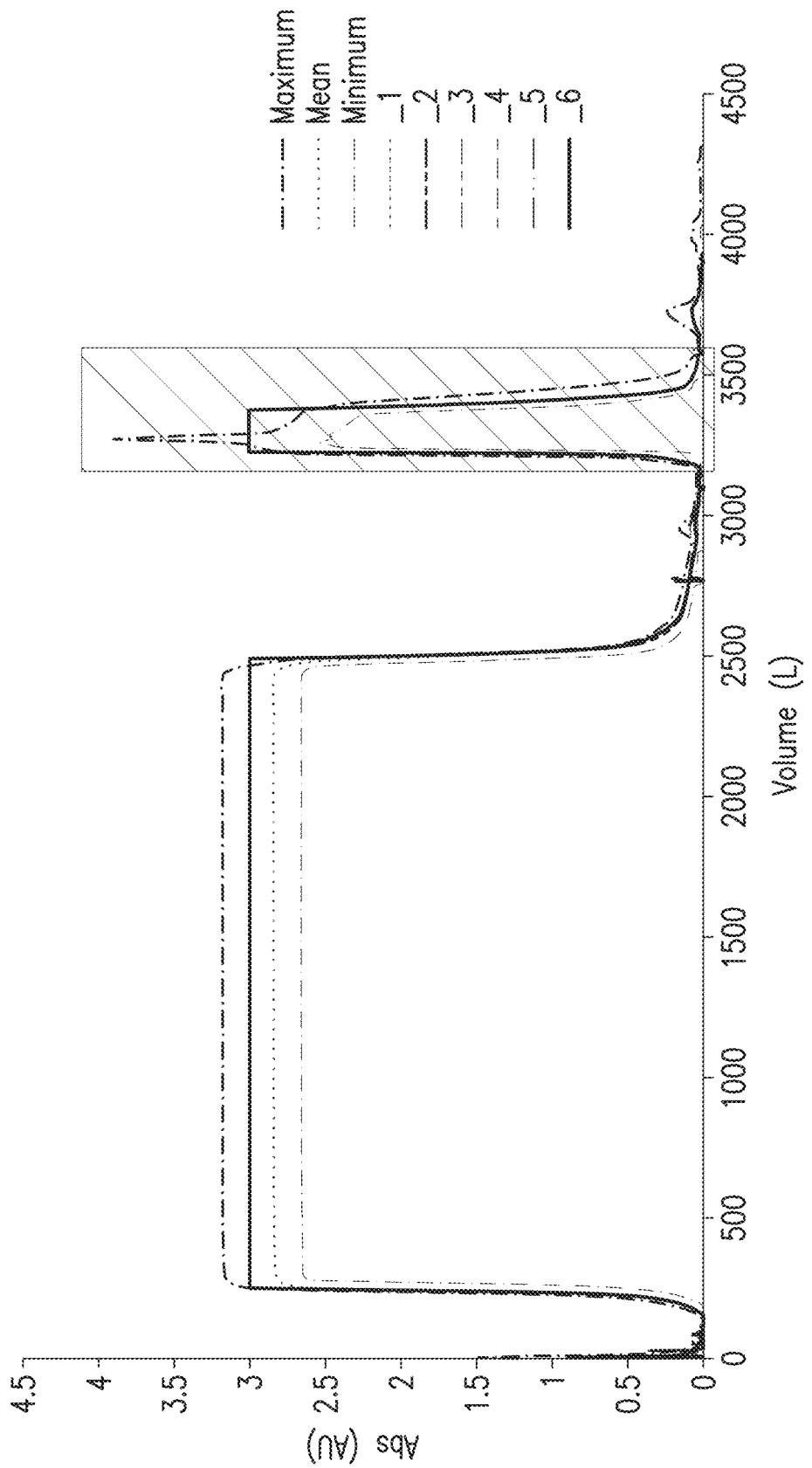
FIG. 2 shows an exemplary bind-elute chromatogram with the elution block highlighted.
Figure 3:
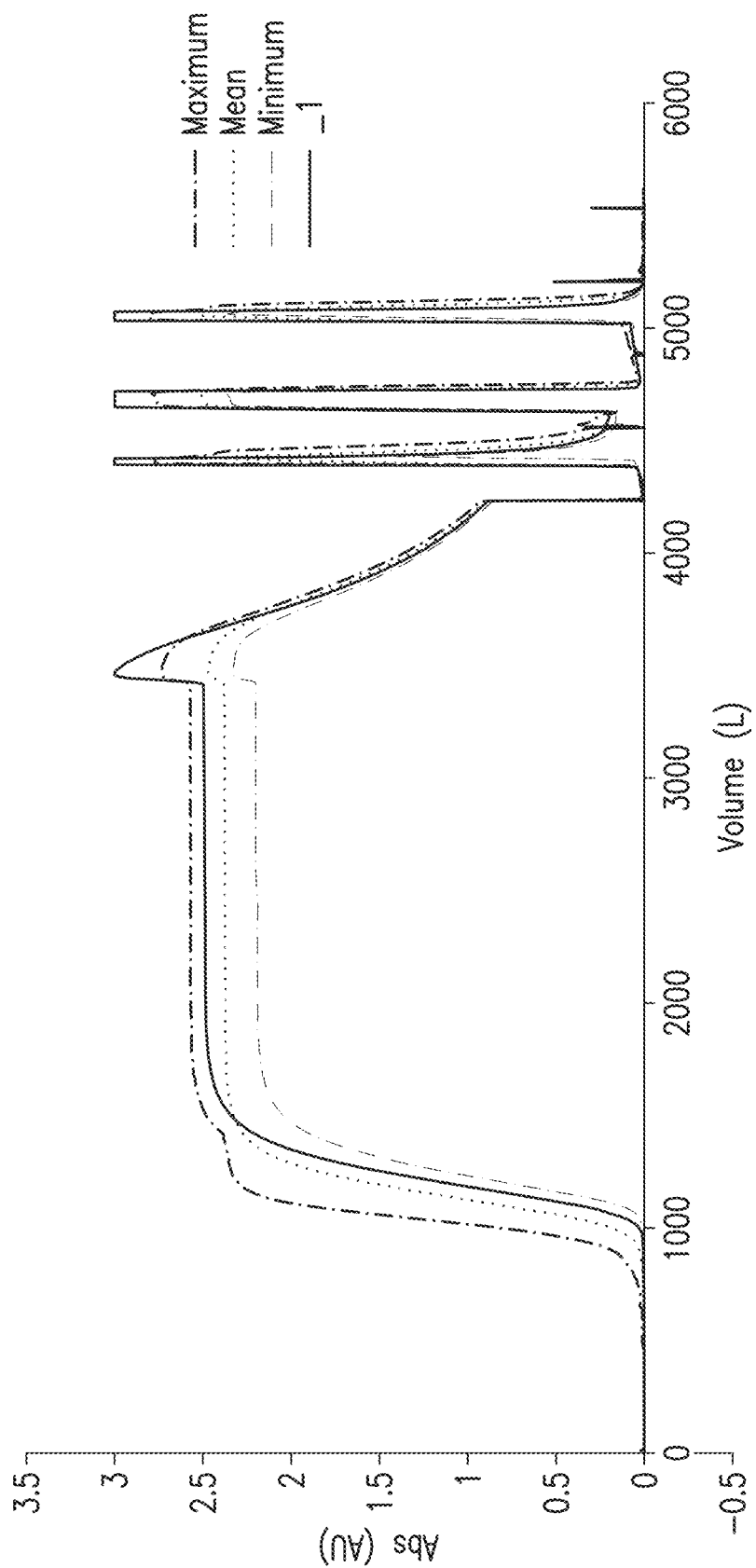
FIG. 3 shows an exemplary flow-through chromatogram with UV liftoff highlighted.
Figures 2, 6:
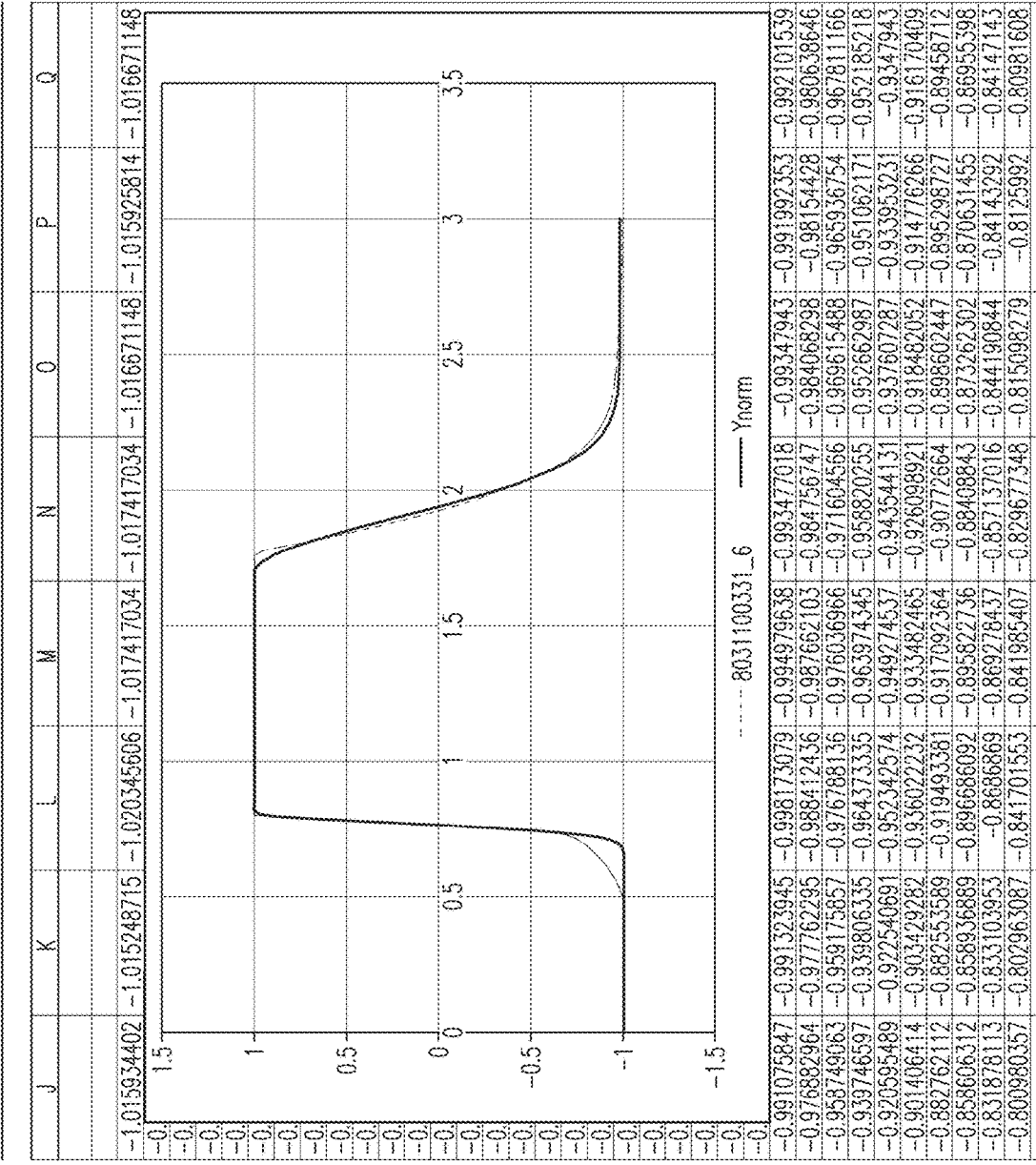

In embodiments, the method of monitoring column chromatography performance, includes creating a UV OPLS model. FIG. 1D provides a flow chart illustrating an exemplary protocol for creating a UV OPLS model. As illustrated in FIG. 1D, creating a UV OPLS model, includes step 102, identifying a process or unit operation the UV OPLS model is being built. In some embodiments, this is a particular chromatography unit operation for a certain product/molecule, for example, a protein affinity, ion exchange, hydrophobic interaction, or size exclusion chromatography step in either bind and elute or flow through design for a specific molecule. In embodiments, at least a portion of the UV signal in the chromatogram is fed into the model. Some portions of the chromatogram are not helpful for determining column integrity. For example, at least one block or section of the chromatogram is used. In some embodiments, if the unit operation column modality is bind and elute, then the elution block is used for analysis (e.g., where the bound product elutes off the column). FIG. 2 provides an example of a bind-elute chromatogram with elution block highlighted. In some embodiments, if the unit operation column modality is flow through, then the point where collection starts during the liftoff of the UV signal will be analyzed. FIG. 3 provides an example of a flow-through chromatogram with UV liftoff highlighted.

The method illustrated in FIG. 1D for creating a UV OPLS model further includes step 200, gathering raw data for a UV trace. In some embodiments, gathering raw data for the UV trace includes gathering raw data of multiple cycles, lots, and/or runs for the selected unit operation, for example UV absorbance values at corresponding volumes. For example, raw data for UV and logbook from the chromatography software (e.g., Unicorn) is exported, such as into an electronic storage file (e.g., Microsoft Excel file). The logbook is a tracker that identifies what events occurred at what volume during the chromatogram and identifies where to pull the block of data to input into the model (e.g., the elution block). The process can then be repeated for each run/cycle of the chromatography step. In embodiments, the run/cycle of raw data is stored, such as in a separate file (e.g., separate Microsoft Excel files) as shown in FIG. 4.

In embodiments, the exemplary method includes step 106, normalizing and aligning raw data, such as normalizing UV values and aligning volumes. For example, the data is normalized to remove any variation in magnitude differences (from UV meter functionality) in the raw signal. In embodiments, the raw UV and logbook data imported, data is normalized and formatted for import into a multivariate tool (e.g., SIMCA), such as by use of a macro. In embodiments, the steps performed by a macro can include:
1. Macro first prompts to select what files the macro will run on (e.g., what runs will be fed in to build the model);
2. Next, the macro finds the section of the chromatogram that will be analyzed by the model (e.g., the Elution block);
3. The macro finds the maximum and minimum UV values and normalizes the UV values from −1 to 1;
4. The macro normalizes the volume in terms of Column Volumes (CVs);
5. The macro pulls the normalized UV data at a specified CV interval so that all the UV data is aligned (e.g., pull UV signal value every 0.02 CVs in the Elution block);
6. The macro pastes the normalized data into a table that is formatted for Simca import; and
7. Macro repeats steps 2-6 if more than one run is selected.

Figures 1, 9:
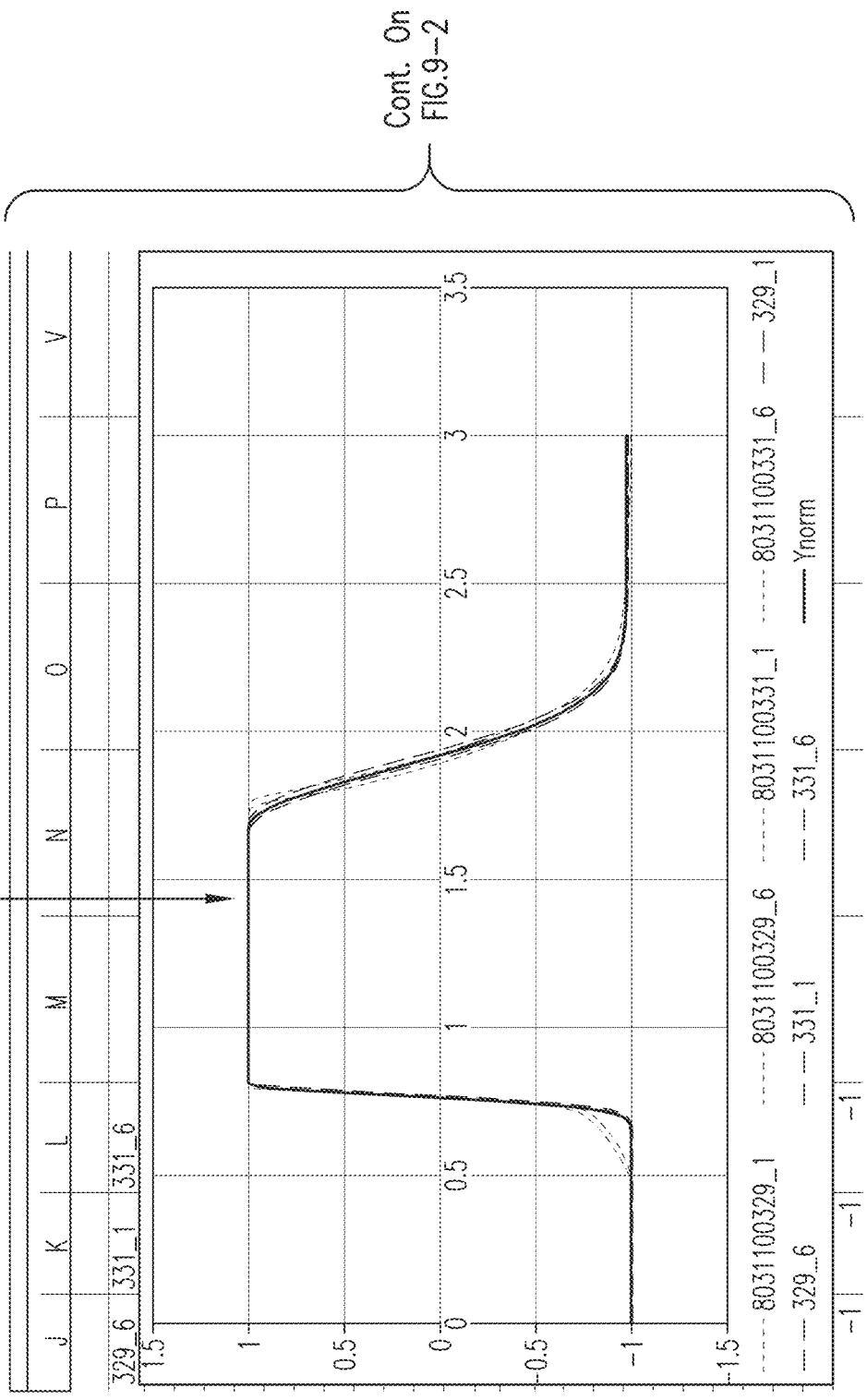
Figures 1, 10:
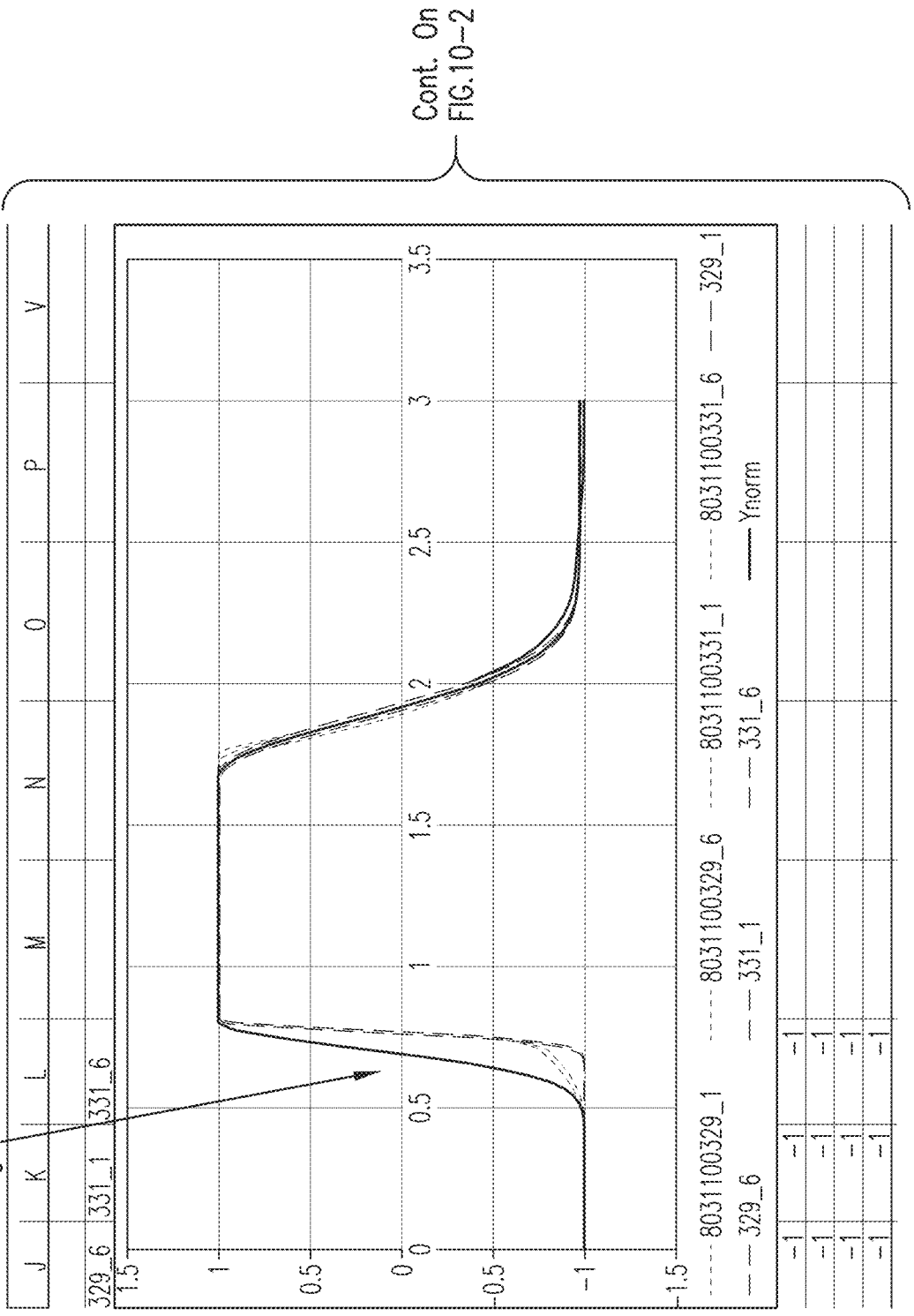
Figure 13A:
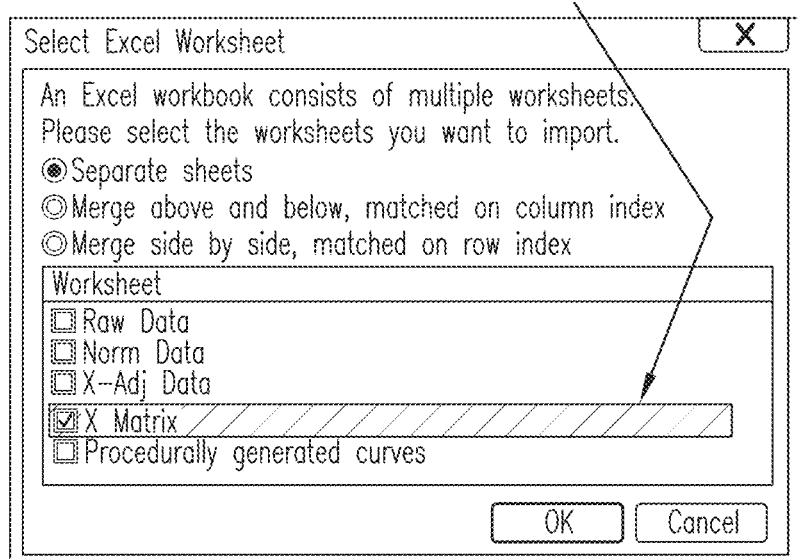
Figures 2, 13B:
Figure 16:
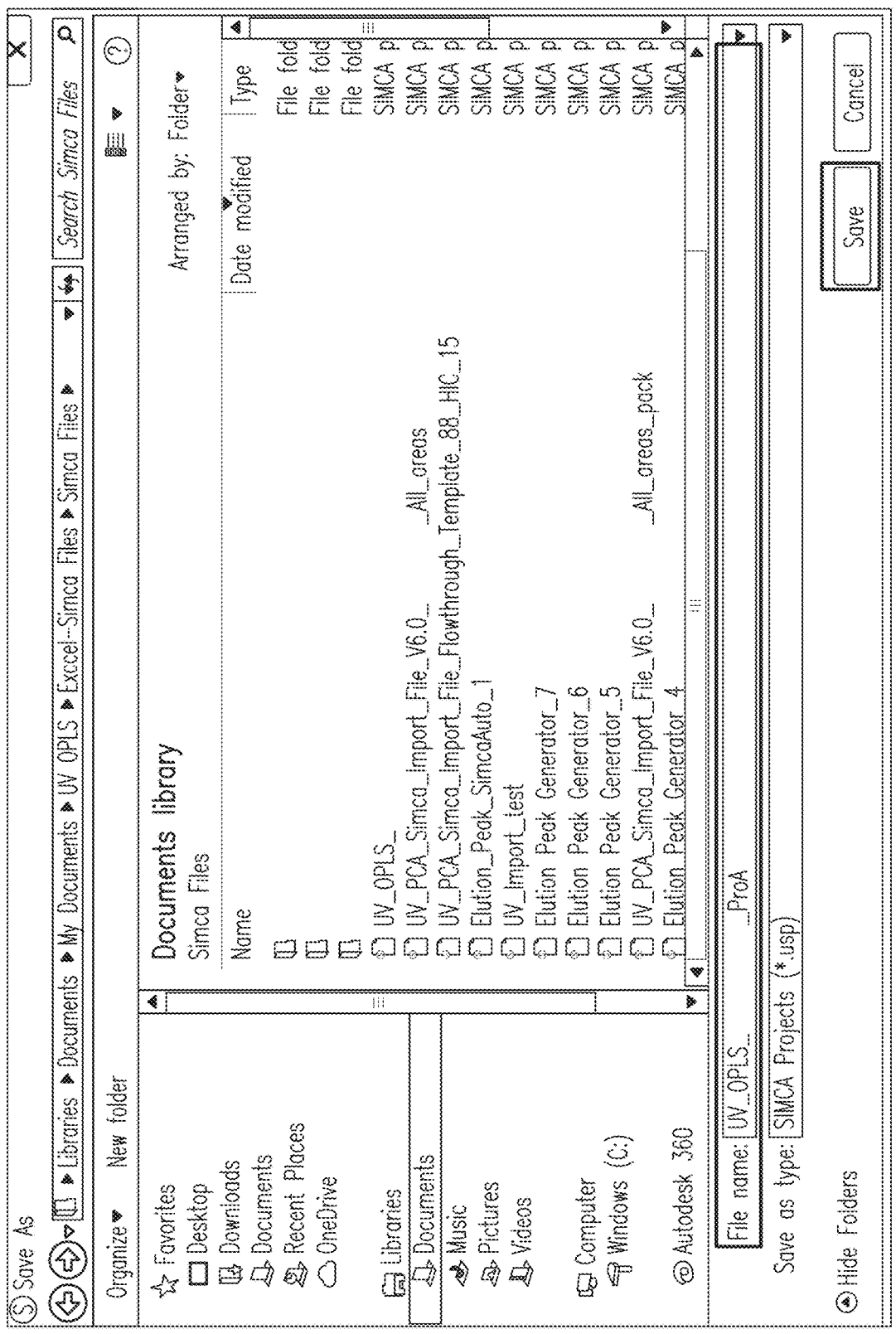
Figure 19:
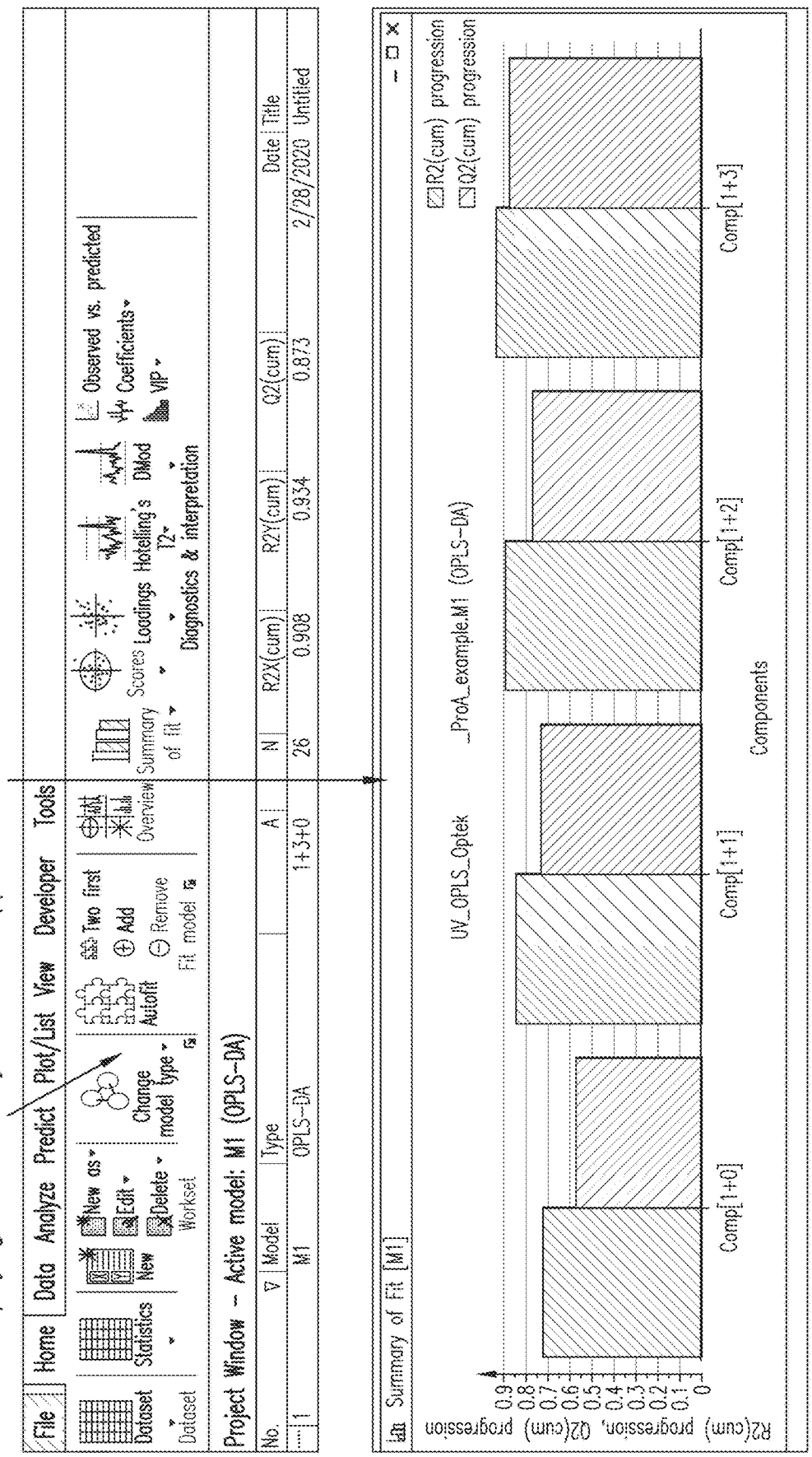
Figure 20:
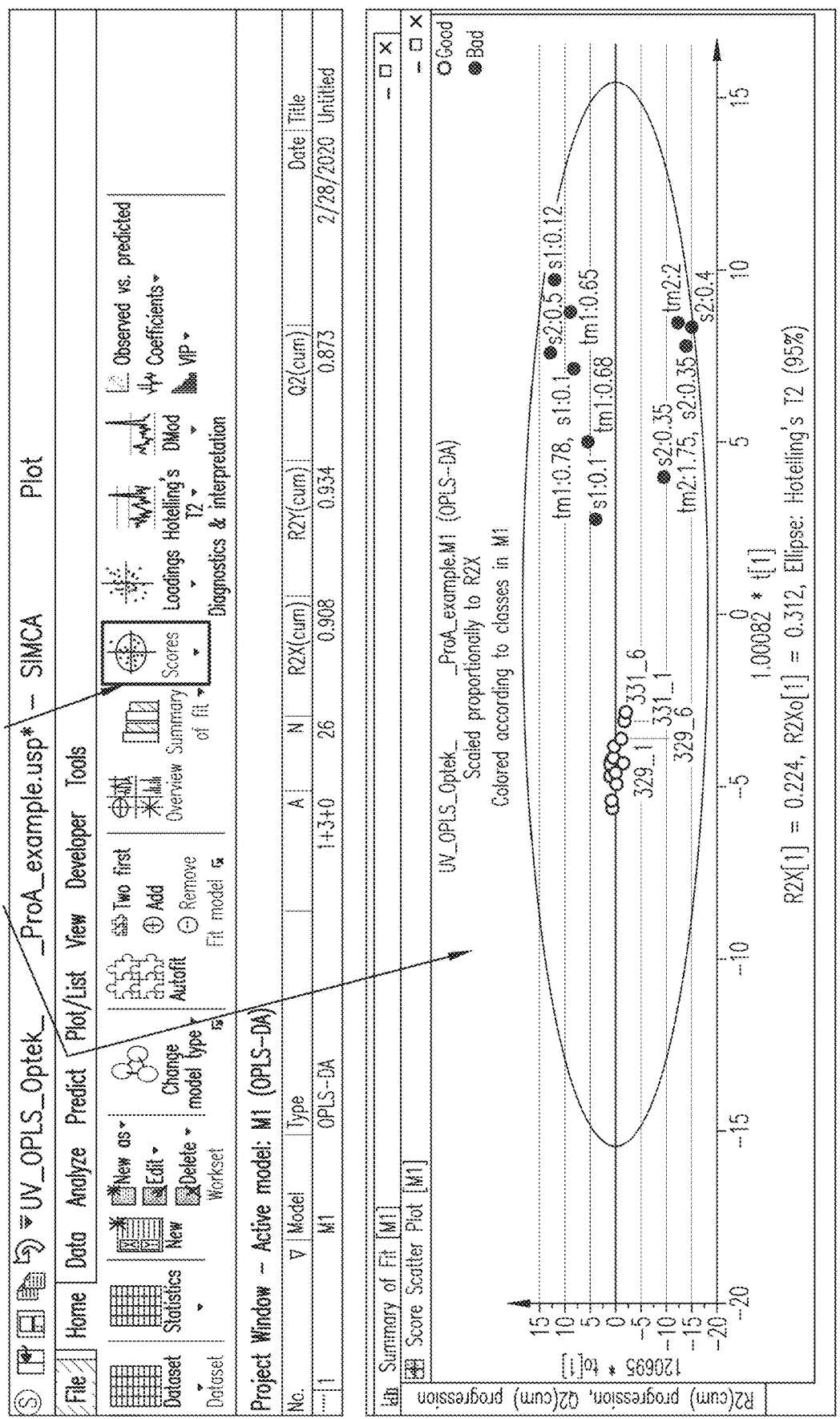
Figure 22A:
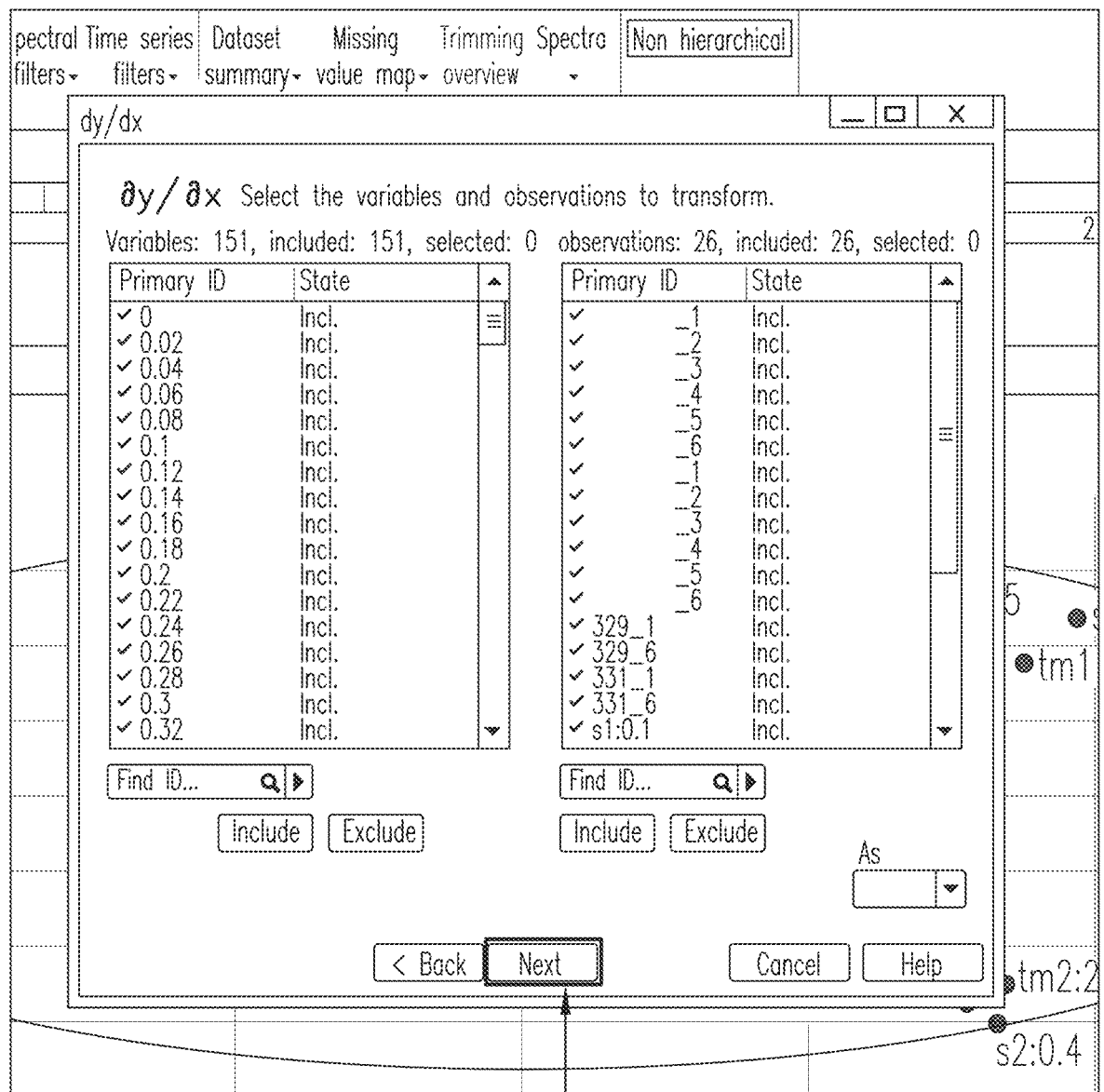
Figure 22B:
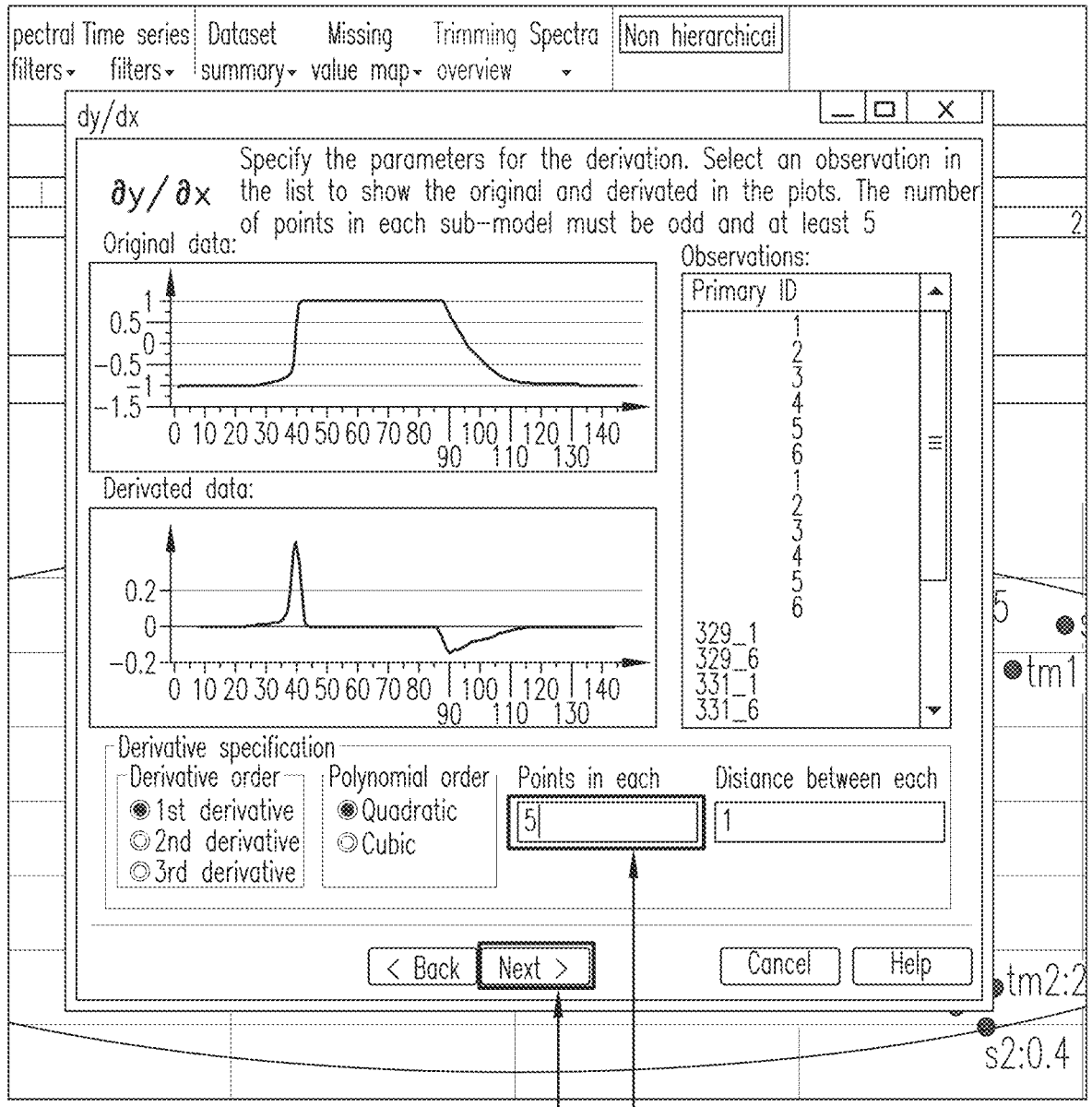
Figure 23A:
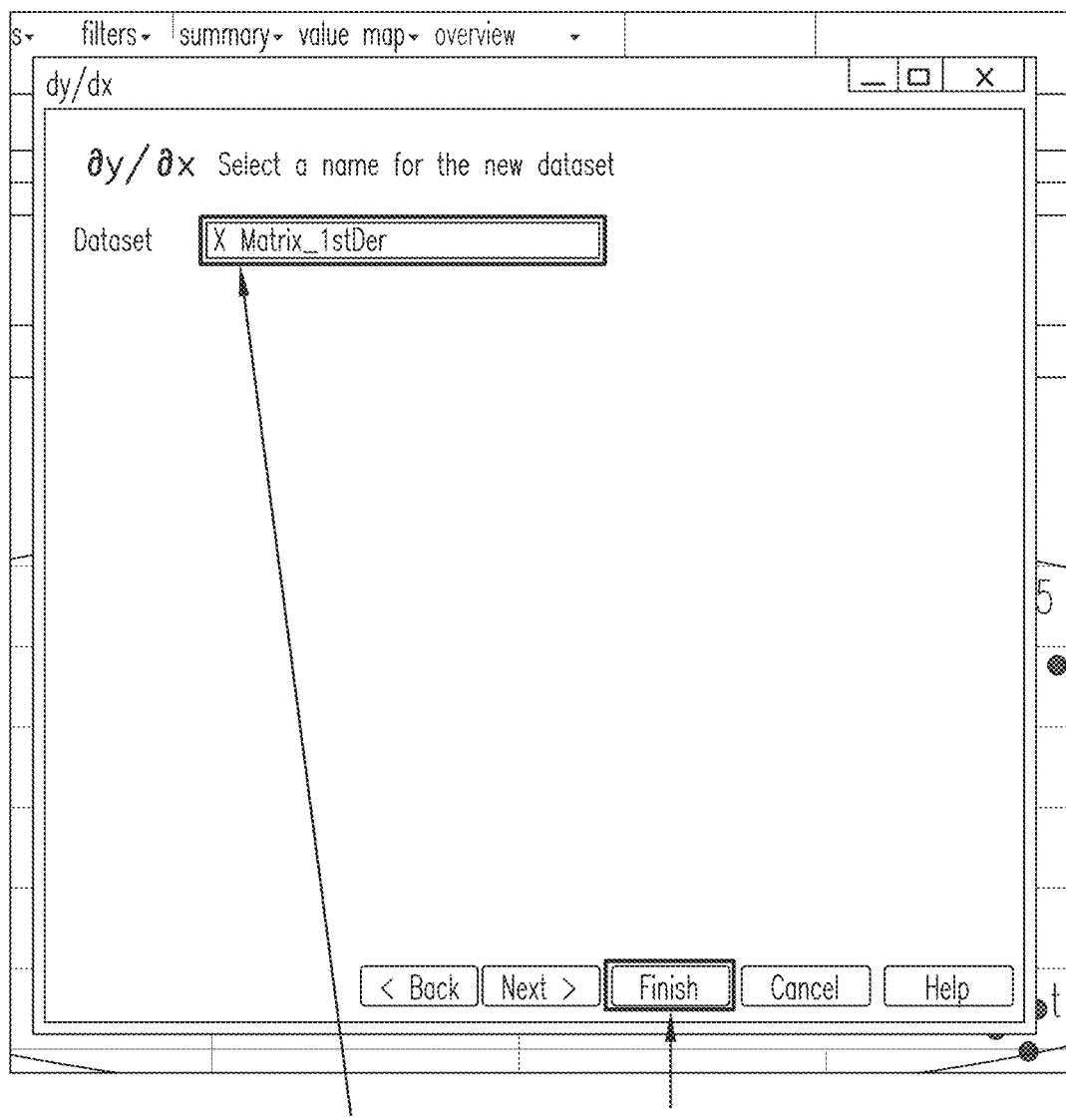
Figure 24A:
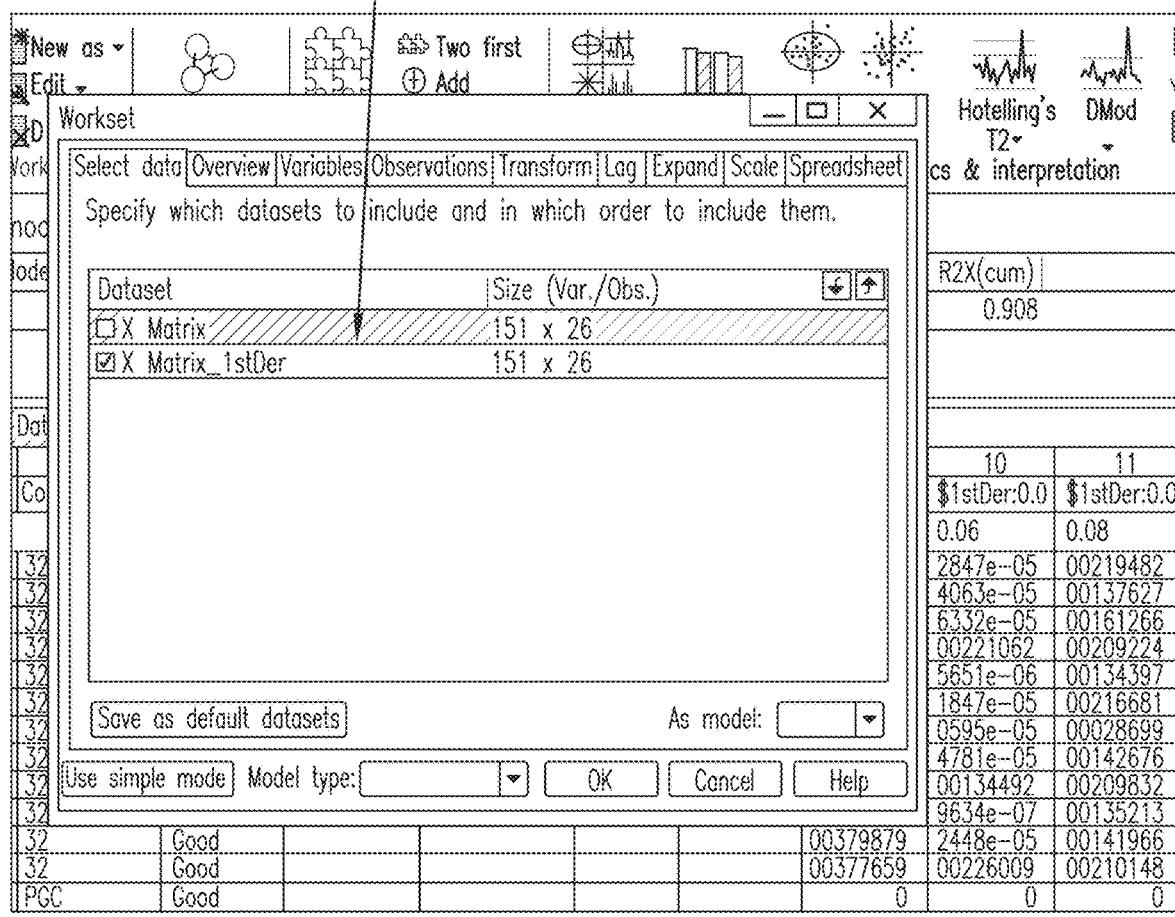
Figure 24B:
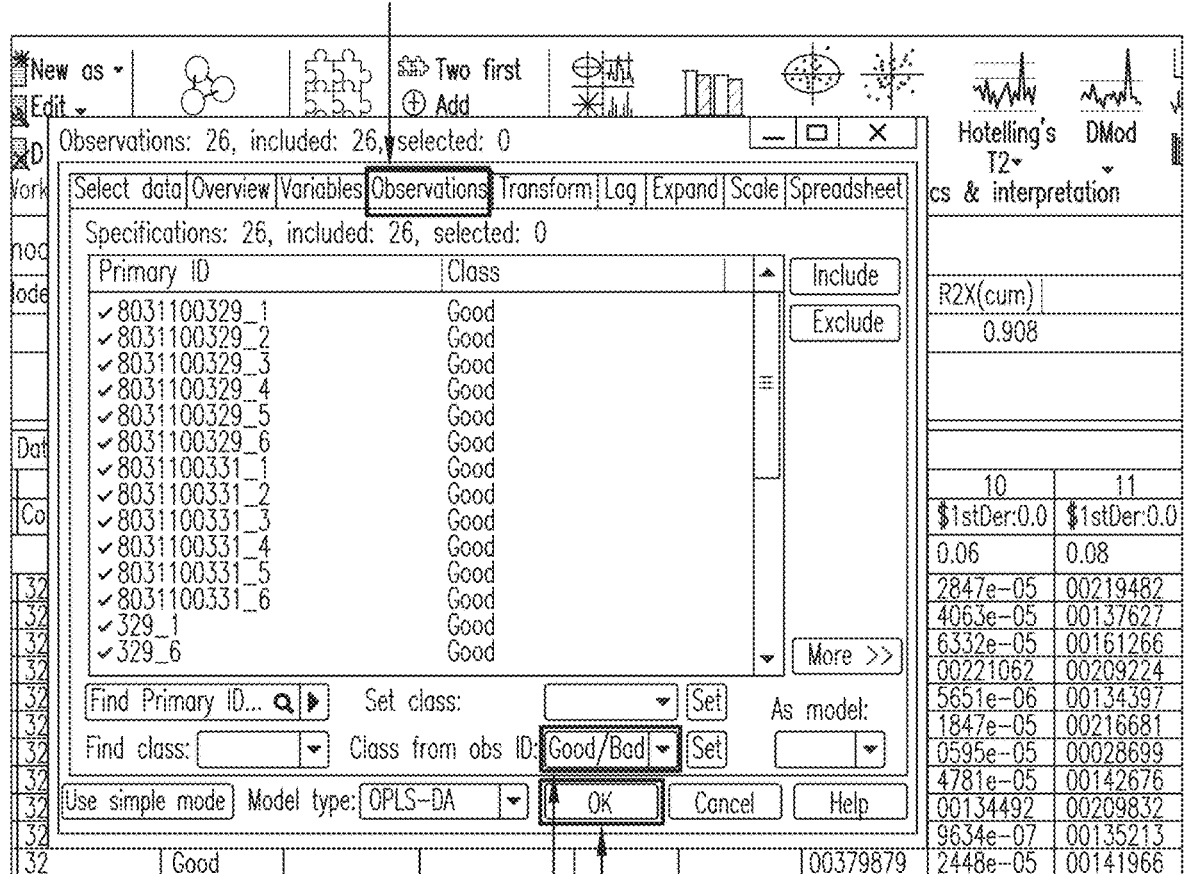
Figures 1, 25:
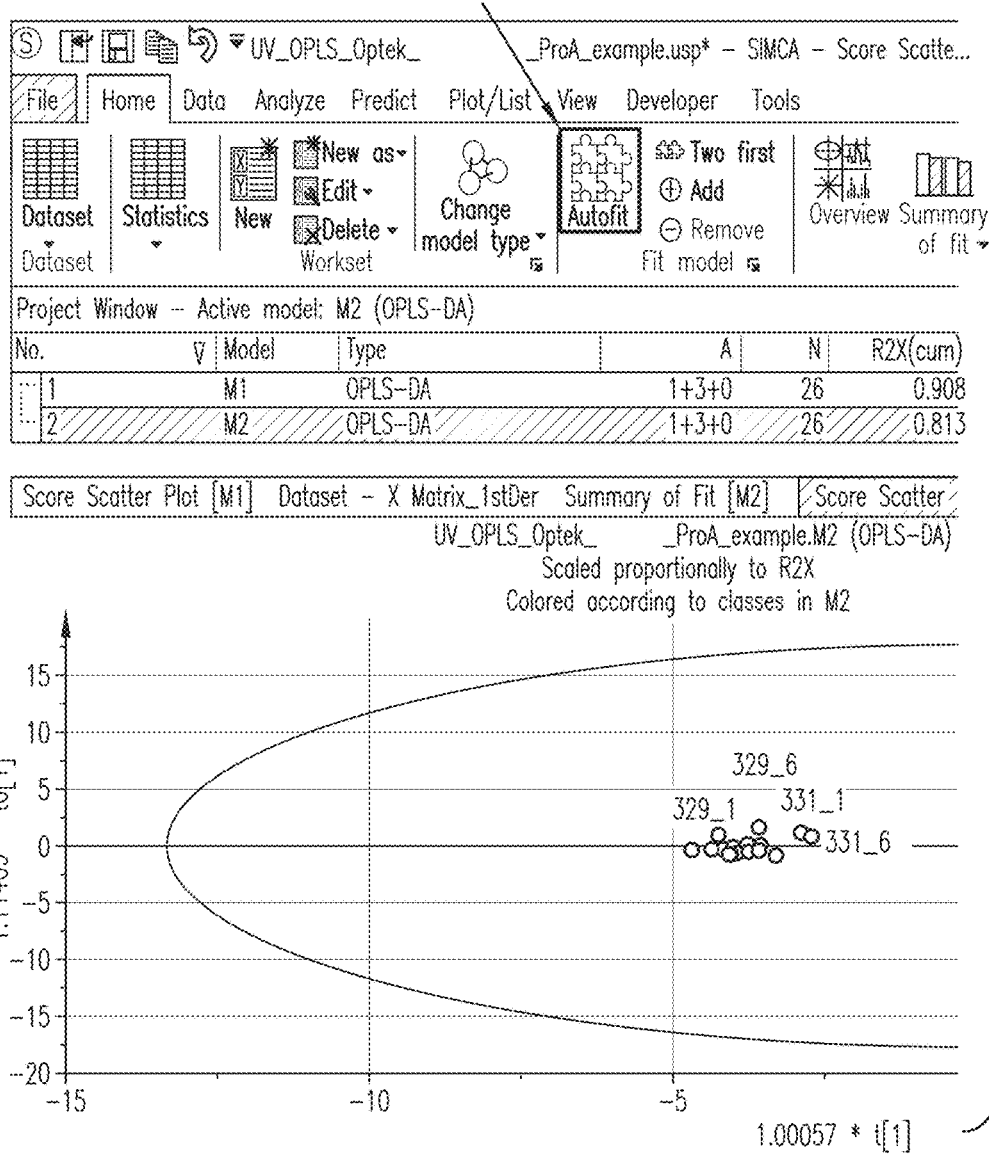
Figures 2, 25:
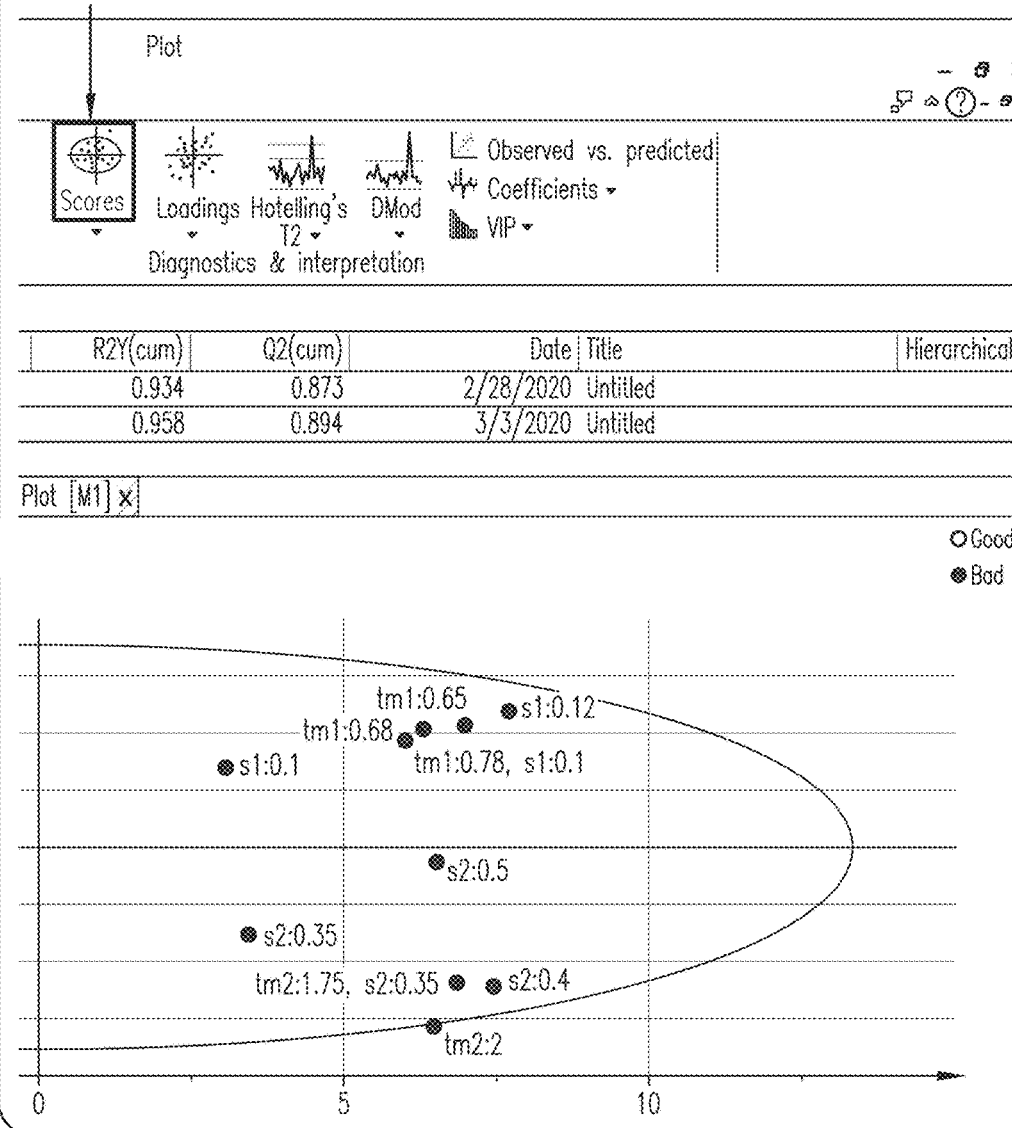
Figure 26A:
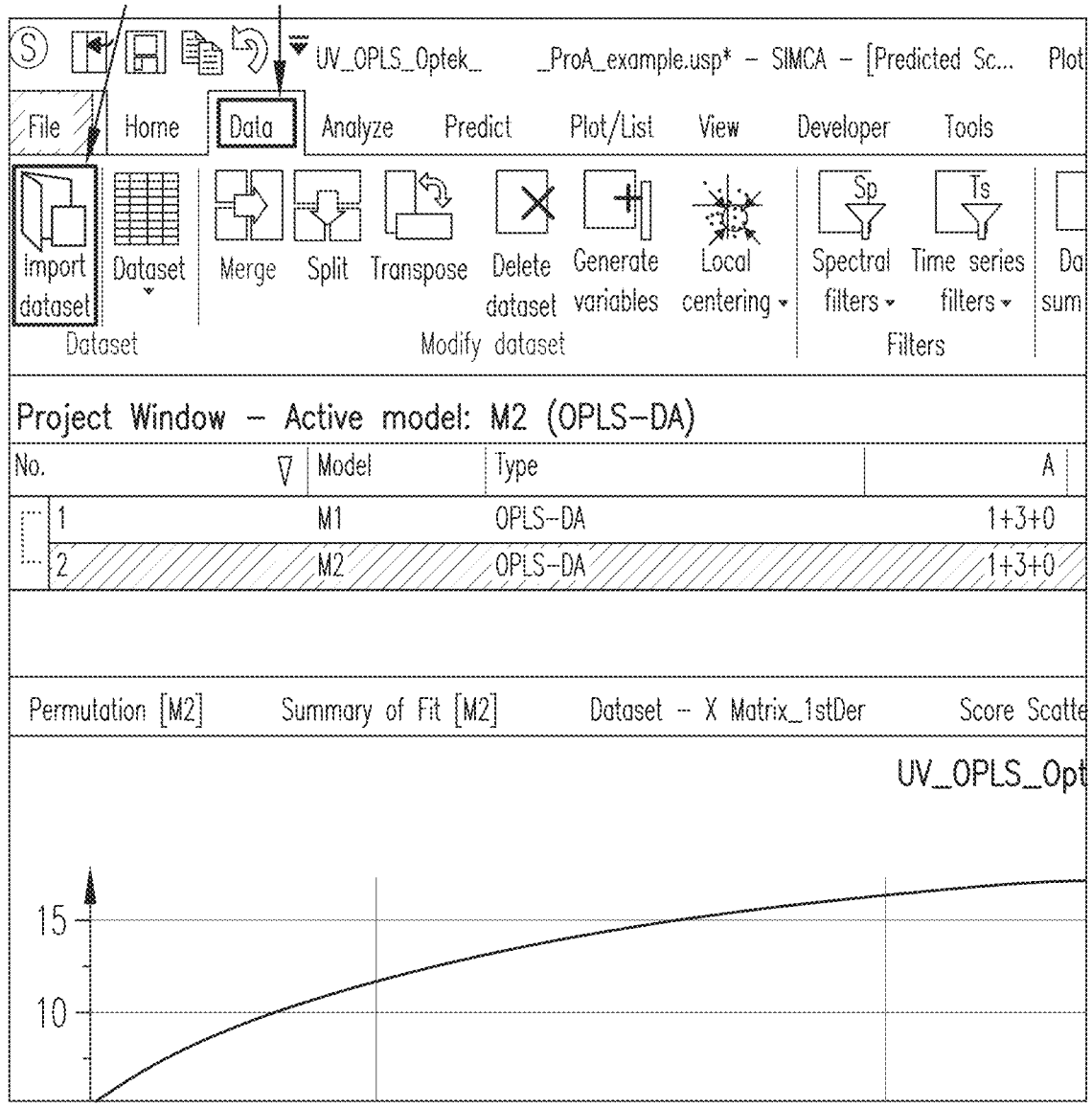
Figure 26B:
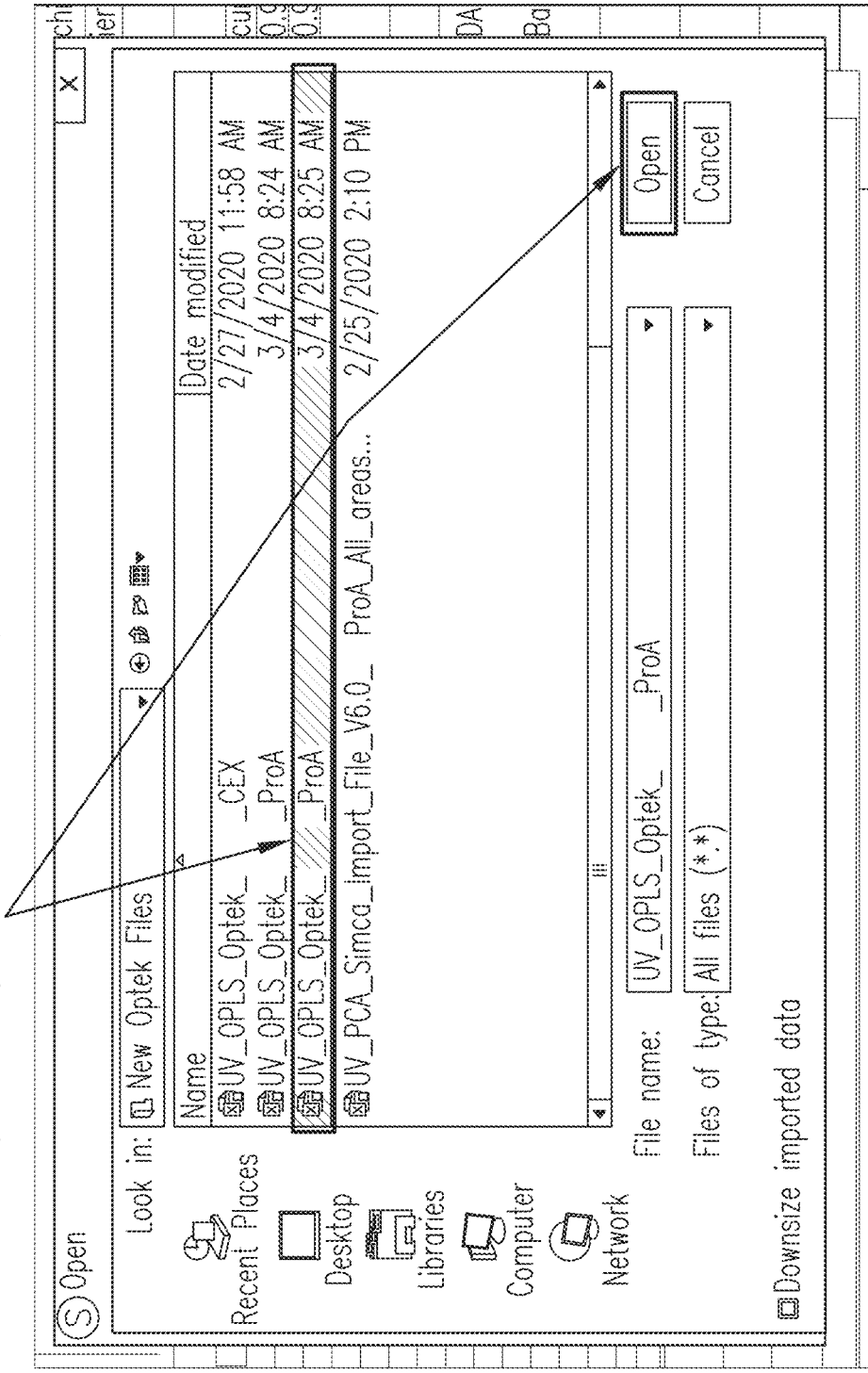
Figure 27A:
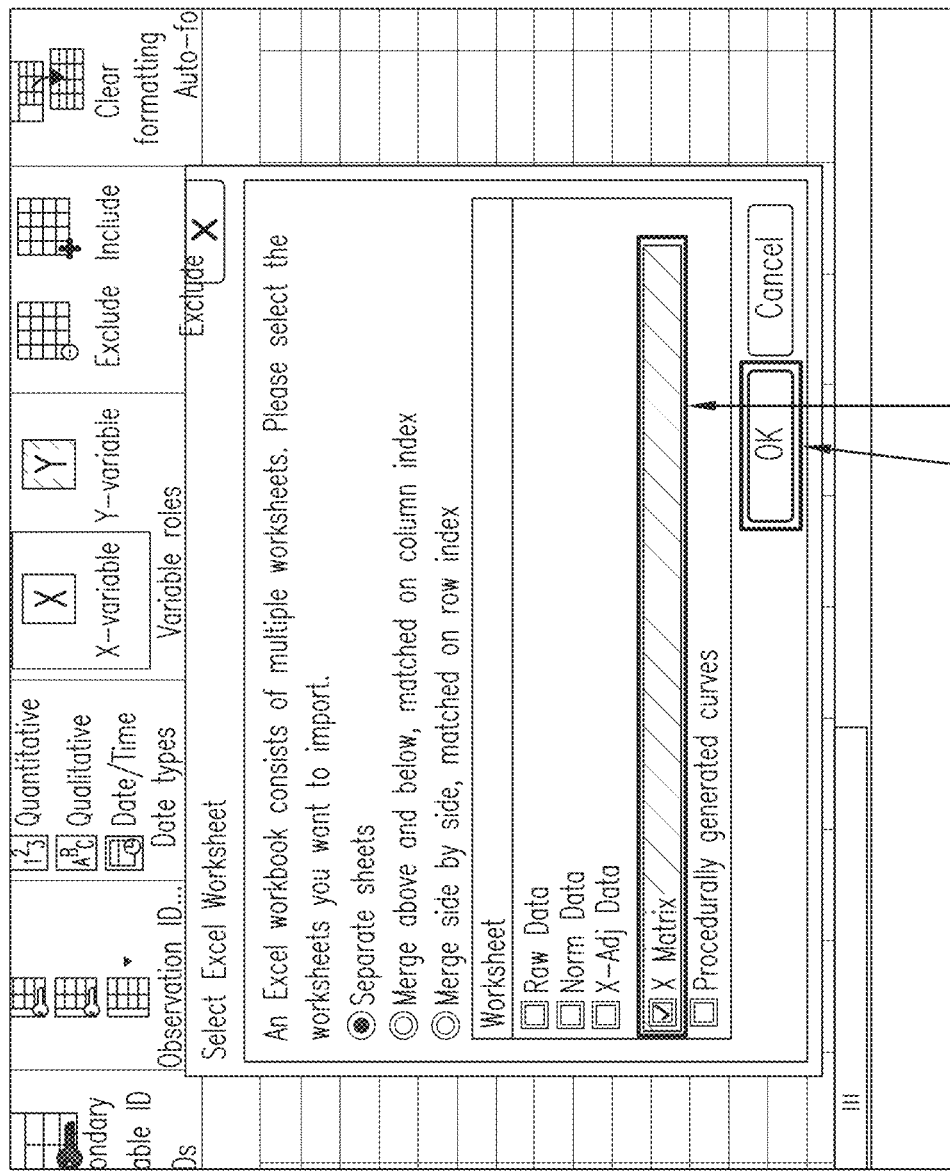
Figure 28:
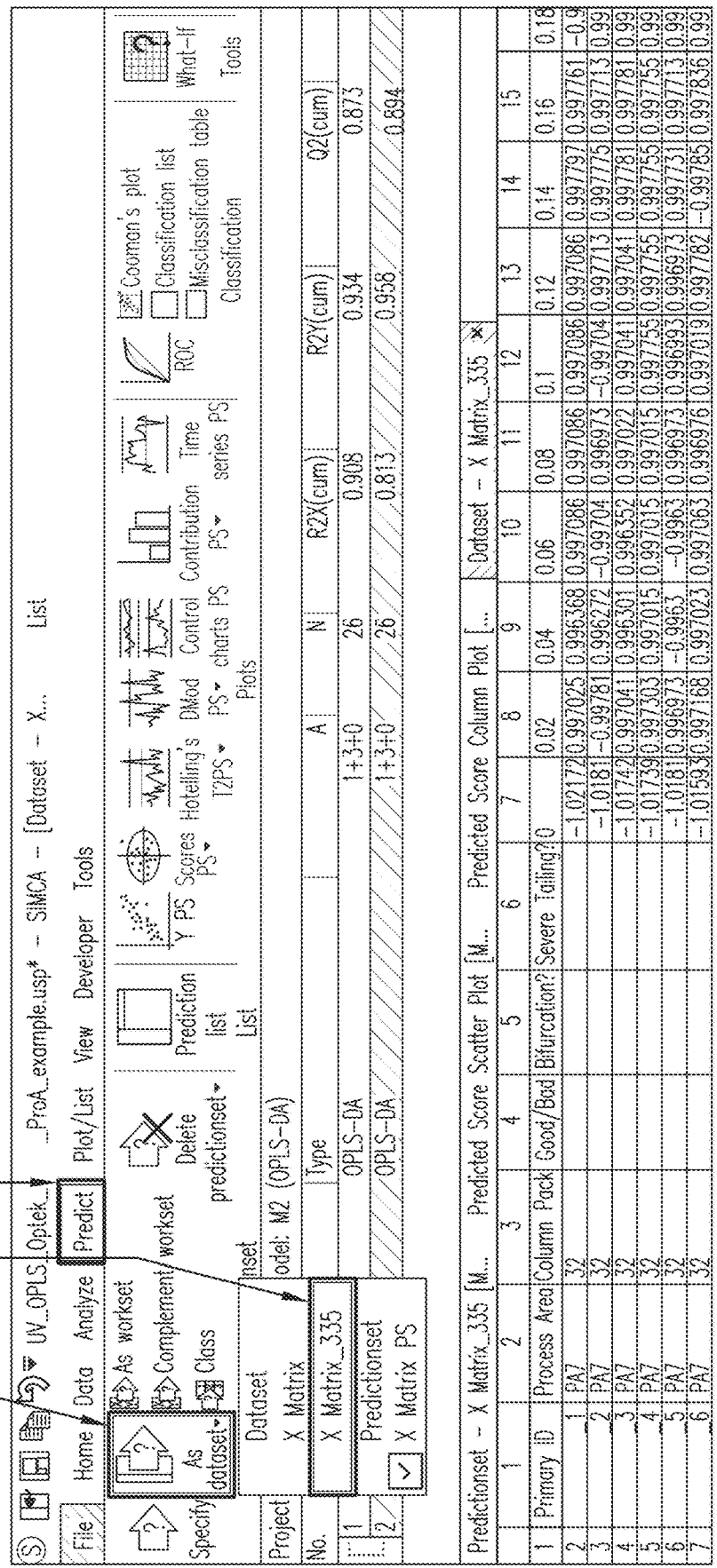
Figures 1, 29:
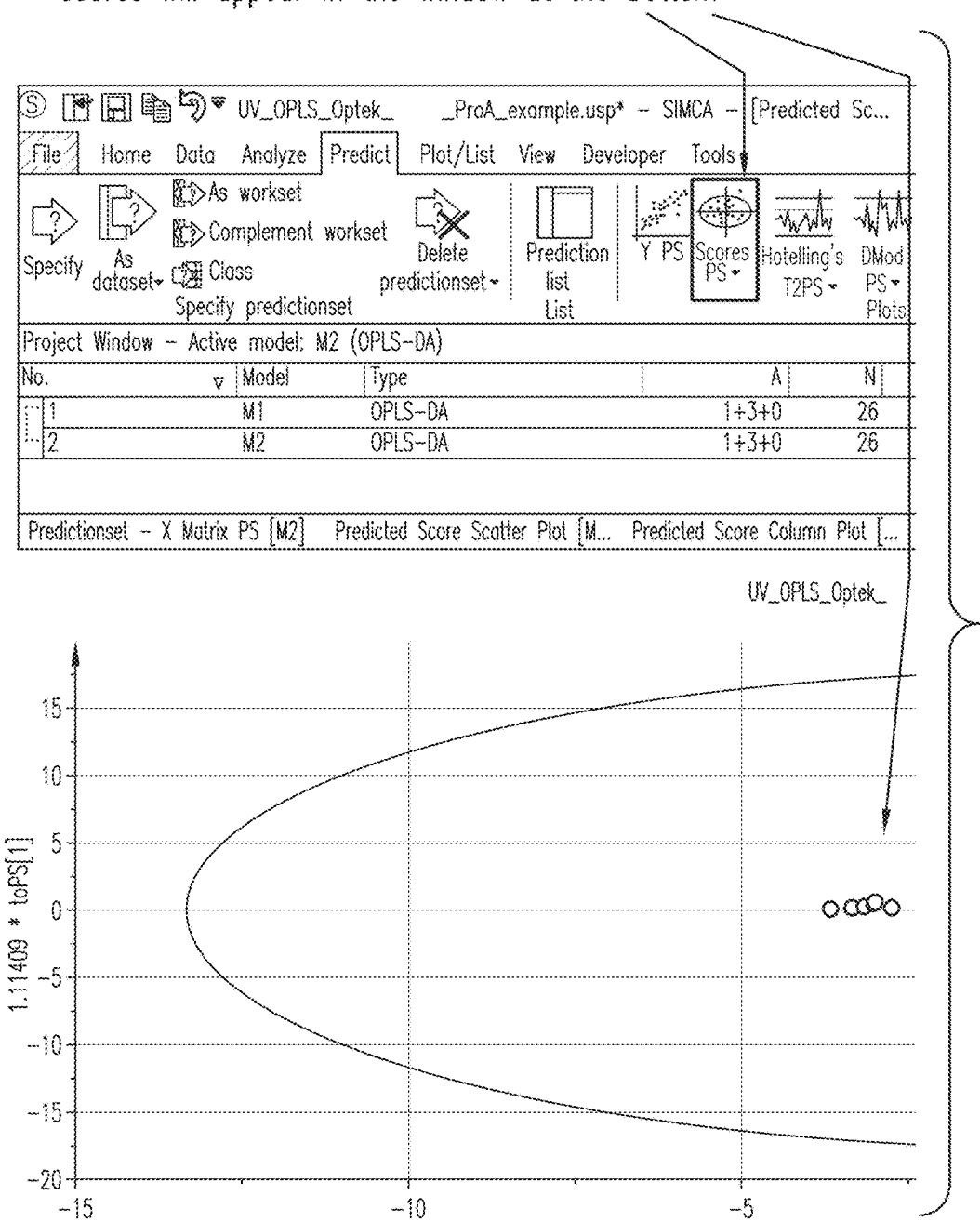
Figures 2, 29:
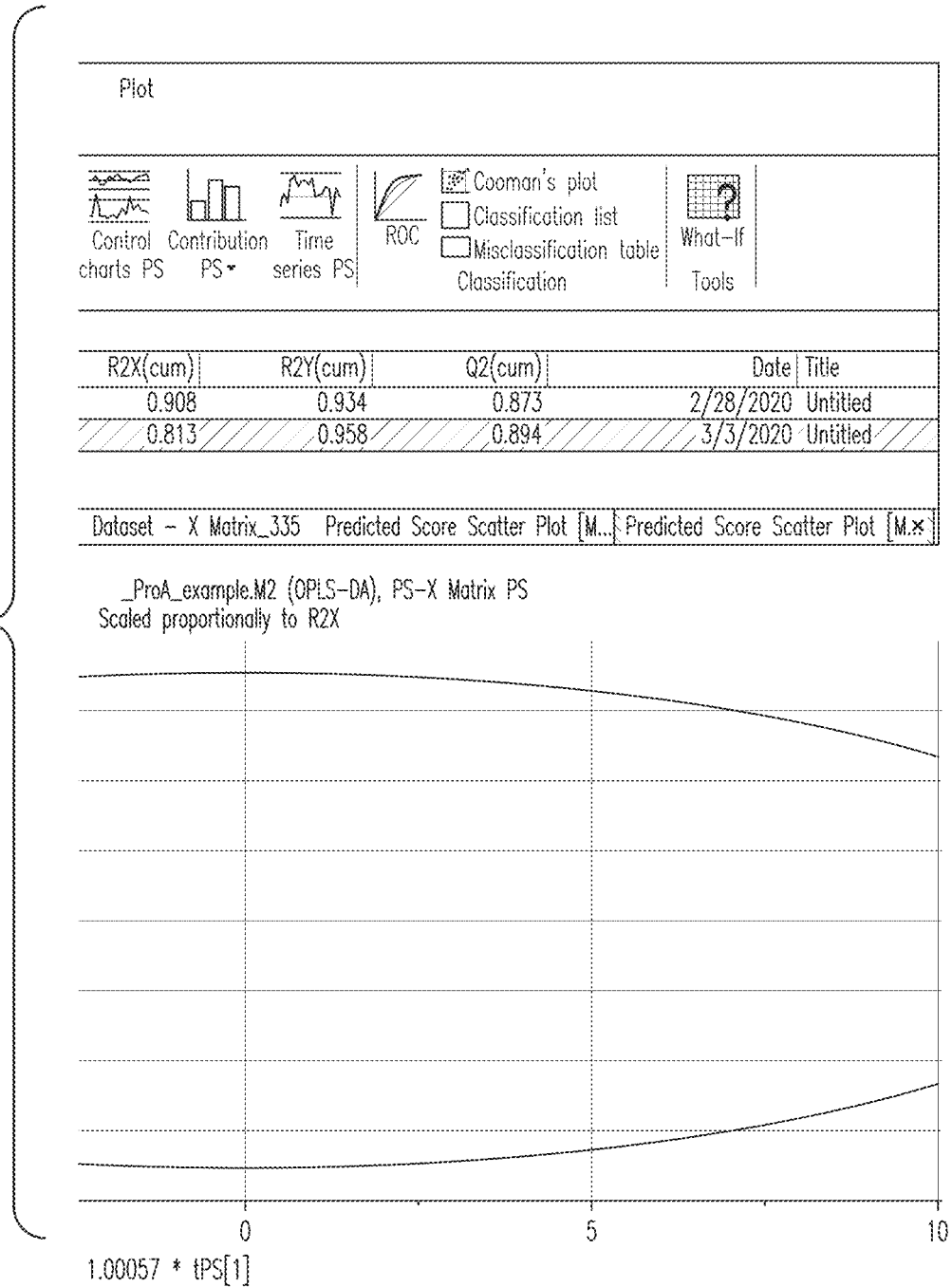
Figure 30:
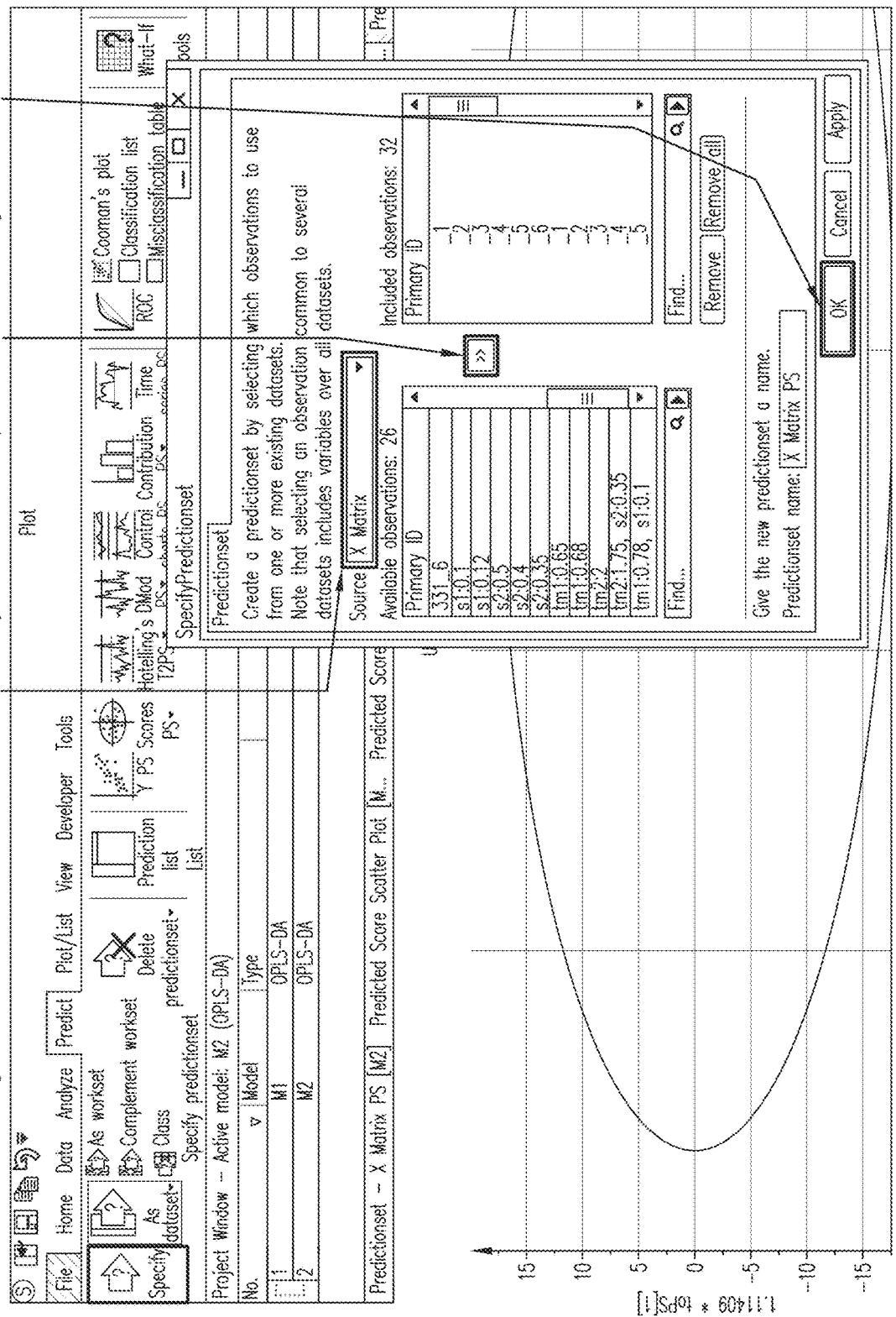
Figures 1, 31:
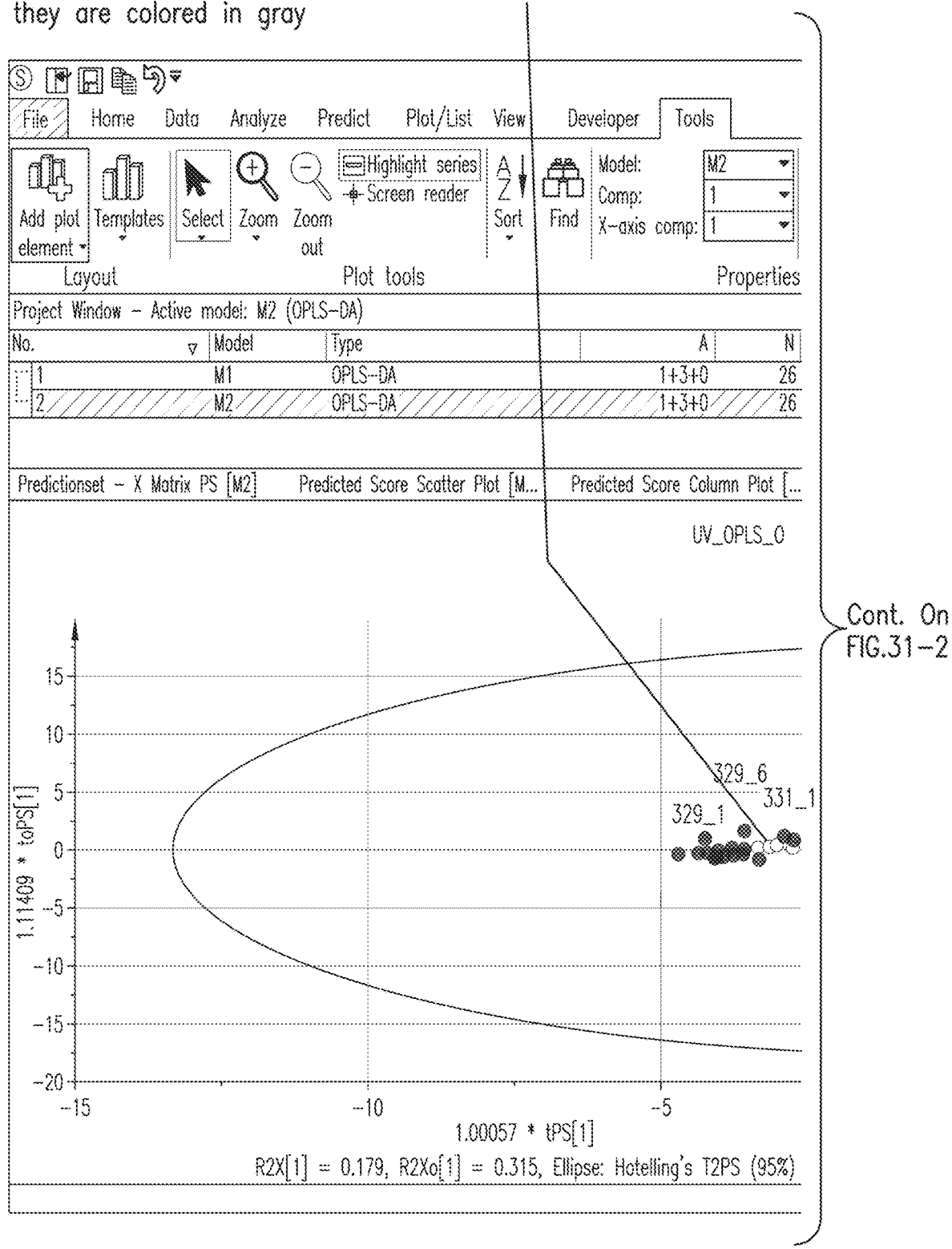
Figures 2, 31:
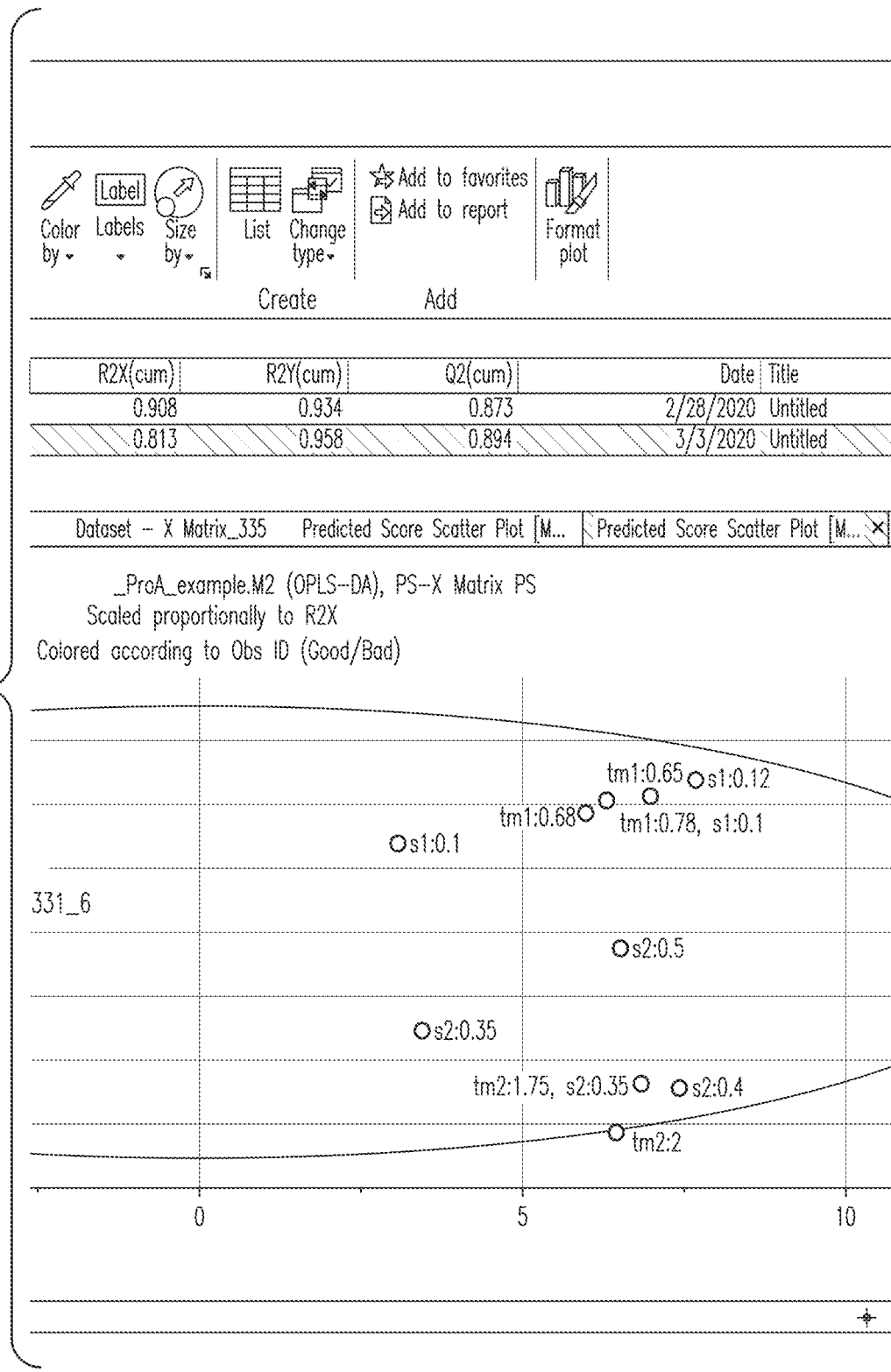

In embodiments, column volumes (CVs) are optimized as a volume interval to maximize data resolution and minimize required computational resources. In one embodiment, 0.02 CVs are used. FIGS. 5-1 and 5-2 provide an example of normalizing the data in accordance with embodiments disclosed herein.

In embodiments, the method includes evaluating the occurrence of column failures in the data, prior to generating curves. For example, if there are empirical examples of failed chromatograms, then artificially generated chromatograms may not be necessary. If there are a sufficient number of examples (e.g., 7 or greater, such as 8, 9, 10, 11, 12, 13, 14, 15 or greater) of failed chromatograms, then these chromatogram serve as the unacceptable data set and artificial curve generation is not needed.

In embodiments, the method optionally includes step 108, creating artificially generated curves from normalized data to provide the OPLS model examples of undesirable chromatograms. For example, step 108 is performed if there are no examples of unacceptable chromatograms. In embodiments, if the chromatogram is for a Bind-Elute Column, an elution peak generator tool, such as an Elution peak generator Microsoft Excel tool is used. In embodiments, if the chromatogram is for a flow-through column, a flow through curve generator excel tool is used.

In some embodiments, creating artificially generated curves includes determining which runs to use to generate the curves. For example, generally about 10-15 runs are a sufficient number of chromatograms to evaluate. If the data set is large (e.g., greater than 100 runs), runs are selected so that variability in the process is captured (e.g., only acceptable chromatograms are selected). In embodiments, creating artificially generated curves further includes copying data into a generation tab under F-Q and copying data for one of the runs into column E (e.g., chart displays the chromatogram in a first color, such as blue, in the figure next to the data whereas the mathematically generated chromatogram is displayed in a second color, such as red. In some embodiments, the method of creating artificially generated curves includes aligning a curve generated from the model to the real run data. For example, alignment can continue to be performed until root mean square error (RMSE) value in cell X1 stops decreasing which indicates that the model has been fitted to the chromatogram. Equation parameter data is copied for the curve and such values will be used to procedurally generate the new chromatograms. One or more of the prior actions may be repeated for selected run data. For example, runs with variability are selected as it is not required to fit multiple runs if they are relatively mirror images.

In embodiments, creating artificially generated curves for normalized data includes generating chromatograms that are representative of deterioration. For example, this may be performed by use of a computer program, such as Microsoft Excel which copies the mean and standard deviation values for each equation parameter into the table in Columns X and Y. In embodiments, for the elution peak generator four terms are utilized in the mathematical model: (1) $Tm1$: determines where the peak liftoff occurs (e.g., decreasing $tm1$ can shift the peak start to the left and increasing it can shift it to the right); (2) $S1$: determines how steep the peak liftoff is (e.g., decreasing $s1$ causes the peak liftoff to be sharper while increasing it makes it broader; (3) $Tm2$: determines where the peak end occurs (e.g., decreasing $tm2$ shifts peak end to the left and increasing $tm2$ shifts peak end to the right); and $S2$: determines how steep the peak dropdown is (e.g., decreasing $s2$ makes the peak end sharper while increasing s2 makes the peak end broader). In embodiments, additional terms for fitting the peak maximum may be utilized, such as if the top of the elution peak is not flat or if the UV sensor utilized requires additional input. In embodiments, the equation parameters are initially set to the mean parameter values from the generation tab and standard deviation (SD) values initially set to 0. Changing these values will change the corresponding equation parameter by the number of standard deviations entered into the cell (e.g., entering 3 into the SD cell next to s1 will increase the value of s1 by 3 SDs). In embodiments, each parameter is accessed and the SD value is either increased or decreased to create elution peaks indicative of deterioration such as broadening (increasing tm2), tailing (increasing s2); fronting and/or biomodal peaks are other common deterioration indicators which can be modeled as well. The action is performed allowing minor, moderate, and/or major variation examples to be created. In some embodiments, between 10-15 undesirable chromatograms are created using the aforementioned process, for example one or more minor deviation, one or more moderate and one or more major variation examples are created. In embodiments, the undesirable chromatograms include a greater number of minor deviation examples as compared to the moderate and major deviation examples. In embodiments, the undesirable chromatograms include a greater number of moderate deviation examples as compared to the major deviation examples. For example, in one embodiment, the undesirable chromatograms created include 7 minor deviation, 5 moderate deviation, and 3 as major deviation examples. FIGS. 6-1, 6-2, 6-3, 7, 8, 9-1, 9-2, 10-1, and 10-2 illustrate creating artificially generated curves from normalized data in accordance with embodiments disclosed herein.

In embodiments, the method further includes step 110, classifying data and formatting data for import into a multivariate tool, such as SIMCA, to determine what data is acceptable and unacceptable to train model. FIG. 11-1 and FIG. 11-2 show exemplary classifying and formatting data for SIMCA import in accordance with embodiments disclosed herein. For example, in some embodiments classifying and formatting data for importation into a multivariate tool includes (1) accessing the file utilized to normalize the data; (2) copying data for the artificially generated good and bad curves after the data already imported; (3) classifying each run/cycle into two groups—an acceptable or "good" group which contains chromatograms that do not show signs of column deterioration and an unacceptable or "bad" group which contains chromatograms that have indicators of column deterioration, such as tailing, peak broadening or other indicators known to those of ordinary skill in the art to indicate column deterioration; and (4) provide additional categories to classify runs, such as column packing number of resin cycle number, facilitating the ability to organize and read the data with a multivariate tool, such as SIMCA (for example, the generated groups can be colored and sorted in SIMCA).

In embodiments, the method includes importing data into a multivariate platform, such as SIMCA (step 112) and generating an OPLS model (step 114). FIGS. 12A, 12B, 13A, 13B-1, 13B-2, 14A, 14B, 15A, 15B-1, 15B-2, and 16 illustrate a protocol for importing data into SIMCA in accordance with embodiments disclosed herein. FIGS. 17, 18, 19 and 20 illustrate a protocol for generating an OPLS model in accordance with embodiments disclosed herein.

After generating an OPLS model, the method includes optimizing the OPLS model (step 116), validating and testing (step 118) and model application (step 120). In some embodiments, model application can include classifying new data as acceptable or unacceptable. In embodiments, the resulting optimized OPLS model is further augmented, such as by increasing, decreasing and/or modifying the number and/or content of the mathematically generated chromatogram inputs. For example, if the OPLS model is not satisfactory after optimizing OPLS settings, then it is further augmented by increasing, decreasing and/or modifying the number and/or content of mathematically generated chromatogram inputs. In embodiments, the OPLS model optimization are iterative with the mathematically generated chromatogram failure examples described herein. FIGS. 21, 22A, 22B, 23A, 23B, 24A, 24B, 25-1, and 25-2 show exemplary optimization of an OPLS model in accordance with embodiments disclosed herein. In embodiments, optimizing the OPLS includes determining if there is another set of model making parameters that fits a better model to the data. The $Q^2$ value represents the predictive power of the model (e.g., the higher $Q^2$, the higher the predictive power of the model). In embodiments, a $Q^2$ value of 0.7 or greater is considered acceptable. In some embodiments, additional models are created by comparing the $Q^2$ values to determine which model is better able to predict new data. Further, additional data transformations can be performed with a multivariate tool, such as SIMCA, to analyze a derived or transformed version of the imported data. In embodiments, one or more of the following parameters are adjusted to create additional OPLS models: (1) Derivative level (e.g., 0 or non-derived data, 1 or first derivative, 2 or second derivative, etc.); (2) Smoothing level (e.g., when taking derivatives or for additional data smoothing); and/or (3) Excluding observations (e.g., UV meter malfunction during the chromatogram).

In embodiments, an optimized UV OPLS model is analyzed to determine the predictive ability of the model. For example, a multivariate tool, such as SIMCA, is used to test the predictive ability of the optimized UV OPLS model. In embodiments, permutations are determined which indicate the statistical significance of the $R^2$ and $Q^2$ values by finding reference distributions of the $R^2$ and $Q^2$ values from permutation testing of the Y variable. If the model is a satisfactory model, the reference $R^2$ and $Q^2$ values will have lower values than the values of the model. In embodiments, a CV scores plot is generated which shows the cross validated component to the regular scores plot. A CV Scores plot which closely matches the regular scores plot indicates the model is satisfactory.

FIGS. 26A, 26B, 27A, 27B, 28, 29-1, 29-2, 30, 31-1, and 31-2 show exemplary application of the created OPLS model to classify new chromatograms as acceptable or unacceptable in accordance with embodiments disclosed herein.

In embodiments, the method further includes providing a sample to the chromatography system prior to acquiring the one or more chromatogram UV traces generated by a chromatography system during sample purification and/or separation.

Although the description herein describes in detail the use of the disclosed OPLS model with UV spectrophotometry it is contemplated that the disclosed model and methods may be used with any form of spectrophotometry that monitors the outlet of the column for the eluate, including, but not limited to RAMAN or IR.

In some embodiments, the chromatography system capable of sample separation to purify and/or separate sample components comprises a liquid chromatography system. In some embodiments, the system is a chromatography system is a hydrophobic chromatography system, reverse phase liquid chromatography system, ion-exchange chromatography system, size exclusion chromatography system, affinity chromatography system, or hydrophilic-interaction chromatography system.

In some embodiments, the chromatography column temperature can be maintained at a constant temperature throughout the chromatography run, e.g., using a commercial column heater. In some embodiments, the column is maintained at a temperature between about 18° C. to about 70° C., e.g., about 30° C. to about 60° C., about 40° C. to about 50° C., e.g., at about 20° C., about 25° C., about 30° C., about 35° C., about 40° C., about 45° C., about 50° C., about 55° C., about 60° C., about 65° C., or about 70° C. In some embodiments, the column temperature is about 40° C. In some embodiments, the run time can be between about 15 to about 240 minutes, e.g., about 20 to about 70 min, about 30 to about 60 min, about 40 to about 90 min, about 50 min to about 100 min, about 60 to about 120 min, about 50 to about 80 min.

In some embodiments, the mobile phase is an aqueous mobile phase. A representative aqueous mobile phase contains 208 mM sodium acetate and 10 mM ammonium bicarbonate. The UV traces are typically recorded at 215 and 280 nm.

In some exemplary embodiments, the mobile phase used to elute the protein can be a mobile phase that can be compatible with a mass spectrometer.

In some exemplary embodiments, the mobile phase used in the liquid chromatography device can include water, acetonitrile, trifluoroacetic acid, formic acid, or combination thereof.

In some exemplary embodiments, the mobile phase for manufacturing operations can have a flow rate varying within operation and operation to operation from 60 L/hr to 1800 L/hr.

In some embodiments, the sample is a protein or cell culture medium including a protein, exemplary proteins including, but not limited to, an antibody, a fusion protein, recombinant protein, or a combination thereof.

In some embodiments, the antibody is a bispecific antibody, antibody fragment or a multispecific antibody.

In some exemplary embodiments, the antibody is a monoclonal antibody, such as, but not limited to, a monoclonal antibody of isotype IgG1, IgG2, IgG3, IgG4, or mixed isotype.

In some exemplary embodiments, the protein is be a therapeutic protein.

In some exemplary embodiments, the protein can be an immunoglobulin protein.

In one exemplary embodiment, the protein can be a protein variant.

In one exemplary embodiment, the protein can be a post-translationally modified protein.

In one exemplary embodiment, the post-translationally modified protein can be a formed by cleavage, N-terminal extensions, protein degradation, acylation of the N-terminus, biotinylation, amidation of the C-terminal, oxidation, glycosylation, iodination, covalent attachment of prosthetic groups, acetylation, alkylation, methylation, adenylation, ADP-ribosylation, covalent cross links within, or between, polypeptide chains, sulfonation, prenylation, Vitamin C dependent modifications, Vitamin K dependent modification, glutamylation, glycylation, glycosylation, deglycosylation, isoprenylation, lipoylation, phosphopantetheinylation, phosphorylation, sulfation, citrullination, deamidation, formation of disulfide bridges, proteolytic cleavage, ISGylation, SUMOylation or ubiquitination (covalent linkage to the protein ubiquitin).

In one exemplary embodiment, the post-translationally modified protein can be formed on oxidation of a protein.

In embodiments, the disclosed methods are used to monitor column deterioration due to a change in the column packing status, an accumulation of contaminant components, channeling through the column, microparticle blockage, desorption from the solid phase, or a combination thereof. In embodiments, the disclosed methods detect column deterioration prior to column failure. In embodiments the disclosed methods detect imminent column deterioration prior to a sign of column deterioration is manifested, such as increased column pressure, decreased theoretical plates, shortened retention time, poor peak shape, and/or decreased resolution.

It is contemplated that the methods described herein can be performed by software, hardware, or both, of a computing environment, such as one or more computing devices. For example, computing devices include server computers, desktop computers, laptop computers, notebook computers, handheld devices, netbooks, tablet devices, mobile devices, and other types of computing devices.

Figure 41:
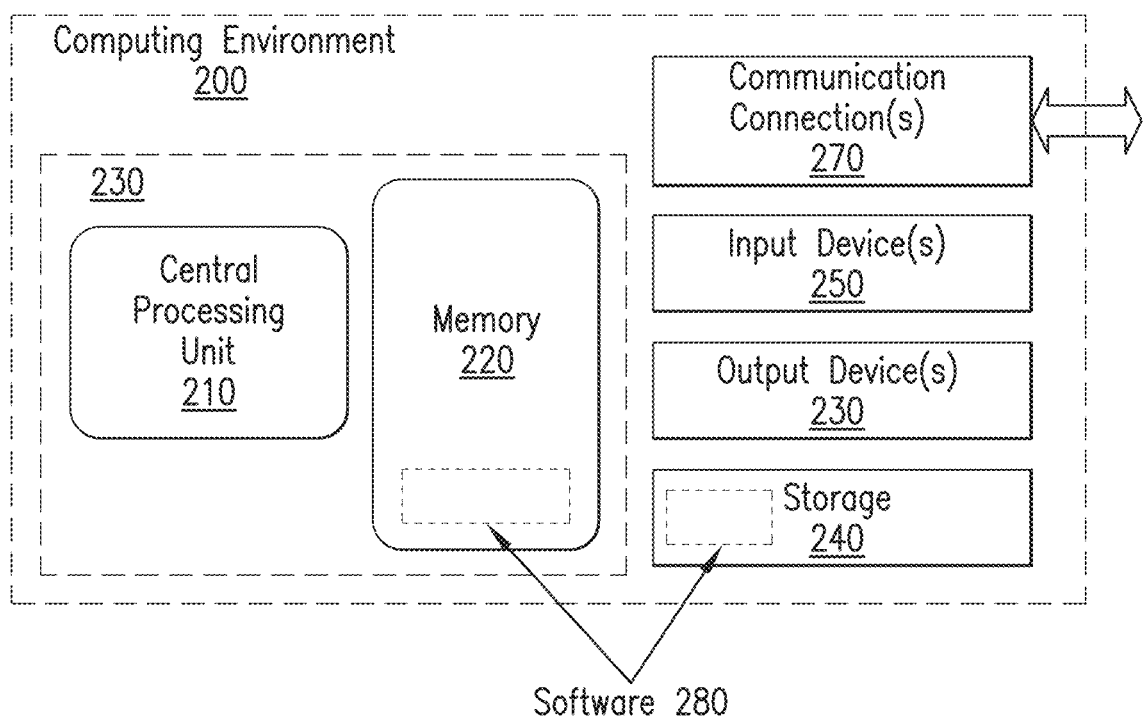
FIG. 41 shows a schematic representation of an exemplary computing environment for performing aspects of the methods disclosed herein.

FIG. 41 illustrates an exemplary computing environment 200 for implementation of various aspects of the methods disclosed herein, including creating and/or utilizing an OPLS for monitoring methods of monitoring chromatography performance. The computing environment 200 is not intended to suggest any limitation as to scope of use or functionality, as the technologies may be implemented in diverse general-purpose or special-purpose computing environments. For example, the disclosed technology may be implemented using a computing device comprising a processing unit, memory, and storage, storing computer-executable instructions implementing methods disclosed herein. The disclosed technology may also be implemented with other computer system configurations, including hand held devices, multiprocessor systems, microprocessor-based or programmable consumer electronics, network PCs, minicomputers, mainframe computers, a collection of client/server systems, and the like. The disclosed technology may also be practiced in distributed computing environments where tasks are performed by remote processing devices that are linked through a communications network. In a distributed computing environment, program modules may be located in both local and remote memory storage devices With reference to FIG. 41, the computing environment 200 includes at least one processing unit 210 coupled to memory 220. In FIG. 41, this basic configuration 230 is included within a dashed line. The processing unit 210 executes computer-executable instructions and may be a real or a virtual processor. In a multi-processing system, multiple processing units execute computer-executable instructions to increase processing power. The memory 220 may be volatile memory (e.g., registers, cache, RAM), non-volatile memory (e.g., ROM, EEPROM, flash memory, etc.), or some combination of the two. The memory 220 can store software 280 implementing any of the technologies described herein.

A computing environment may have additional features. For example, the computing environment 200 includes storage 240, one or more input devices 250, one or more output devices 260, and one or more communication connections 270. An interconnection mechanism (not shown) such as a bus, controller, or network interconnects the components of the computing environment 200. Typically, operating system software (not shown) provides an operating environment for other software executing in the computing environment 200, and coordinates activities of the components of the computing environment 200.

The storage 240 may be removable or non-removable, and includes magnetic disks, magnetic tapes or cassettes, CD-ROMs, CD-RWs, DVDs, or any other computer-readable media which can be used to store information and which can be accessed within the computing environment 200. The storage 240 can store software 280 containing instructions for any of the technologies described herein.

The input device(s) 250 may be a touch input device such as a keyboard, mouse, pen, or trackball, a voice input device, a scanning device, or another device that provides input to the computing environment 200. For audio, the input device(s) 250 may be a sound card or similar device that accepts audio input in analog or digital form, or a CD-ROM reader that provides audio samples to the computing environment. The output device(s) 260 may be a display, printer, speaker, CD-writer, or another device that provides output from the computing environment 200.

The communication connection(s) 270 enable communication over a communication mechanism to another computing entity. The communication mechanism conveys information such as computer-executable instructions, audio/video or other information, or other data. By way of example, and not limitation, communication mechanisms include wired or wireless techniques implemented with an electrical, optical, RF, infrared, acoustic, or other carrier.

The techniques herein can be described in the general context of computer-executable instructions, such as those included in program modules, being executed in a computing environment on a target real or virtual processor. Generally, program modules include routines, programs, libraries, objects, classes, components, data structures, etc., that perform particular tasks or implement particular abstract data types. The functionality of the program modules may be combined or split between program modules as desired in various embodiments. Computer-executable instructions for program modules may be executed within a local or distributed computing environment.

Any of the disclosed methods can be implemented as computer-executable instructions or a computer program product stored on one or more computer-readable storage media (e.g., non-transitory computer-readable media, such as one or more optical media discs such as DVD or CD, volatile memory components (such as DRAM or SRAM, or non-volatile memory components such as hard drives) and executed on a computer (e.g., any commercially available computer, including smart phones or other mobile devices that include computing hardware). Computer-readable media does not include propagated signals. Any of the computer-executable instructions for implementing the disclosed methods as well as any data created and used during implementation of the disclosed embodiments can be stored on one or more computer-readable media (e.g., non-transitory computer-readable media).

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium can even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the internet, a wide-area network, a local-area network, a client-server network (such as a cloud computing network), or other such network using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, Phython or any other suitable programming language. Likewise, the disclosed technology is not limited to any particular computer or type of hardware.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium. A code segment may represent a procedure, a function, a subprogram, a program, a routine, a subroutine, a module, program code, a software package, a class, or any combination of instructions, data structures, program statements, and the like.

In embodiments, any of the software-based embodiments (including, for example, computer-executable instructions for causing a computer to perform any of the disclosed methods) can be uploaded, downloaded or remotely accessed through a suitable communication means. Such suitable communication means include, for example, the internet, the World Wide Web, an intranet, cable (including fiber optic cable), magnetic communications, electromagnetic communications (including RF, microwave, and infrared communications), electronic communications, or other such communication means.

In various embodiments, an article of manufacture may be employed to implement one or more methods as disclosed herein. The article of manufacture may include a computer-readable non-transitory storage medium and a storage medium. The storage medium may include programming instructions configured to cause an apparatus to practice some or all aspects of a disclosed method using a computing device, in accordance with embodiments of the present disclosure. The storage medium may represent a broad range of persistent storage medium known in the art, including but not limited to flash memory, optical disks or magnetic disks. The programming instructions, in particular, may enable an apparatus, in response to their execution by the apparatus, to perform various operations described herein. For example, the storage medium may include programming instructions configured to cause an apparatus to practice some or all aspects of a disclosed method, such as a method of monitoring column chromatography performance, including creating an OPLS model, in accordance with embodiments of the present disclosure.

Although various example methods, apparatus, systems, and articles of manufacture have been described herein, the scope of coverage of the present disclosure is not limited thereto. On the contrary, the present disclosure covers all methods, apparatus, and articles of manufacture fairly falling within the scope of the appended claims either literally or under the doctrine of equivalents. For example, although the above discloses example systems including, among other components, software or firmware executed on hardware, it should be noted that such systems are merely illustrative and should not be considered as limiting. In particular, it is contemplated that any or all of the disclosed hardware, software, and/or firmware components can be embodied exclusively in hardware, exclusively in software, exclusively in firmware or in some combination of hardware, software, and/or firmware.

EXAMPLES

The following examples are put forth so as to provide those of ordinary skill in the art with a complete disclosure and description of how to make and use the methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1

Case Study: UV OPLS Model

Figures 1, 32:
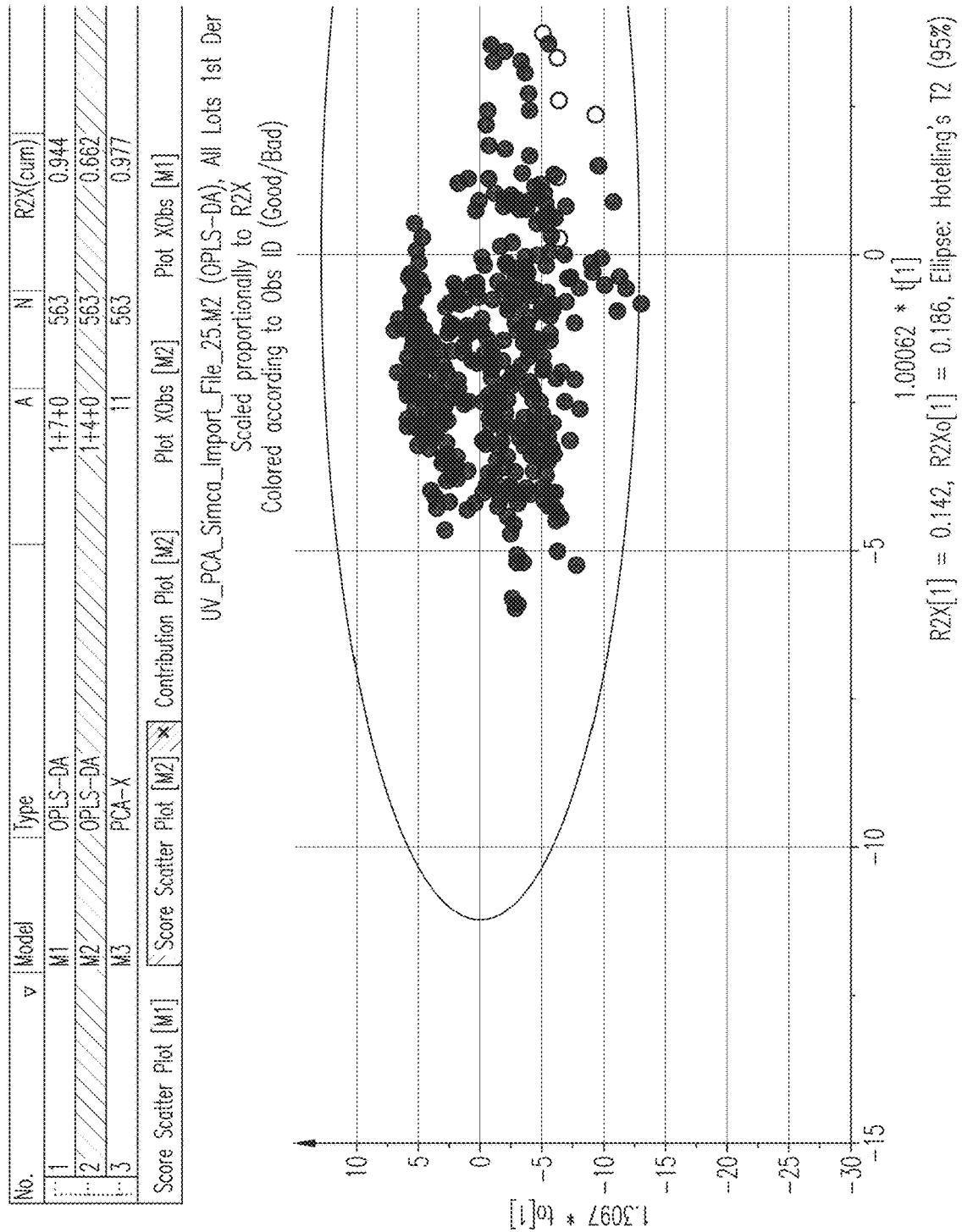
Figures 2, 32:
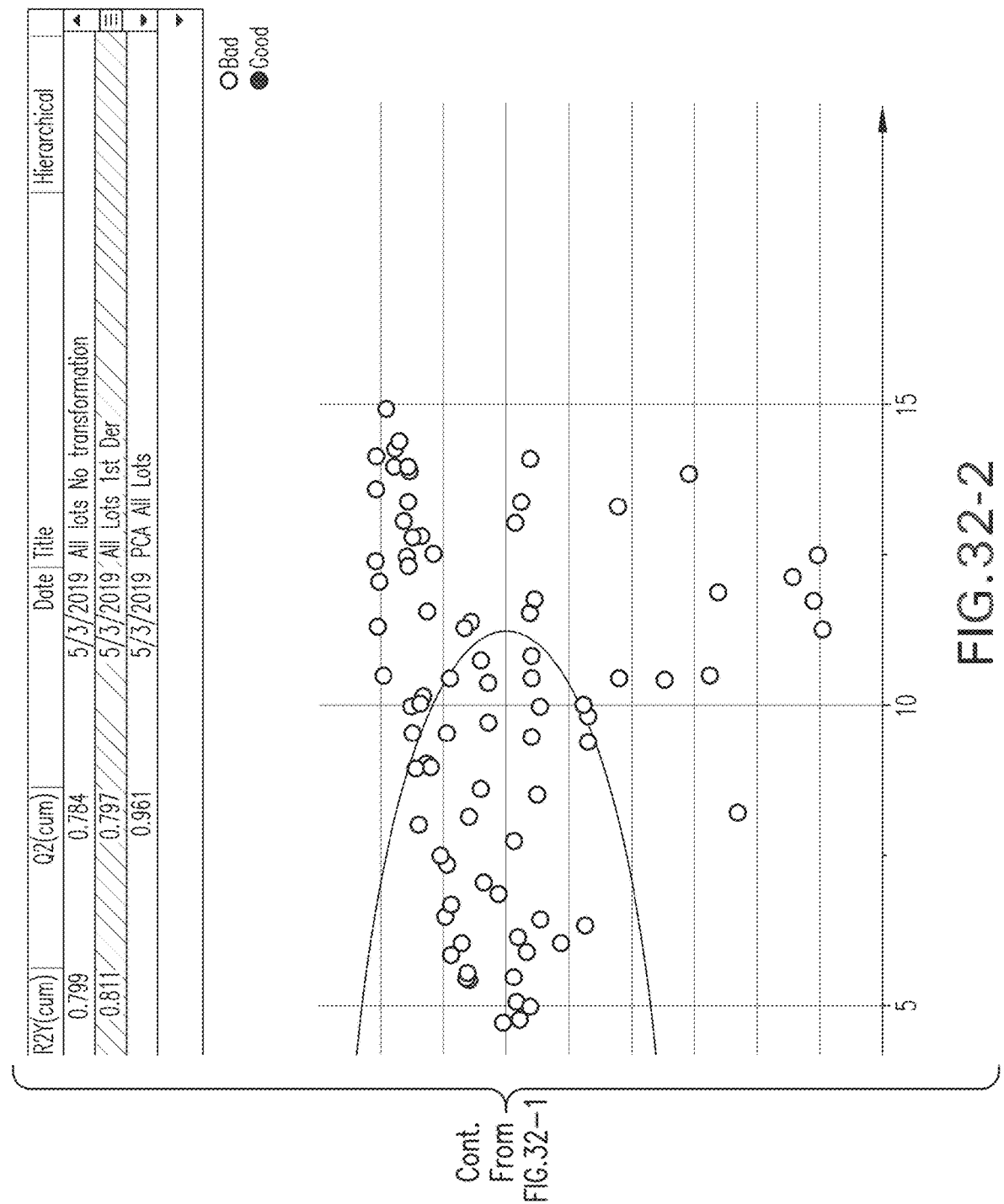
Figure 33:
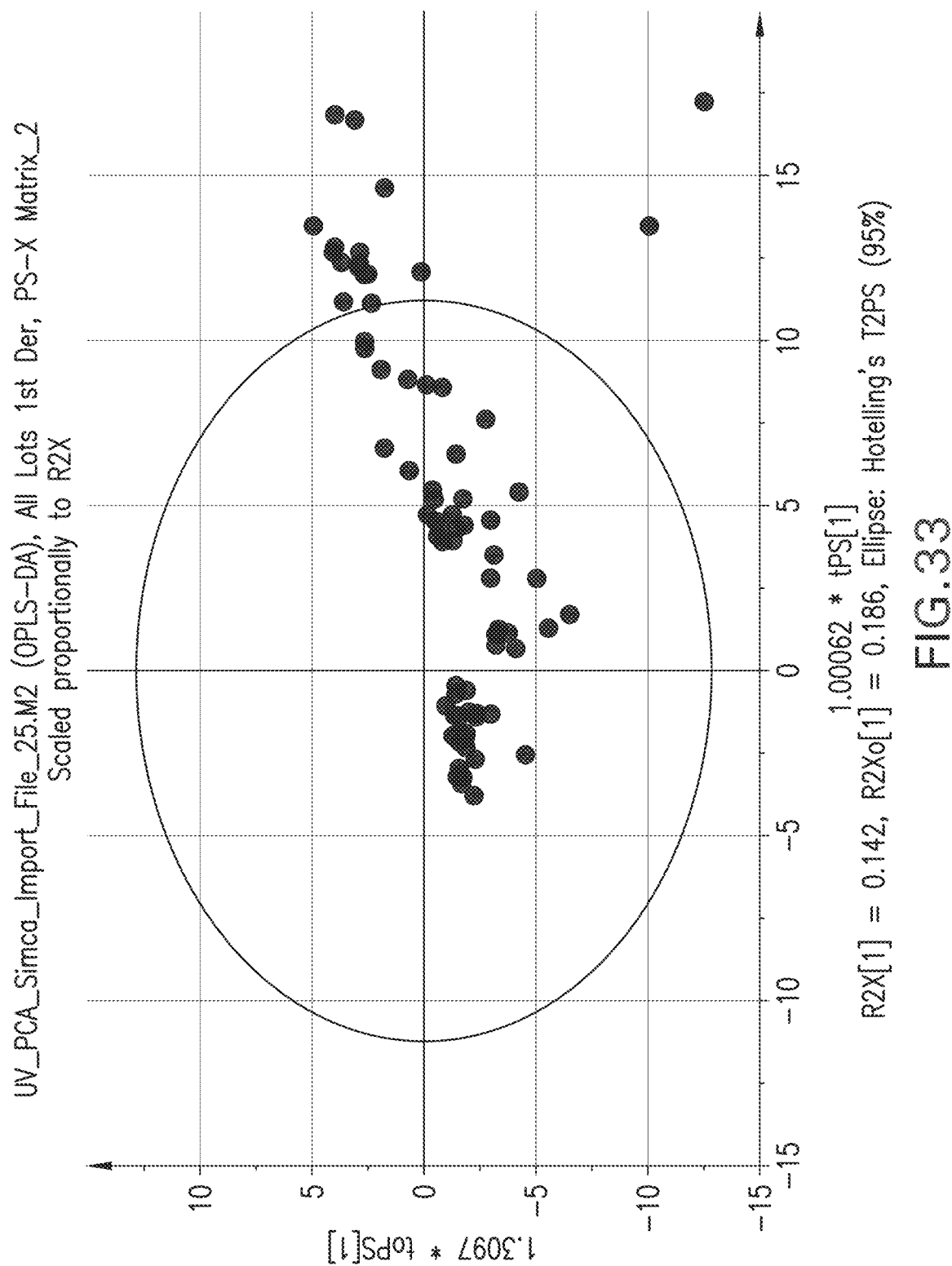
Figure 34:
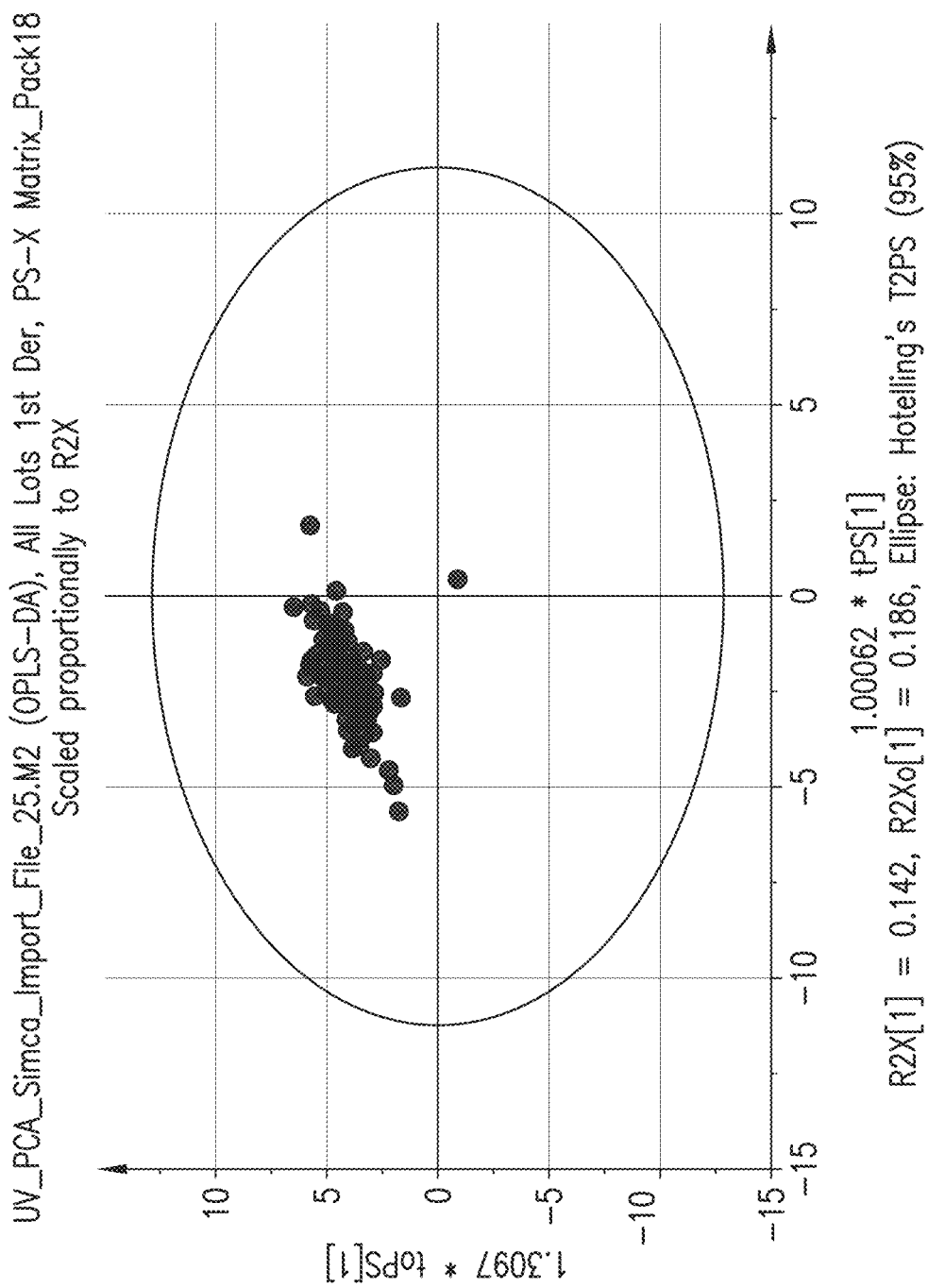

A UV OPLS model was generated using methods disclosed herein. As illustrated in FIG. 32-1 and FIG. 32-2, the generated OPLS model was able to differentiate between good/satisfactory lots (circles on left side) and bad/unsatisfactory lots (circles on right side). The generated model was able to identify column deterioration before it was readily apparent from historical overlay or through transition analysis. FIG. 33 is a plot generated using an OPLS model on Column Pack 1122600028. The model was able to detect column deterioration before it was apparent through visual observation (column data was not in training set). FIG. 34 is a plot generated from a Column Pack 1122600018. This column did not deteriorate as the model shows that column stayed within the good/satisfactory range (left side). Column remained robust entire lifetime demonstrates that model is working.

Example 2

Expanding Application of OPLS Models—Procedurally Generated Chromatograms (e.g. Chromatograms Artificially Generated, not from Actual Experimental Data)

Figure 35:
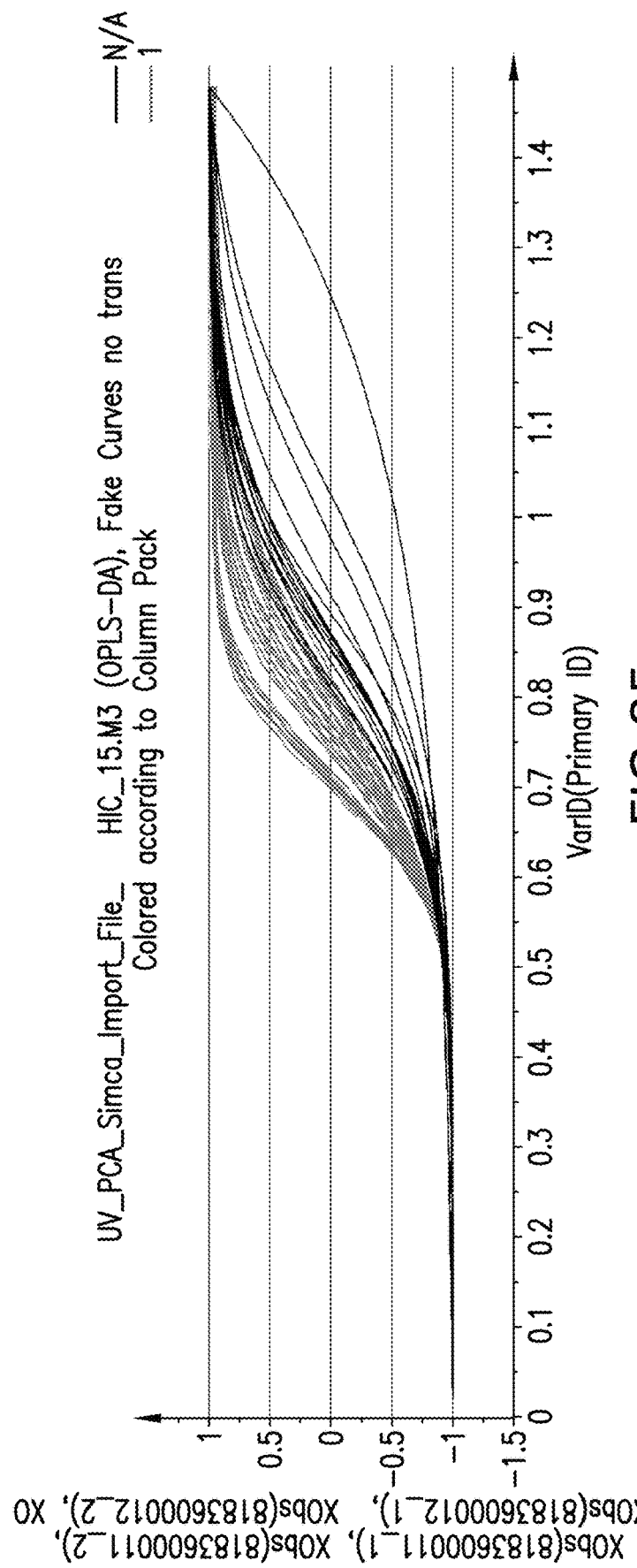

This example shows UV OPLS models can be created that are satisfactory without using lots where column deterioration was observed. For flow-through columns, the initial UV liftoff at the start of collection is expected to broaden as the column bed degrades. The liftoff can be modeled by the equation for logistic growth. Half of the data was selected and augmented with procedurally generated curves allowing the column to be calibrated. FIG. 35 illustrates the curves generated, blue was real data and green was information fed in based upon prediction.

Figure 36:
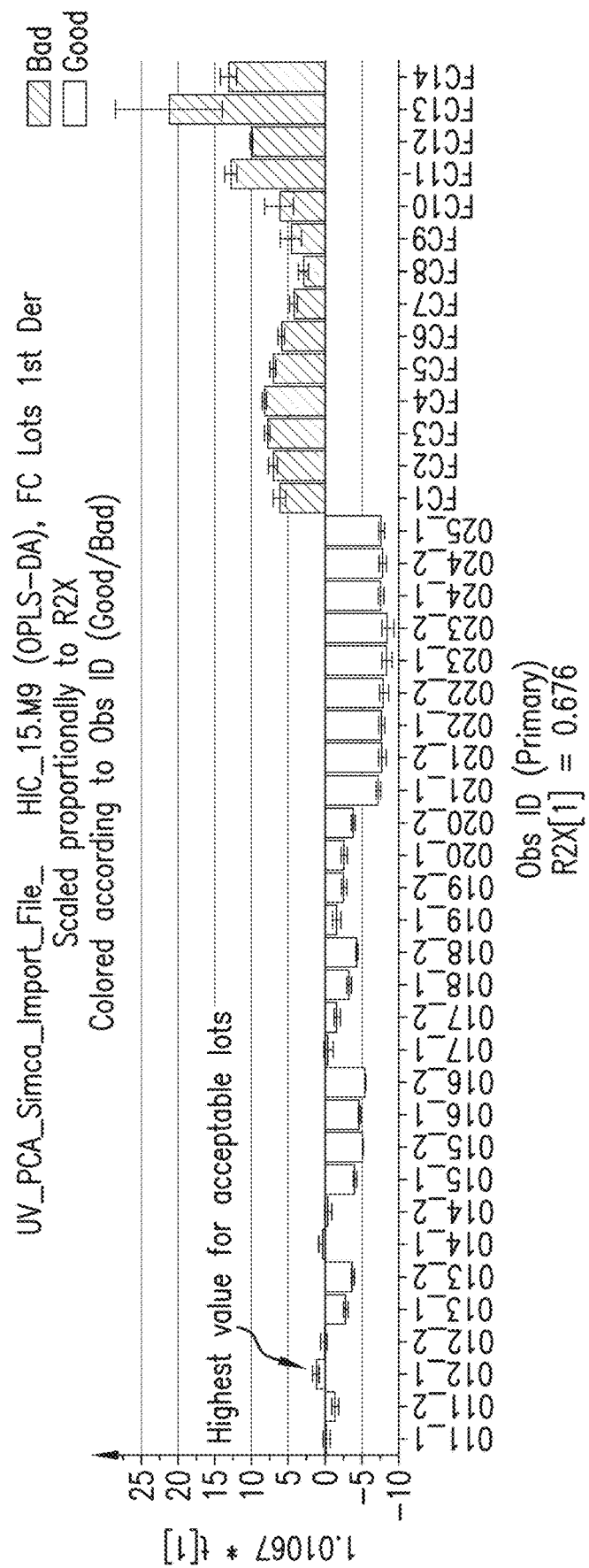

FIG. 36 shows the results of an OPLS model constructed using sample set of real acceptable historical data and procedurally generated curves representative of deterioration (e.g., chromatogram curves generated not from actual data) in which to make model more conservative, upper limit was set as the highest value for the acceptable lots used. Higher values were indicative of more column deterioration (not shown procedurally generated failures)

Figure 37:
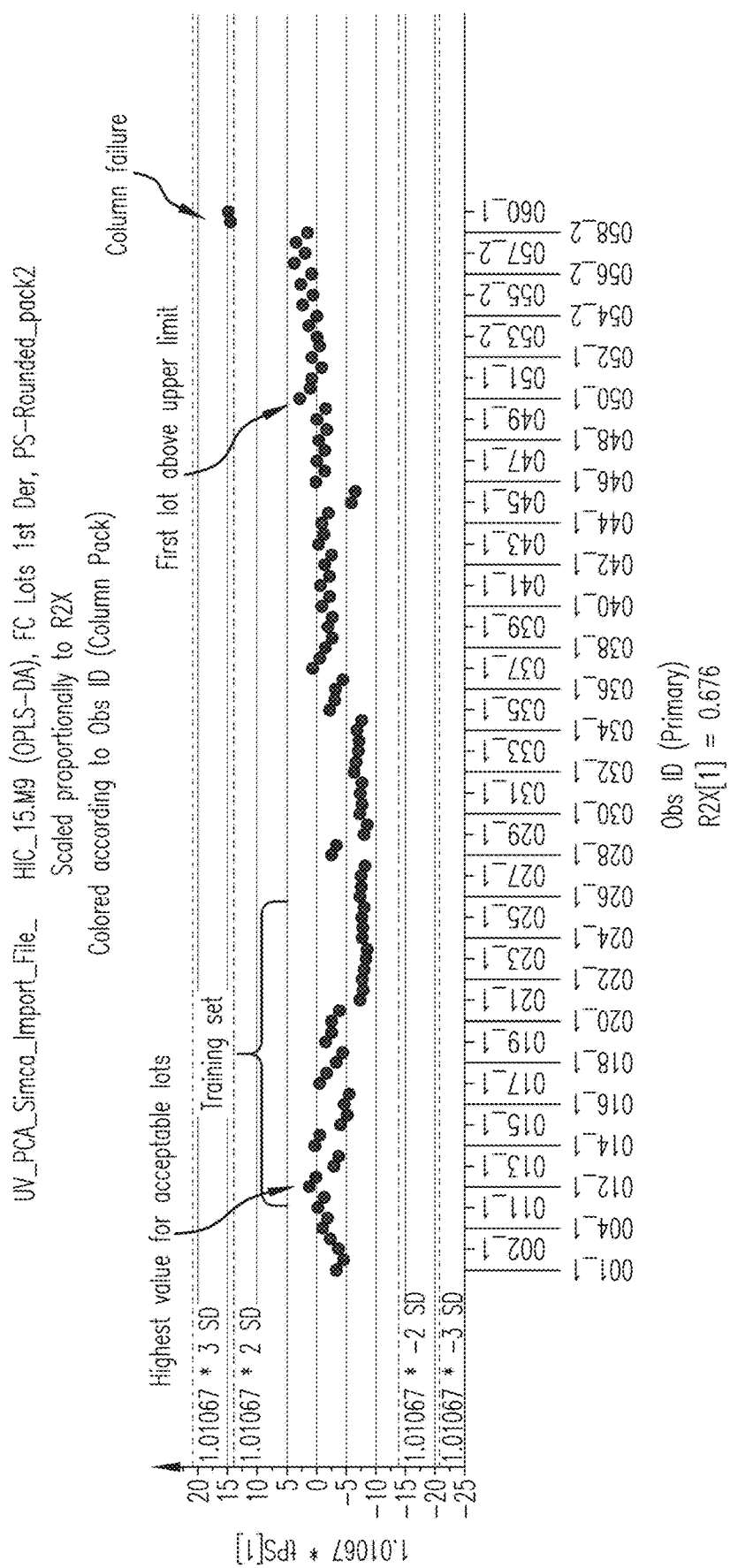

FIG. 37 shows the model was used to predict the performance of column pack 1194400001 in which the model was able to predict deterioration approximately 10 lots before column failure. This example indicates that OPLS modeling can be applied to UV signaling of chromatography to detect subtle, but important changes in column performance. Further, procedurally generated data can be used instead of a comprehensive training set with the disclosed models and still allow column deterioration to be modeled.

Example 3

OPLS Model Prediction

Figure 38A:
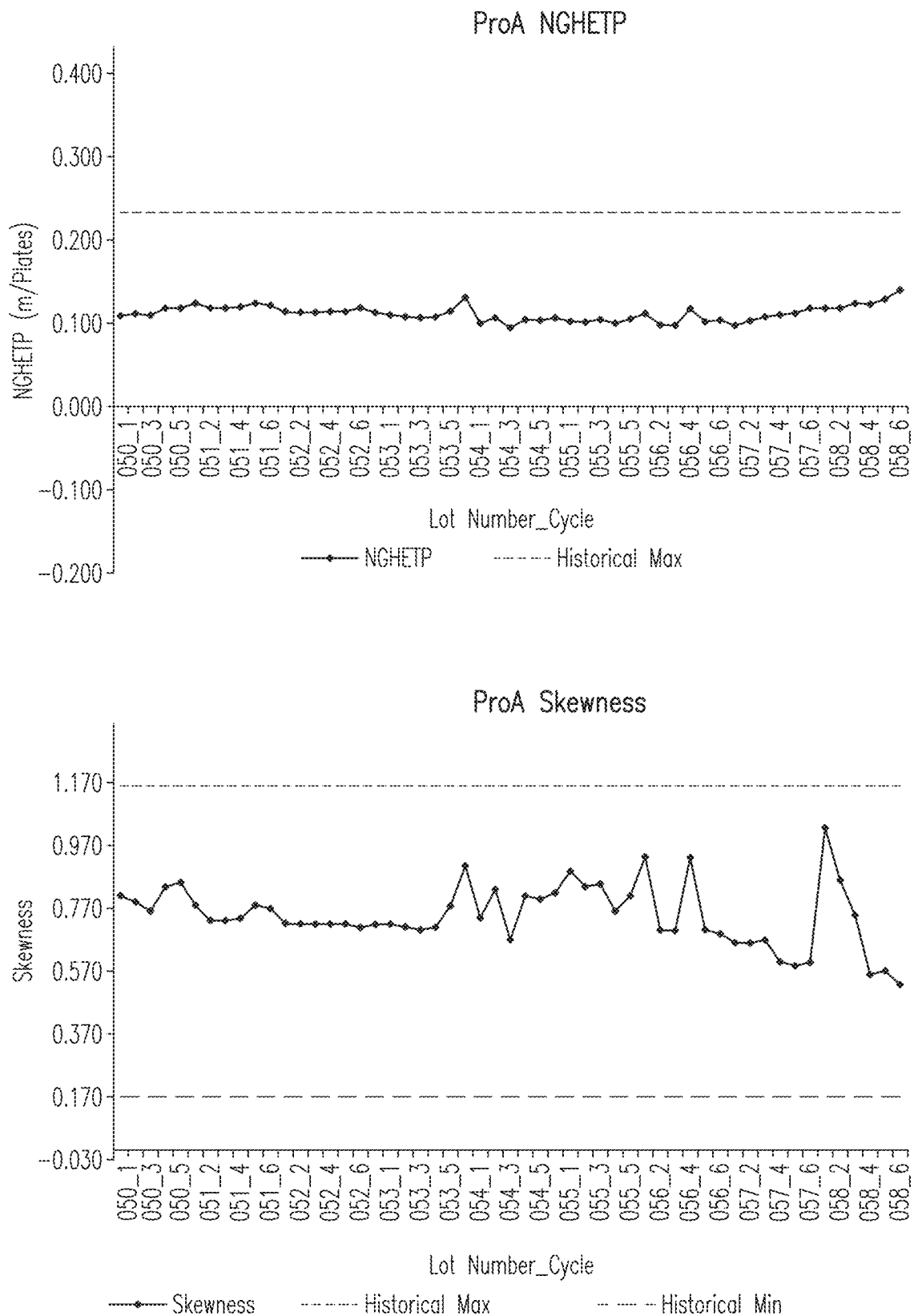
Figure 38B:
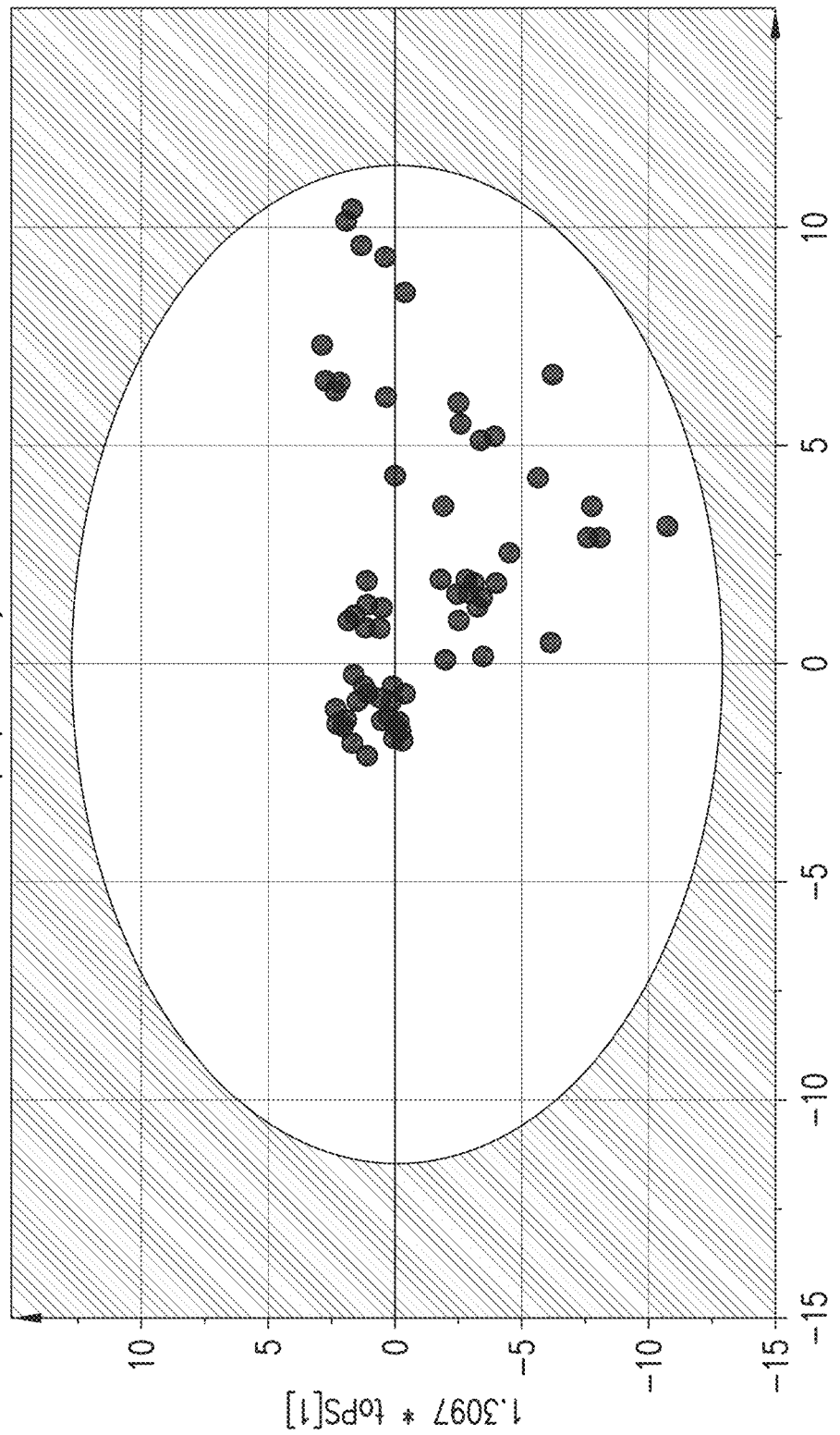
Figure 39A:
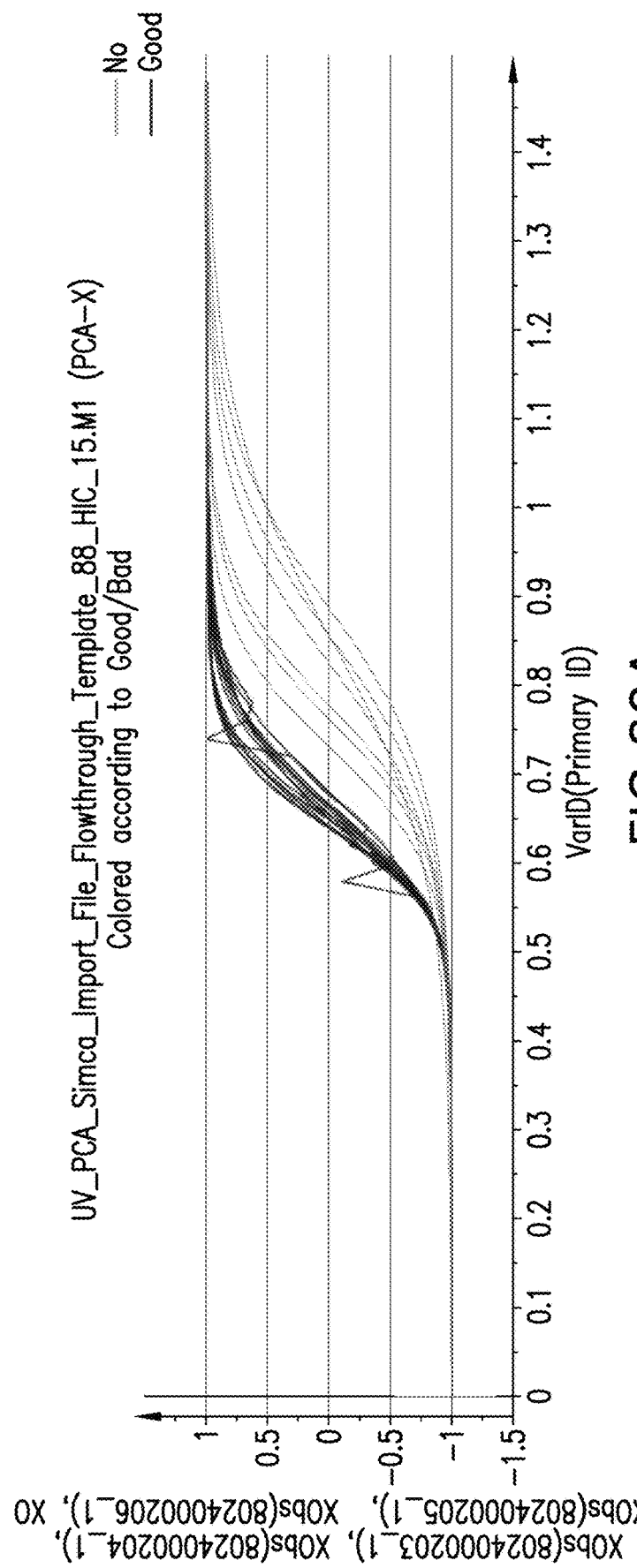
Figure 39B:
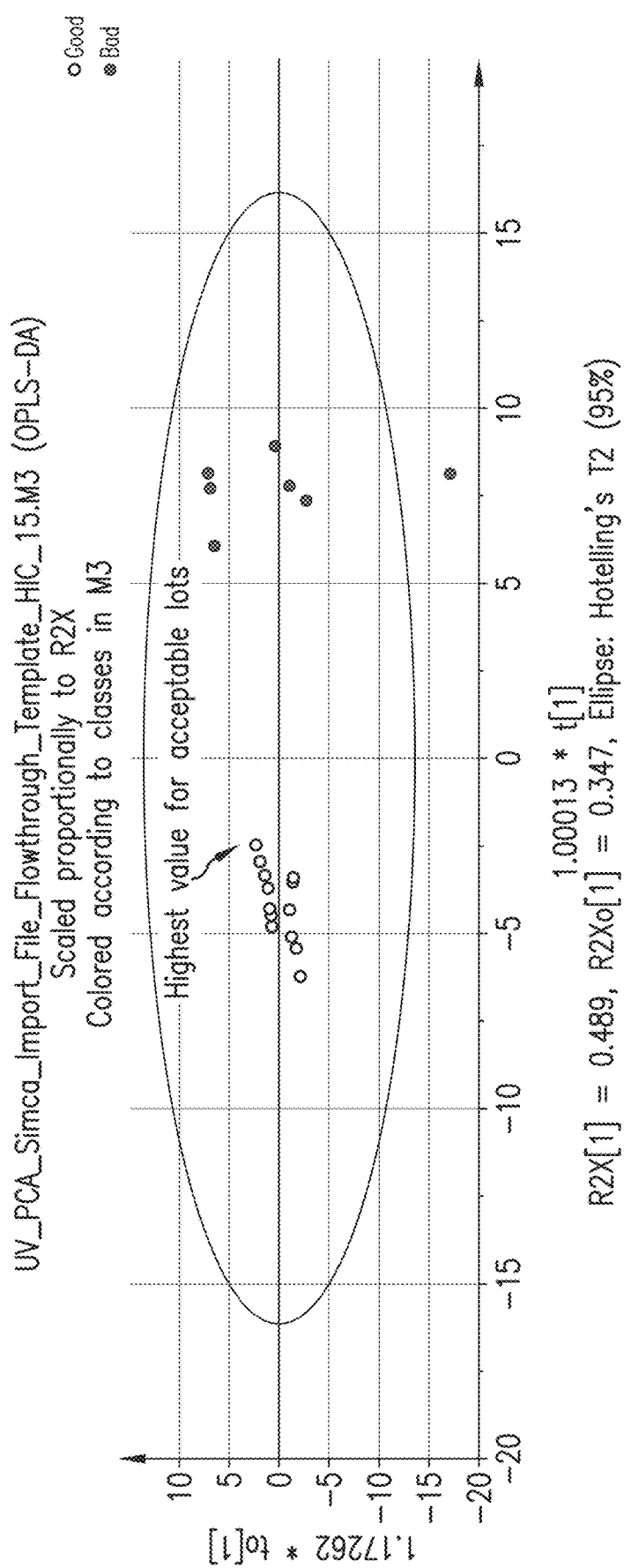
Figure 40:
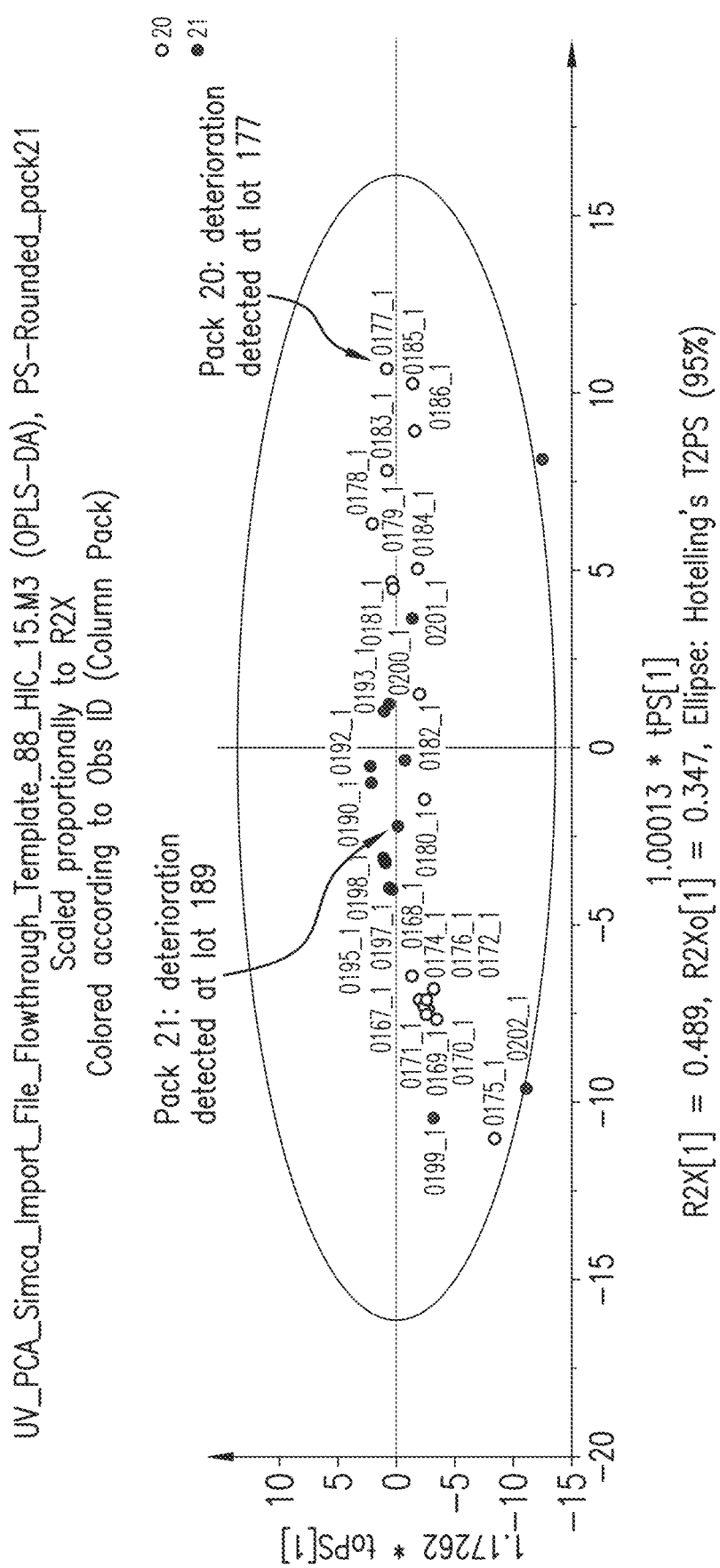

This example provides exemplary OPLS Model Prediction Data generated by the disclosed methods. FIGS. 38A and 38B illustrate the model prediction for column pack 1122600011. TA did not clearly show development of deterioration. Bifurcation was present in the next lot after the first lot to exceed x=4. Operation preceded PS repack recommendations. An OPLS model for hydrophobic interaction chromatography (HIC) using SME generated chromatograms was constructed. A procedure was developed to create curves based on the standard deviation of the values for the sample set of acceptable curves at 2 points. The results are shown in FIGS. 39A and 39B (Set x=−2.46 as upper limit (highest value for acceptable lots)). FIG. 40 illustrates the generated OPLS model was able to predict deterioration for column packs 20 & 21 without using data from historical failures. This example confirms that successful OPLS models can be made utilizing procedurally generated curves and a comprehensive training set is not required for the disclosed methods to be used to monitor column deterioration.

Overall, the disclosed methods provide a robust, sensitive method for monitoring column deterioration, which can be used to improve protein process development, including antibody process development.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of detecting chromatography column deterioration prior to column failure in a chromatography system, comprising:
   (i) creating an orthogonal partial least square (OPLS) model, wherein creating the OPLS model comprises:
      (a) selecting a process or unit operation for which the OPLS model is being created,
      (b) collecting raw data for ultraviolet (UV) chromatogram traces of one or more column cycles/lots/runs for the selected process or unit operation,
      (c) normalizing and aligning the collected raw data,
      (d) generating artificially created curves from normalized raw data,
      (e) classifying and formatting data for importation into a multivariate tool,
      (f) importing classified and formatted data into the multivariate tool to generate a training set of chromatogram traces, wherein the artificially created curves are classified as "undesirable" chromatogram traces in the training set,
      (g) generating the OPLS model from the multivariate tool using the training set,
      (h) optimizing and validating the generated OPLS model; and
   (ii) acquiring one or more chromatogram ultraviolet (UV) traces generated by a chromatography system during the selected process or unit operation; and
   (iii) applying the OPLS model to the one or more chromatogram UV traces, thereby allowing detection of column deterioration prior to column failure.

2. The method of claim 1, further comprising testing the optimized OPLS model.

3. The method of claim 1, wherein the process or unit operation is (a) a chromatography unit operation for a single molecule, or (b) a protein affinity chromatography step for the single molecule.

4. The method of claim 1, wherein:
   (a) collecting raw data for a UV trace of one or more column cycles/lots/runs for the selected process or unit operation comprises collecting UV absorbance values at corresponding column volumes for the one or more cycles/lots/runs; and/or
   (b) normalizing and aligning the collected raw data comprises normalizing and aligning UV absorbance values and aligning column volumes.

5. The method of claim 4, wherein normalizing UV absorbance values comprises removing variation in magnitude differences in UV raw signal.

6. The method of claim 1, further comprising providing a sample to the chromatography system prior to acquiring the one or more chromatogram ultraviolet (UV) traces generated by a chromatography system during sample purification and/or separation.

7. The method of claim 1, wherein the chromatography system is a liquid chromatography system.

8. The method of claim 6, wherein the sample comprises:
   (a) a protein;
   (b) an antibody, a fusion protein, recombinant protein, or a combination thereof;
   (c) a monoclonal antibody; or
   (d) a monoclonal antibody of isotype IgG1, IgG2, IgG3, IgG4, or mixed isotype.

9. A method of creating an orthogonal partial least square (OPLS) model for detection of chromatography column deterioration, comprising:
   (a) selecting a process or unit operation for which the OPLS model is being created;
   (b) collecting raw data for one or more ultraviolet (UV) chromatogram traces of one or more column cycles/lots/runs for the selected process or unit operation;
   (c) normalizing and aligning the collected raw data;
   (d) generating artificially created curves from normalized raw data;
   (e) classifying and formatting data for importation into a multivariate tool;
   (f) importing classified and formatted data into the multivariate tool to generate a training set, wherein the artificially created curves are classified as "undesirable" chromatogram traces for the training set; and
   (g) generating the OPLS model from the multivariate tool using the training set.

10. The method of claim 9, wherein the process or unit operation is (a) a chromatography unit operation for a single molecule, or (b) a protein affinity chromatography step for the single molecule.

11. The method of claim 9, wherein:
    (a) collecting raw data for a UV chromatogram trace of one or more column cycles/lots/runs for the selected process or unit operation comprises collecting UV absorbance values at corresponding column volumes for the one or more cycles/lots/runs; and/or
    (b) normalizing and aligning the collected raw data comprises normalizing and aligning UV absorbance values and aligning column volumes.

12. The method of claim 11, wherein normalizing UV absorbance values comprises removing variation in magnitude differences in UV raw signal.

13. The method of claim 9, wherein the one or more UV chromatogram traces is generated by a chromatography system during sample purification and/or separation.

14. A non-transitory computer-readable storage medium with an executable program stored thereon for detecting chromatography column deterioration in a chromatography system, wherein the program instructs a microprocessor to perform the steps of:
   (i) creating an orthogonal partial least square (OPLS) model, wherein creating the OPLS model comprises:
      (a) selecting a process or unit operation for which the OPLS model is being created,
      (b) collecting raw data for one or more ultraviolet (UV) chromatogram traces of one or more column cycles/lots/runs for the selected process or unit operation,
      (c) normalizing and aligning the collected raw data,
      (d) generating artificially created curves from normalized raw data,
      (e) classifying and formatting data for importation into a multivariate tool,
      (f) importing classified and formatted data into the multivariate tool to generate a training set of chromatogram traces; wherein the artificially created curves are classified as "undesirable" chromatogram traces in the training set;
      (g) generating the OPLS model from the multivariate tool using the training set; and
      (h) optimizing and validating the generated OPLS model, and
   (ii) acquiring one or more chromatogram ultraviolet (UV) traces generated by a chromatography system during sample purification and/or separation; and (iii) analyzing the one or more acquired chromatogram UV traces with the OPLS model, thereby allowing detection of column deterioration prior to column failure and quantitative analysis of UV signal in the one or more chromatogram UV traces.

15. The non-transitory computer-readable storage medium of claim 14, wherein the process or unit operation is (a) a chromatography unit operation for a single molecule, or (b) a protein affinity chromatography step for the single molecule.

16. The non-transitory computer-readable storage medium of claim 14, wherein:
(a) collecting raw data for a UV trace of one or more column cycles/lots/runs for the selected process or unit operation comprises collecting UV absorbance values at corresponding column volumes for the one or more cycles/lots/runs; and/or
(b) normalizing and aligning the collected raw data comprises normalizing and aligning UV absorbance values and aligning column volumes.

17. The non-transitory computer-readable storage medium of claim 16, wherein
normalizing UV absorbance values comprises removing variation in magnitude differences in UV raw signal.

18. The non-transitory computer-readable storage medium of claim 14, further comprising providing a sample to the chromatography system prior to acquiring the one or more chromatogram ultraviolet (UV) traces generated by a chromatography system during sample purification and/or separation.

* * * * *